(12) United States Patent
Packham et al.

(10) Patent No.: US 7,806,139 B2
(45) Date of Patent: Oct. 5, 2010

(54) FLUID CONDUIT COUPLING ASSEMBLY HAVING MALE AND FEMALE COUPLERS WITH INTEGRAL VALVES

(75) Inventors: Trent Turner Packham, Fort Collins, CO (US); Francis J. Lombardi, Fort Collins, CO (US); Leonard L. Hofheins, Provo, UT (US); Gregg D. Niven, Kaysville, UT (US); Robert J. Elshof, Fort Collins, CO (US); Raymond L. Townsend, Johnstown, CO (US); Richard W. Cairns, Longmont, CO (US)

(73) Assignee: Value Plastics, Inc., Fort Collins, CO (US)

(*) Notice: Subject to any disclaimer, the term of this patent is extended or adjusted under 35 U.S.C. 154(b) by 395 days.

(21) Appl. No.: 11/336,587

(22) Filed: Jan. 20, 2006

(65) Prior Publication Data

US 2007/0169825 A1    Jul. 26, 2007

(51) Int. Cl.
*F16L 37/34* (2006.01)
(52) U.S. Cl. .................. 137/614.05; 137/614.04; 251/149.6
(58) Field of Classification Search ............ 137/614.03, 137/614.04, 614.05, 614.02, 614; 251/231, 251/232, 236, 149.1, 149.6, 149.2, 149.5
See application file for complete search history.

(56) References Cited

U.S. PATENT DOCUMENTS

| 163,261 A | 5/1875 | Ruppenthal |
|---|---|---|
| 185,896 A | 1/1877 | Curtis |
| 187,982 A | 3/1877 | Pirsson et al. |
| 200,944 A * | 3/1878 | Smith ................ 137/614.03 |
| 235,580 A | 12/1880 | Smith et al. |
| 327,509 A | 10/1885 | Aldridge |
| 584,008 A | 6/1887 | Munson |
| 465,868 A | 12/1891 | List |
| 725,421 A | 4/1903 | Dinkins |
| 727,982 A | 5/1903 | Ludwig |

(Continued)

FOREIGN PATENT DOCUMENTS

WO    WO2006/135666    12/2006

OTHER PUBLICATIONS

Brochure, "Precision Components", Value Plastics, Inc., 2002.

(Continued)

*Primary Examiner*—Kevin L Lee
(74) *Attorney, Agent, or Firm*—Dorsey & Whitney LLP

(57) ABSTRACT

The present invention is a fluid conduit coupling assembly for coupling a first fluid conduit to a second fluid conduit. The fluid conduit coupling assembly comprises a first coupler and a second coupler. The first coupler is for connecting to the first fluid conduit and comprises a first housing and a first valve. The first valve comprises a first lever arm. The second coupler is for connecting to the second fluid conduit and comprises a second housing and a second valve. The second valve comprises a second lever arm. When a force is applied to couple together the couplers, at least a portion of said force is communicated to each lever arm, thereby causing each valve to pivot from a closed position to an open position. The first valve and first lever arm are contained within the first housing, and the second valve and second lever arm are contained within the second housing.

18 Claims, 53 Drawing Sheets

U.S. PATENT DOCUMENTS

| | | | |
|---|---|---|---|
| 874,957 A | 12/1907 | Godley | |
| 884,461 A | 4/1908 | Browne | |
| 909,131 A | 1/1909 | Antic | |
| 951,889 A | 3/1910 | Teuer | |
| 1,029,819 A | 6/1912 | Nylander | |
| 1,033,187 A | 7/1912 | Metzger | |
| 1,039,354 A | 9/1912 | Bonadio | |
| 1,077,417 A | 11/1913 | McCracken | |
| 1,078,112 A | 11/1913 | Storm | |
| 1,115,945 A * | 11/1914 | Kunz | 251/149.2 |
| 1,193,446 A | 8/1916 | Wells | |
| 1,239,345 A | 9/1917 | Brown | |
| 1,255,847 A | 2/1918 | Arkin | |
| 1,259,684 A | 3/1918 | Vinten | |
| 1,489,310 A | 4/1924 | Critchlow | |
| 1,526,218 A * | 2/1925 | Johnson | 137/614.03 |
| 1,578,504 A | 3/1926 | Bronson et al. | |
| 1,587,079 A | 6/1926 | Machino | |
| 1,767,073 A | 6/1930 | Ingold | |
| 1,863,360 A | 6/1932 | Weatherhead | |
| 1,950,947 A | 3/1934 | Mulroyan | |
| 2,023,428 A | 12/1935 | Liebhardt | |
| 2,056,524 A | 10/1936 | Johnson | |
| 2,066,473 A | 1/1937 | Jorgensen | |
| 2,097,628 A | 11/1937 | Liebhardt | |
| 2,099,335 A | 11/1937 | Hansen | |
| 2,108,714 A * | 2/1938 | Hirsch et al | 137/614.04 |
| 2,139,745 A | 12/1938 | Goodall | |
| 2,147,355 A | 2/1939 | Scholtes | |
| 2,159,116 A | 5/1939 | Zacharias | |
| 2,211,147 A | 8/1940 | Miller | |
| 2,257,321 A | 9/1941 | Arnold | |
| 2,263,293 A | 11/1941 | Ewald | |
| 2,340,119 A | 1/1944 | Graham | |
| 2,346,445 A | 4/1944 | Merker et al. | |
| 2,352,728 A | 7/1944 | Merker et at. | |
| 2,429,782 A | 10/1947 | Versoy | |
| 2,432,946 A | 12/1947 | Theunissen | |
| 2,470,800 A | 5/1949 | Ashton | |
| 2,479,499 A | 8/1949 | Le Clair | |
| 2,500,720 A | 3/1950 | Van der Heem | |
| 2,507,536 A | 5/1950 | Goodson | |
| 2,516,583 A | 7/1950 | Moore | |
| 2,535,740 A | 12/1950 | Knopp | |
| 2,577,009 A | 12/1951 | Frantz | |
| 2,626,974 A | 1/1953 | Howard et al. | |
| 2,630,131 A | 3/1953 | Snyder | |
| 2,661,018 A | 12/1953 | Snyder | |
| 2,701,147 A | 2/1955 | Summerville | |
| 2,722,399 A | 11/1955 | Oetiker | |
| 2,753,195 A | 7/1956 | Palmer | |
| 2,774,616 A | 12/1956 | Dodd et al. | |
| 2,790,571 A | 4/1957 | Flaith et al. | |
| 2,864,628 A | 12/1958 | Edleson | |
| 2,915,325 A | 12/1959 | Foster | |
| 2,926,934 A | 3/1960 | Gill | |
| 2,931,668 A | 4/1960 | Baley | |
| 2,937,892 A | 5/1960 | Prescott, Jr. | |
| 2,948,553 A | 8/1960 | Gill et al. | |
| 2,991,090 A | 7/1961 | De Cenzo | |
| 3,017,203 A | 1/1962 | Macleod | |
| 3,037,497 A | 6/1962 | Roberson | |
| 3,073,342 A | 1/1963 | Magorien | |
| 3,078,068 A | 2/1963 | Romney | |
| D196,473 S | 10/1963 | Hill | |
| 3,124,157 A | 3/1964 | Krzewina | |
| 3,171,196 A | 3/1965 | Helitas | |
| 3,217,771 A | 11/1965 | Beall et al. | |
| 3,227,380 A | 1/1966 | Pinkston | |
| 3,237,974 A | 3/1966 | Press | |
| 3,245,703 A | 4/1966 | Manly | |
| 3,276,799 A | 10/1966 | Moore et al. | |
| 3,279,497 A * | 10/1966 | Norton et al | 137/614.03 |
| 3,314,696 A | 4/1967 | Ferguson et al. | |
| D209,166 S | 11/1967 | Hunt | |
| D209,168 S | 11/1967 | Hunt | |
| 3,352,576 A | 11/1967 | Thomas | |
| 3,382,892 A | 5/1968 | Cerbin | |
| 3,403,930 A | 10/1968 | Bernier | |
| 3,448,760 A | 6/1969 | Cranage | |
| 3,450,424 A | 6/1969 | Calisher | |
| 3,512,808 A | 5/1970 | Graham | |
| 3,523,701 A | 8/1970 | Graham | |
| 3,538,940 A | 11/1970 | Graham | |
| 3,542,338 A * | 11/1970 | Scaramucci | 251/209 |
| 3,545,490 A | 12/1970 | Burrus | |
| 3,550,626 A | 12/1970 | Daniels et al. | |
| 3,560,027 A | 2/1971 | Graham | |
| 3,563,265 A | 2/1971 | Graham | |
| 3,574,314 A | 4/1971 | Quercia | |
| 3,588,149 A | 6/1971 | Demler | |
| 3,596,933 A | 8/1971 | Luckenbill | |
| 3,599,843 A | 8/1971 | Johnston | |
| 3,600,917 A | 8/1971 | Krock | |
| 3,690,336 A | 9/1972 | Drum | |
| 3,712,583 A | 1/1973 | Martindale et al. | |
| 3,750,238 A | 8/1973 | Tanner | |
| 3,815,887 A | 6/1974 | Curtis et al. | |
| 3,817,561 A | 6/1974 | Kay | |
| 3,876,234 A | 4/1975 | Harms | |
| 3,889,710 A | 6/1975 | Brost | |
| 3,899,200 A | 8/1975 | Gamble | |
| 3,921,656 A | 11/1975 | Meisenheimer, Jr. et al. | |
| 3,979,934 A | 9/1976 | Isenmann | |
| 3,990,674 A | 11/1976 | Schattenberg | |
| 4,025,049 A | 5/1977 | Schmidt | |
| 4,039,213 A | 8/1977 | Walters | |
| 4,072,330 A | 2/1978 | Brysch | |
| 4,099,748 A | 7/1978 | Kavick | |
| 4,129,145 A | 12/1978 | Wynn | |
| 4,142,546 A | 3/1979 | Sandau | |
| D252,470 S | 7/1979 | Pawlak | |
| 4,181,149 A | 1/1980 | Cox | |
| D254,505 S | 3/1980 | Parsons et al. | |
| D255,145 S | 5/1980 | Nederman | |
| 4,220,360 A | 9/1980 | Jacek et al. | |
| D258,526 S | 3/1981 | Nederman | |
| D259,278 S | 5/1981 | McCaw | |
| 4,271,865 A | 6/1981 | Galloway et al. | |
| 4,287,644 A | 9/1981 | Durand | |
| 4,296,949 A | 10/1981 | Muetterties et al. | |
| 4,319,774 A | 3/1982 | Kavick | |
| 4,330,010 A | 5/1982 | Drescher et al. | |
| 4,330,142 A | 5/1982 | Paini | |
| 4,331,175 A | 5/1982 | Brake et al. | |
| 4,331,177 A | 5/1982 | Makishima | |
| 4,340,200 A | 7/1982 | Stegmeier | |
| 4,345,786 A | 8/1982 | Egert | |
| 4,346,703 A | 8/1982 | Dennehey | |
| 4,351,351 A | 9/1982 | Flory et al. | |
| 4,366,816 A | 1/1983 | Bayard et al. | |
| 4,393,548 A | 7/1983 | Herb | |
| 4,397,442 A | 8/1983 | Larkin | |
| 4,434,121 A | 2/1984 | Schaper | |
| 4,436,125 A | 3/1984 | Blenkush | |
| 4,437,689 A | 3/1984 | Goebel et al. | |
| 4,439,188 A | 3/1984 | Dennehey | |
| 4,458,719 A | 7/1984 | Strybel | |
| 4,500,118 A | 2/1985 | Blenkush | |
| 4,527,745 A | 7/1985 | Butterfield et al. | |
| 4,541,457 A | 9/1985 | Blenkush | |
| 4,541,657 A | 9/1985 | Smyth | |
| D282,962 S | 3/1986 | Gerber | |
| 4,603,888 A | 8/1986 | Goodall et al. | |

| | | | | | | |
|---|---|---|---|---|---|---|
| 4,613,112 | A | 9/1986 | Phlipot et al. | 5,547,166 A | 8/1996 | Engdahl |
| 4,616,859 | A | 10/1986 | Brunet | 5,553,895 A | 9/1996 | Karl et al. |
| 4,632,436 | A | 12/1986 | Kimura | D375,160 S | 10/1996 | Sampson et al. |
| 4,658,326 | A | 4/1987 | Clark et al. | 5,568,946 A | 10/1996 | Jackowski |
| 4,694,544 | A | 9/1987 | Chapman | 5,595,217 A | 1/1997 | Gillen et al. |
| 4,699,298 | A | 10/1987 | Grant et al. | 5,628,726 A | 5/1997 | Cotter |
| 4,703,957 | A | 11/1987 | Blenkush | D380,262 S | 6/1997 | Van Funderburk et al. |
| 4,706,847 | A | 11/1987 | Sankey et al. | D387,147 S | 12/1997 | Vandermast et al. |
| 4,712,280 | A | 12/1987 | Fildan | 5,695,223 A | 12/1997 | Boticki |
| 4,738,401 | A | 4/1988 | Filicicchia | D388,876 S | 1/1998 | Sampson |
| 4,753,268 | A | 6/1988 | Palau | 5,709,244 A | 1/1998 | Patriquin et al. |
| 4,776,067 | A | 10/1988 | Sorensen | 5,725,258 A | 3/1998 | Kujawski |
| 4,790,567 | A | 12/1988 | Kawano et al. | 5,737,810 A | 4/1998 | Krauss |
| 4,790,569 | A | 12/1988 | Chaffee | 5,745,957 A | 5/1998 | Khokhar et al. |
| 4,792,115 | A | 12/1988 | Jindra et al. | 5,746,414 A | 5/1998 | Weldon et al. |
| 4,793,637 | A | 12/1988 | Laipply et al. | 5,762,646 A | 6/1998 | Cotter |
| D300,361 | S | 3/1989 | Tokarz | 5,799,987 A | 9/1998 | Sampson |
| 4,827,921 | A | 5/1989 | Rugheimer | 5,820,614 A | 10/1998 | Erskine et al. |
| 4,832,237 | A | 5/1989 | Hurford, Jr. | 5,845,943 A | 12/1998 | Ramacier, Jr. et al. |
| 4,834,423 | A | 5/1989 | DeLand | 5,855,568 A | 1/1999 | Battiato et al. |
| 4,844,512 | A | 7/1989 | Gahwiler | 5,882,047 A | 3/1999 | Ostrander et al. |
| 4,863,201 | A | 9/1989 | Carstens | D407,803 S | 4/1999 | Redman |
| 4,896,402 | A | 1/1990 | Jansen et al. | 5,897,142 A | 4/1999 | Kulevsky |
| 4,900,065 | A | 2/1990 | Houck | 5,911,367 A | 6/1999 | McInerney |
| 4,903,995 | A | 2/1990 | Blenkush et al. | 5,911,403 A | 6/1999 | deCler et al. |
| 4,923,228 | A | 5/1990 | Laipply et al. | 5,911,404 A | 6/1999 | Cheng |
| 4,934,655 | A | 6/1990 | Blenkush et al. | 5,930,424 A | 7/1999 | Heimberger et al. |
| 4,935,992 | A | 6/1990 | Due | 5,938,244 A | 8/1999 | Meyer |
| 4,949,745 | A | 8/1990 | McKeon | 5,941,577 A | 8/1999 | Musellec |
| 4,969,879 | A | 11/1990 | Lichte | D413,967 S | 9/1999 | Yuen |
| D313,067 | S | 12/1990 | Kotake et al. | 5,957,898 A | 9/1999 | Jepson et al. |
| D313,277 | S | 12/1990 | Haining | 5,964,485 A | 10/1999 | Hame et al. |
| D314,050 | S | 1/1991 | Sone | 5,975,489 A | 11/1999 | deCler et al. |
| D314,233 | S | 1/1991 | Medvick | 5,984,378 A | 11/1999 | Ostrander et al. |
| 4,982,736 | A | 1/1991 | Schneider | 6,015,171 A | 1/2000 | Schorn |
| 4,991,880 | A | 2/1991 | Bernart | D419,861 S | 2/2000 | Khokhar |
| 5,009,252 | A | 4/1991 | Faughn | 6,024,124 A | 2/2000 | Braun et al. |
| 5,033,777 | A | 7/1991 | Blenkush | 6,029,701 A | 2/2000 | Chaffardon et al. |
| 5,052,725 | A | 10/1991 | Meyer et al. | 6,032,691 A | 3/2000 | Powell et al. |
| 5,074,601 | A | 12/1991 | Spors et al. | D422,487 S | 4/2000 | Khokhar |
| 5,076,615 | A | 12/1991 | Sampson | 6,050,297 A | 4/2000 | Ostrowski et al. |
| 5,078,429 | A | 1/1992 | Braut et al. | 6,076,234 A | 6/2000 | Khokhar et al. |
| 5,090,448 | A * | 2/1992 | Truchet ................. 137/614.03 | 6,077,259 A | 6/2000 | Caizza et al. |
| 5,090,747 | A | 2/1992 | Kotake | 6,082,401 A | 7/2000 | Braun et al. |
| 5,094,482 | A | 3/1992 | Petty et al. | 6,089,540 A | 7/2000 | Heinrichs et al. |
| 5,104,158 | A | 4/1992 | Meyer et al. | 6,112,855 A | 9/2000 | Camacho et al. |
| D326,155 | S | 5/1992 | Boehringer et al. | 6,123,690 A | 9/2000 | Mejslov |
| 5,112,084 | A | 5/1992 | Washizu | 6,135,150 A | 10/2000 | Powell et al. |
| 5,114,250 | A | 5/1992 | Usui | 6,135,992 A | 10/2000 | Wang |
| 5,123,677 | A | 6/1992 | Kreczko et al. | 6,152,914 A | 11/2000 | Van De Kerkhof et al. |
| 5,160,177 | A | 11/1992 | Washizu | 6,161,578 A | 12/2000 | Braun et al. |
| 5,165,733 | A | 11/1992 | Sampson | 6,182,694 B1 | 2/2001 | Sievers et al. |
| 5,176,406 | A | 1/1993 | Straghan | 6,189,560 B1 | 2/2001 | Reynolds |
| D333,178 | S | 2/1993 | Novy | 6,199,919 B1 | 3/2001 | Kawasaki et al. |
| 5,190,224 | A | 3/1993 | Hamilton | 6,221,064 B1 | 4/2001 | Nadal |
| 5,222,279 | A | 6/1993 | Frano et al. | 6,231,089 B1 | 5/2001 | DeCler et al. |
| 5,228,724 | A | 7/1993 | Godeau | D444,054 S | 6/2001 | Bernard et al. |
| 5,232,020 | A | 8/1993 | Mason et al. | 6,257,626 B1 | 7/2001 | Campau |
| D339,417 | S | 9/1993 | Sampson et al. | 6,261,282 B1 | 7/2001 | Jepson et al. |
| 5,316,041 | A | 5/1994 | Ramacier, Jr. et al. | 6,293,596 B1 | 9/2001 | Kinder |
| 5,330,235 | A | 7/1994 | Wagner et al. | 6,302,147 B1 | 10/2001 | Rose et al. |
| 5,356,183 | A | 10/1994 | Cole | 6,318,764 B1 | 11/2001 | Trede et al. |
| 5,374,088 | A | 12/1994 | Moretti et al. | 6,344,033 B1 | 2/2002 | Jepson et al. |
| 5,385,311 | A | 1/1995 | Morikawa et al. | D459,206 S | 6/2002 | Caveney et al. |
| 5,385,331 | A | 1/1995 | Allread et al. | 6,402,207 B1 | 6/2002 | Segal et al. |
| D357,307 | S | 4/1995 | Ramacier, Jr. et al. | 6,423,053 B1 | 7/2002 | Lee |
| 5,405,339 | A | 4/1995 | Kohnen et al. | 6,481,759 B1 | 11/2002 | Kawasaki et al. |
| 5,405,340 | A | 4/1995 | Fageol et al. | 6,485,483 B1 | 11/2002 | Fujii |
| 5,437,650 | A | 8/1995 | Larkin et al. | 6,505,866 B1 | 1/2003 | Nakamura et al. |
| 5,494,074 | A | 2/1996 | Ramacier, Jr. et al. | 6,520,546 B2 | 2/2003 | Szabo |
| 5,507,733 | A | 4/1996 | Larkin et al. | D471,261 S | 3/2003 | Kozu |
| D372,093 | S | 7/1996 | Sampson et al. | 6,540,263 B1 | 4/2003 | Sausner |
| 5,536,258 | A | 7/1996 | Folden | 6,595,964 B2 | 7/2003 | Finley et al. |

| | | |
|---|---|---|
| 6,612,634 B1 | 9/2003 | Zoppas |
| 6,626,465 B2 | 9/2003 | Lacroix et al. |
| 6,641,177 B1 | 11/2003 | Pinciaro |
| 6,649,829 B2 | 11/2003 | Garber et al. |
| 6,652,007 B1 | 11/2003 | Hwang |
| 6,669,681 B2 | 12/2003 | Jepson et al. |
| 6,676,172 B2 | 1/2004 | Alksnis |
| 6,688,654 B2 | 2/2004 | Romero |
| 6,692,038 B2 | 2/2004 | Braun |
| 6,722,705 B2 | 4/2004 | Korkor |
| 6,783,520 B1 | 8/2004 | Candray et al. |
| 6,799,747 B1 | 10/2004 | Lai |
| 6,840,277 B1 | 1/2005 | Nimberger |
| 6,848,723 B2 | 2/2005 | Lamich |
| 6,871,878 B2 | 3/2005 | Miros |
| D503,778 S | 4/2005 | Wicks |
| 6,886,803 B2 | 5/2005 | Mikiya et al. |
| 6,897,374 B2 | 5/2005 | Garber et al. |
| 6,899,315 B2 | 5/2005 | Maiville et al. |
| 6,929,246 B2 | 8/2005 | Arzenton et al. |
| 6,945,273 B2 | 9/2005 | Reid |
| 6,949,084 B2 | 9/2005 | Marggi et al. |
| 6,997,919 B2 | 2/2006 | Olsen et al. |
| 7,005,581 B2 | 2/2006 | Burnette |
| 7,011,342 B2 | 3/2006 | Guivarc'h et al. |
| D522,109 S | 5/2006 | White et al. |
| 7,044,161 B2 | 5/2006 | Tiberghien |
| 7,044,506 B2 | 5/2006 | Dong |
| 7,108,297 B2 | 9/2006 | Takayanagi et al. |
| 7,128,348 B2 | 10/2006 | Kawamura et al. |
| 7,137,654 B2 | 11/2006 | Segal et al. |
| 7,147,252 B2 | 12/2006 | Teuscher et al. |
| 7,153,296 B2 | 12/2006 | Mitchell |
| D550,355 S | 9/2007 | Racz et al. |
| 7,343,931 B2 * | 3/2008 | Packham ............... 137/614.04 |
| D569,955 S | 5/2008 | Chen |
| D570,457 S | 6/2008 | Brown |
| 7,390,029 B2 | 6/2008 | Matsubara |
| 7,677,608 B2 | 3/2010 | Takayanagi |
| 2001/0054819 A1 | 12/2001 | Guest |
| 2004/0232696 A1 | 11/2004 | Andre |
| 2005/0001425 A1 | 1/2005 | deCler et al. |
| 2005/0012330 A1 | 1/2005 | Schmidt |
| 2005/0057042 A1 | 3/2005 | Wicks |
| 2005/0082828 A1 | 4/2005 | Wicks et al. |
| 2005/0211934 A1 | 9/2005 | Garber et al. |
| 2005/0258646 A1 | 11/2005 | Gunderson |
| 2007/0029796 A1 | 2/2007 | Bibby |
| 2007/0209716 A1 | 9/2007 | Rankin |
| 2008/0061553 A1 | 3/2008 | Schmidt |
| 2009/0256355 A1 | 10/2009 | Wicks et al. |
| 2010/0001516 A1 | 1/2010 | Pisula, Jr. et al. |

OTHER PUBLICATIONS

Supplemental Notice of Allowability, U.S. Appl. No. 11/149,624, 6 pages, Jul. 3, 2008.

* cited by examiner

FLUID CONDUIT COUPLING ASSEMBLY HAVING MALE AND FEMALE COUPLERS WITH INTEGRAL VALVES

FIELD OF THE INVENTION

The present invention relates to coupling assemblies for fluid conduits and methods of using and manufacturing such coupling assemblies. More particularly, the present invention relates coupling assemblies having male and female interlocking couplers with integral valves.

BACKGROUND OF THE INVENTION

Quick connect/disconnect coupling assemblies for small flexible tube applications are known in the art. Such coupling assemblies are utilized for bio-medical applications, convenience handling, beverage dispensing, pneumatic instrument connections, photochemical handling, etc. Despite the existence of such coupling assemblies, there is a need in the art for a coupling assembly that offers higher flow rates, improved coupling security, simplified operation, positive fluid shut-off when detached, and decreased manufacturing costs.

SUMMARY OF THE INVENTION

The present invention, in a first embodiment, is a fluid conduit coupling assembly for coupling a first fluid conduit to a second fluid conduit. The fluid conduit coupling assembly comprises a first coupler and a second coupler. The first coupler includes a first mating end, a first attachment end for attaching to the first fluid conduit, a first fluid flow path extending between the first mating end and the first attachment end, and a first valve in the first fluid flow path. The second coupler includes a second mating end for mating with the first mating end, a second attachment end for attaching to the second fluid conduit, a second fluid flow path extending between the second mating end and the second attachment end, and a first member adapted to open the first valve when the first and second mating ends are mated together such that the first and second fluid flow paths are joined.

In one version of the first embodiment, the second coupler further includes a second valve in the second fluid flow path, and the first coupler further includes a second member adapted to open the second valve when the first and second mating ends are mated together such that the first and second fluid flow paths are joined.

In one version of the first embodiment, the first valve is pivotal between an open position and a closed position. In one version of the first embodiment, the first valve is a stopcock, plug valve or ball valve. The first valve includes a lever arm and the first member encounters the lever arm when the first and second mating ends are mated together, thereby causing the valve to pivot to the open position. The first valve is biased to the closed position.

In one version of the first embodiment, the valve is a helical spring. In one version of the first embodiment, the first fluid flow path has a circular cross-section through the first valve. In another version of the first embodiment, the first fluid flow path has a non-circular cross-section through the first valve. In one such version of the first embodiment, said non-circular cross-section is generally rectangular.

The present invention, in a second embodiment, is a fluid conduit coupling assembly for coupling a first fluid conduit to a second fluid conduit. The fluid conduit coupling assembly comprises a first coupler and a second coupler. The first coupler includes a first mating end, a first attachment end for attaching to the first fluid conduit, a first fluid flow path extending between the first mating end and the first attachment end, a first valve in the first fluid flow path, and a first valve actuator operably coupled to the first valve. The second coupler includes a second mating end for mating with the first mating end, a second attachment end for attaching to the second fluid conduit, and a second fluid flow path extending between the second mating end and the second attachment end. When the first and second mating ends are mated together such that the first and second fluid flow paths are joined, the first valve actuator abuts against a portion of the second coupler and is displaced, thereby causing the first valve to open.

In one version of the second embodiment, the second coupler further includes a second valve in the second fluid flow path and a second valve actuator operably coupled to the second valve. When the first and second mating ends are mated together such that the first and second fluid flow paths are joined, the second valve actuator abuts against a portion of the first coupler and is displaced, thereby causing the second valve to open. In one version of the second embodiment, said portion of the second coupler is the second valve actuator and said portion of the first coupler is the first valve actuator.

In one version of the second embodiment, the first valve is pivotal between an open position and a closed position. In one version of the second embodiment, the first valve is a stopcock, plug valve or ball valve. The first valve is biased to a closed position. In one version of the second embodiment, the first valve is biased to a closed position via a biasing member acting on the first valve actuator.

In one version of the second embodiment, the first fluid flow path has a circular cross-section through the first valve. In another version of the second embodiment, the first fluid flow path has a non-circular cross-section through the first valve. In one such version of the second embodiment, said non-circular cross-section is generally rectangular.

In one version of the second embodiment, the first valve actuator retreats into the first coupler upon abutting against said portion of the second coupler. In one version of the second embodiment, the first valve actuator displaces in a direction generally parallel to a longitudinal axis of the first fluid flow path upon abutting against said portion of the second coupler. In one version of the second embodiment, the first valve actuator telescopically displaces about the first fluid flow path upon abutting against said portion of the second coupler.

The present invention, in one embodiment, is a fluid conduit coupling assembly for coupling a first fluid conduit to a second fluid conduit. The fluid conduit coupling assembly comprises a first coupler and a second coupler. The first coupler is for connecting to the first fluid conduit and comprises a first housing and a first valve. The first valve comprises a first lever arm. The second coupler is for connecting to the second fluid conduit and comprises a second housing and a second valve. The second valve comprises a second lever arm. When a force is applied to couple together the couplers, at least a portion of said force is communicated to each lever arm, thereby causing each valve to pivot from a closed position to an open position. The first valve and first lever arm are contained within the first housing, and the second valve and second lever arm are contained within the second housing.

In one embodiment, the first coupler further comprises a first structural member, and the second coupler further comprises a second structural member. When the couplers are coupled together, the first structural member extends into the second coupler to contact the second lever arm and the second structural member extends into the first coupler to contact the first lever arm.

In one embodiment, the first coupler further comprises a first body operably coupled to the first lever arm, and the second coupler further comprises a second body operably coupled to the second lever arm. When the couplers are coupled together, the first body is displaced relative to the first housing via contact with a portion of the second coupler and the second body is displaced relative to the second housing via contact with a portion of the first coupler. In one embodiment, said portion of the first coupler is the first body and said portion of the second coupler is the second body.

The present invention, in one embodiment, is a method of coupling a first fluid conduit to a second fluid conduit. The method comprises providing a first coupler connected to the first fluid conduit and a second coupler connected to the second fluid conduit. Each coupler includes a housing and a valve with a lever arm. A mating end of the first coupler is aligned with a mating end of the second coupler. A force is applied to the couplers to cause the mating ends to engage. At least a portion of the force is communicated to the lever arm of each valve to cause each valve to pivot from a closed position to an open position. In one embodiment, when the mating ends engage, a structural member of each coupler enters the other coupler and displaces the lever arm of said other coupler. In one embodiment, when the mating ends engage, a body member of each coupler encounters a portion of the other coupler and displaces relative to its respective housing to cause its respective valve to pivot.

The present invention, in one embodiment, is a fluid conduit coupling assembly. The fluid conduit coupling assembly comprises a first coupler and a second coupler. The couplers are adapted to couple to each other. Each coupler includes a stopcock, plug valve or ball valve that is caused to pivot from a closed position to an open position via the act of coupling together the couplers. In one embodiment, each valve further includes a means for causing each valve to pivot during the act of coupling together the couplers.

The present invention, in one embodiment, is a valve comprising a valve body received in a valve seat opening. The valve body is formed of a first polymer with a durometer range of approximately 60 to approximately 65 Rockwell R Scale. The valve seat opening is formed of a second polymer with a durometer range of approximately 118 to approximately 122 Rockwell R Scale. The valve body is press fit into the seat opening to cause the surfaces of the valve body and valve seat opening to interface. The press fit generally maintains pressure between the interfaced surfaces of the valve body and valve seat opening in the range of approximately 2.0 psi to approximately 45.0 psi. A fluid flow path extends through the valve body. In one embodiment the fluid flow path has a diameter transverse to the longitudinal length of the valve body that is at least approximately 10 percent of the diameter of the valve body. In another embodiment, the fluid flow path has a diameter transverse to the longitudinal length of the valve body that is less than approximately 75 percent of the diameter of the valve body. In one embodiment, the interface between the surfaces of the valve body and valve seat opening is the only sealing mechanism employed by the valve to prevent fluid flow between the surfaces of the valve body and valve seat opening.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

DETAILED DESCRIPTION OF THE INVENTION a. Overview of Coupling Assemblies

The present invention is a quick disconnect coupling assembly for connecting the ends of two fluid conduits such as the small flexible tubing utilized in bio-medical applications, convenience handling, beverage dispensing, instrument connections, photochemical handling, etc. The quick disconnect coupling assembly of the present invention is particularly useful in connecting two fluid conduits in a biomedical environment. The coupling assembly of the present invention is ergonomically designed, easily and securely connected, and yet easily intentionally disconnected. The coupling assembly of the subject invention has a male coupler with an integral valve and a female coupler with an integral valve. Each valve is biased closed via a biasing mechanism, but opens automatically by simply connecting the male and female couplers together. Upon the male and female couplers being disconnected from each other, each valve closes automatically via its integral biasing mechanism.

In a first embodiment of the coupling assembly of the subject invention, the male and female couplers each have a structural member. When the male and female couplers are being connected, their respective structural members enter the other coupler to cause the valve of the other coupler to open. When the male and female couplers are disengaged from each other, their respective structural members exit the other coupler and the valve of the other coupler is allowed to bias closed.

In a second embodiment of the coupling assembly of the subject invention, the male and female couplers each have a body that is displaceable within its respective coupler. When the male and female couplers are being connected, their respective bodies contact each other. This contact causes each body to displace within its respective coupler, which causes the valve of the respective coupler to open. When the male and female couplers are disengaged from each other, their respective bodies cease contacting each other and the valves are allowed to bias closed.

b. First Embodiment of the Quick Disconnect Coupling Assembly

Figure 1:
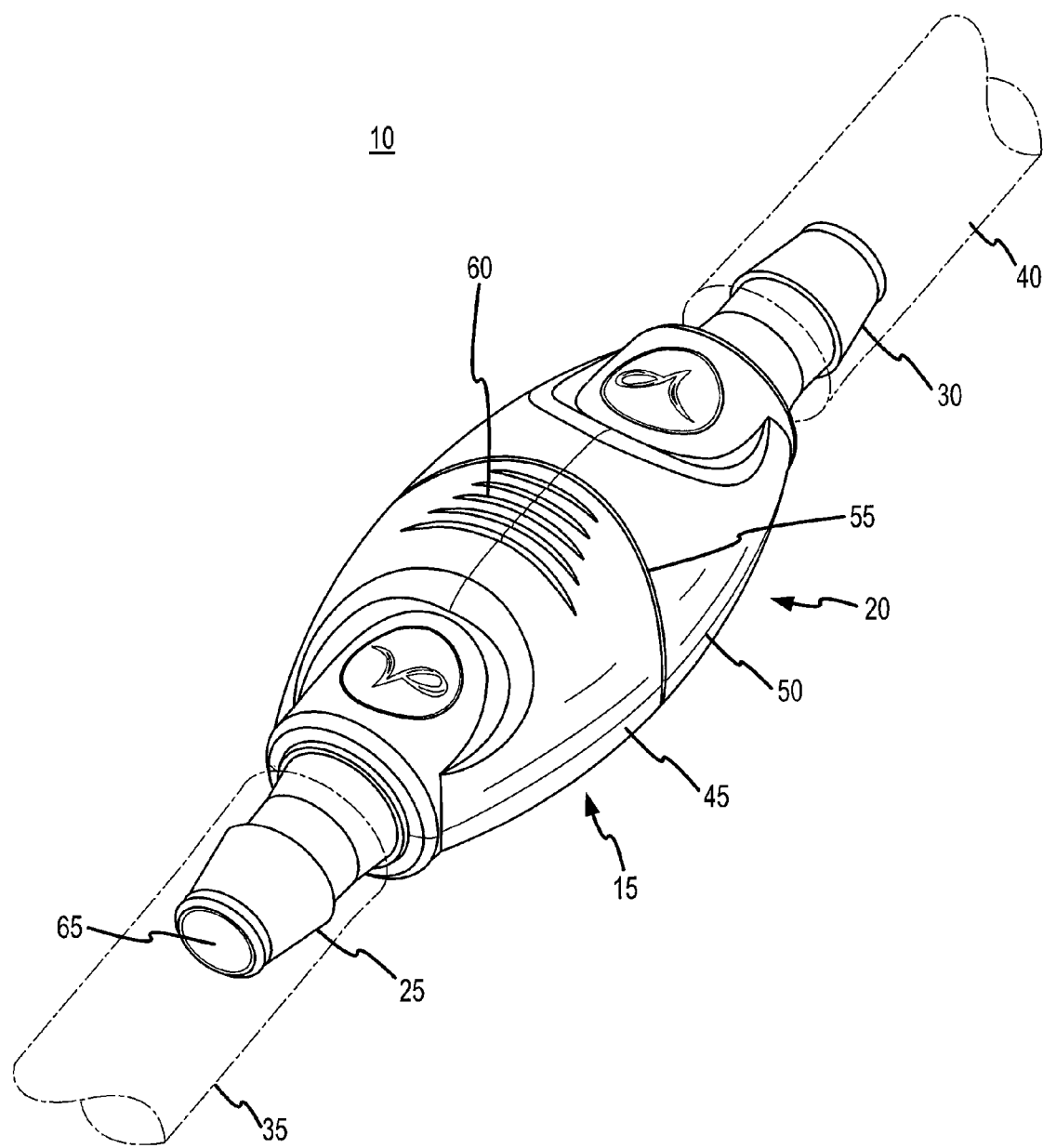
FIG. 1 is an isometric view of the quick disconnect coupling assembly, wherein the male coupler and female coupler are connected.
Figure 2:
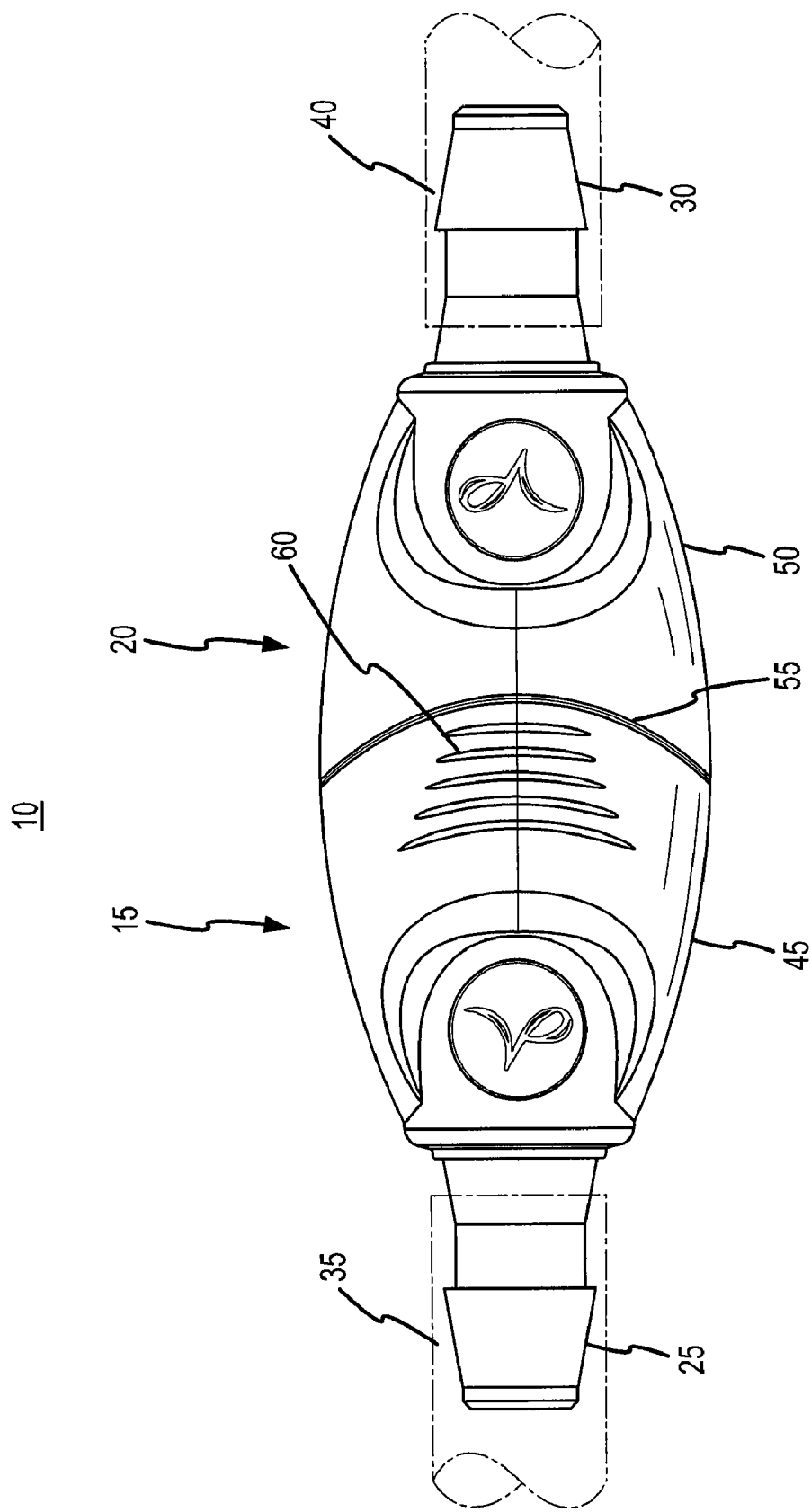
FIG. 2 is a top plan of the coupling assembly in the same connected state as depicted in FIG. 1.
Figure 3:
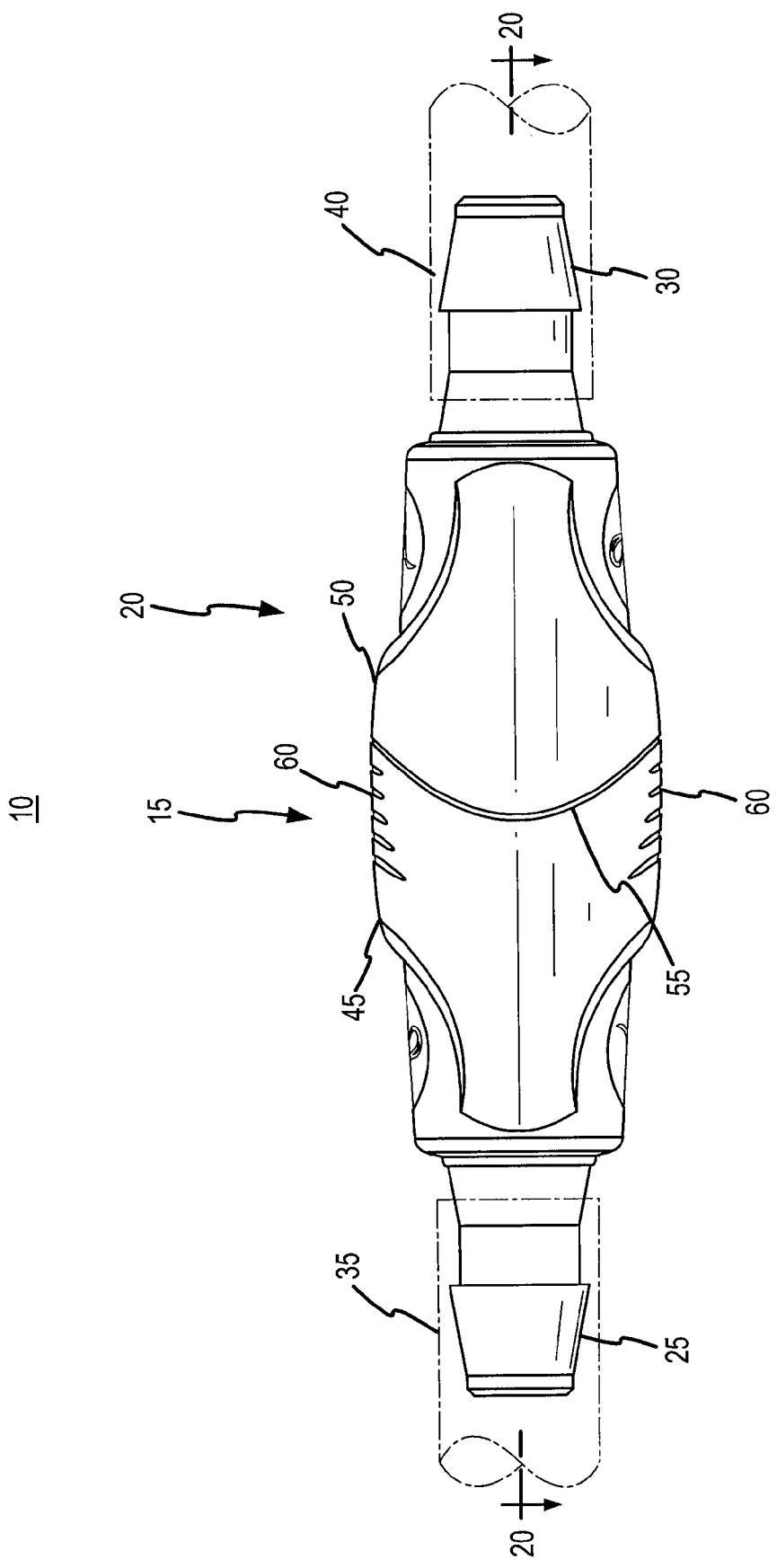
FIG. 3 is a side elevation of the coupling assembly in the same connected state depicted in FIG. 1.
Figure 4:
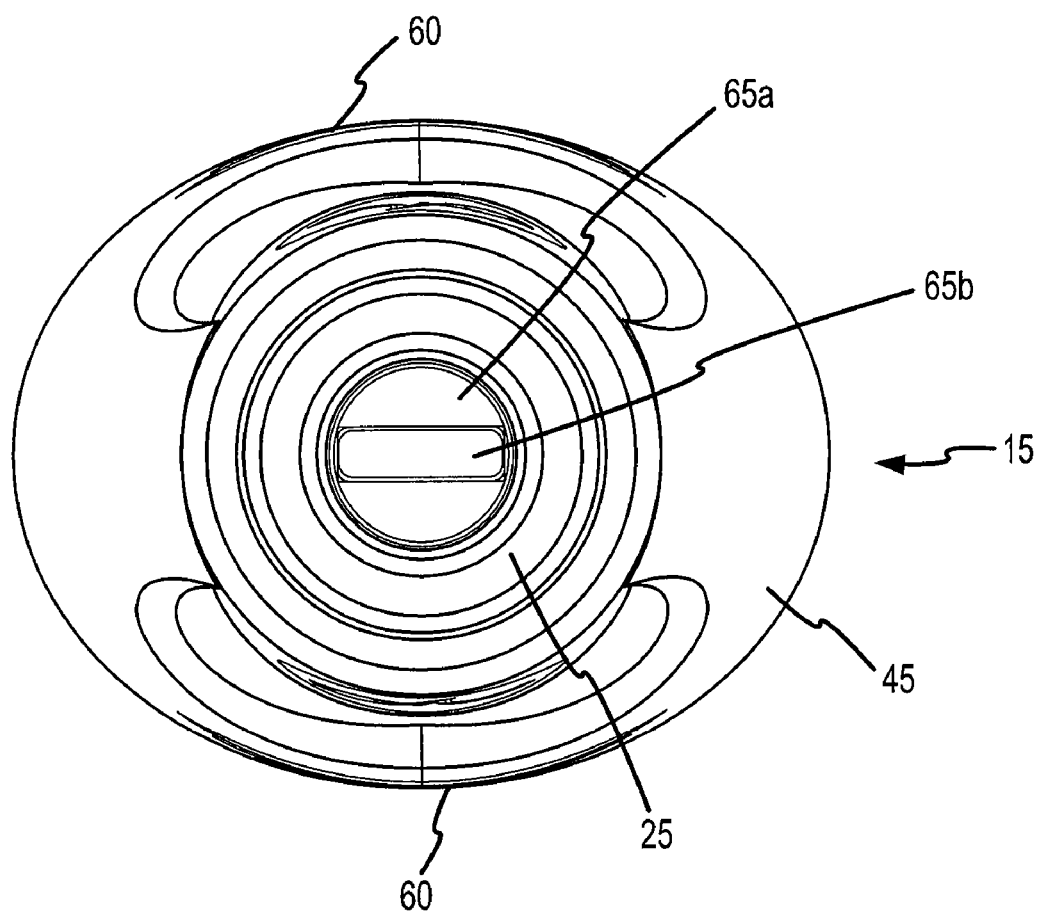
FIG. 4 is an end elevation of the coupling assembly in the same connected state depicted in FIG. 1 and as viewed from the male coupler end.

For a discussion of the first embodiment of the quick disconnect coupling assembly 10 of the present invention, reference is made to FIGS. 1-4. FIG. 1 is an isometric view of the quick disconnect coupling assembly 10, wherein the male coupler 15 and female coupler 20 are connected. FIG. 2 is a top plan of the coupling assembly 10 in the same connected state as depicted in FIG. 1. While a bottom plan of the coupling assembly 10 is not provided, it should be understood that it would appear identical to the view depicted in FIG. 2. FIG. 3 is a side elevation of the coupling assembly 10 in the same connected state depicted in FIG. 1. While a view of the opposite side of the coupling assembly 10 is not provided, it should be understood that it would appear identical to the view depicted in FIG. 3. FIG. 4 is an end elevation of the coupling assembly 10 in the same connected state depicted in FIG. 1 and as viewed from the male coupler end. While a view of the coupling assembly 10 as viewed from the female coupler end is not provided, it should be understood that it would appear identical to the view depicted in FIG. 4.

As shown in FIG. 1-3, the quick disconnect coupling assembly 10 includes a male coupler 15 and a female coupler 20. Each coupler 15, 20 includes a barbed end 25, 30 for insertion into, and connection with, a fluid conduit 35, 40 such as medical grade flexible tubing. Each coupler 15, 20 includes a housing or shroud 45, 50 that forms the exterior shell of each coupler 15, 20. When the couplers 15, 20 are connected, as depicted in FIGS. 1-3, the housings 45, 50 form a body that is semi-elliptical or egg-shaped as viewed from above or below, as shown in FIG. 2. When the couplers 15, 20 are connected, the joining ends of the housings 45, 50 of each coupler 15, 20 abut along a seam 55 that arcuately transitions as the seam 55 circumferentially latitudinally extends about the exterior shell of the coupling assembly 10 such that the male coupler housing 45 arcuately extends past the mid-point of the coupling assembly 10 at the top and bottom of the coupling assembly 10, and the female coupler housing 50 arcuately extends past the mid-point of the coupling assembly 10 at the sides of the coupling assembly 10. The male coupling housing 45 includes a group of latitudinally extending slots 60 that provide friction contact points for a user's fingers when disengaging an engagement mechanism (shown in later described figures) that hold the couplers 15, 20 together.

As can be understood from FIGS. 1 and 4, a fluid flow path 65 extends through the coupler assembly 10 from the male coupler barbed end 25 to the female coupler barbed end 30. In one embodiment, as indicated in FIG. 4, and as will be described with greater detail later in this Detailed Description, the fluid flow path 65 transitions from a circular cross-section 65a to a rectangular cross-section 65b and back to a circular cross-section 65a as the fluid flow path 65 extends through the coupler assembly 10.

Figure 5:
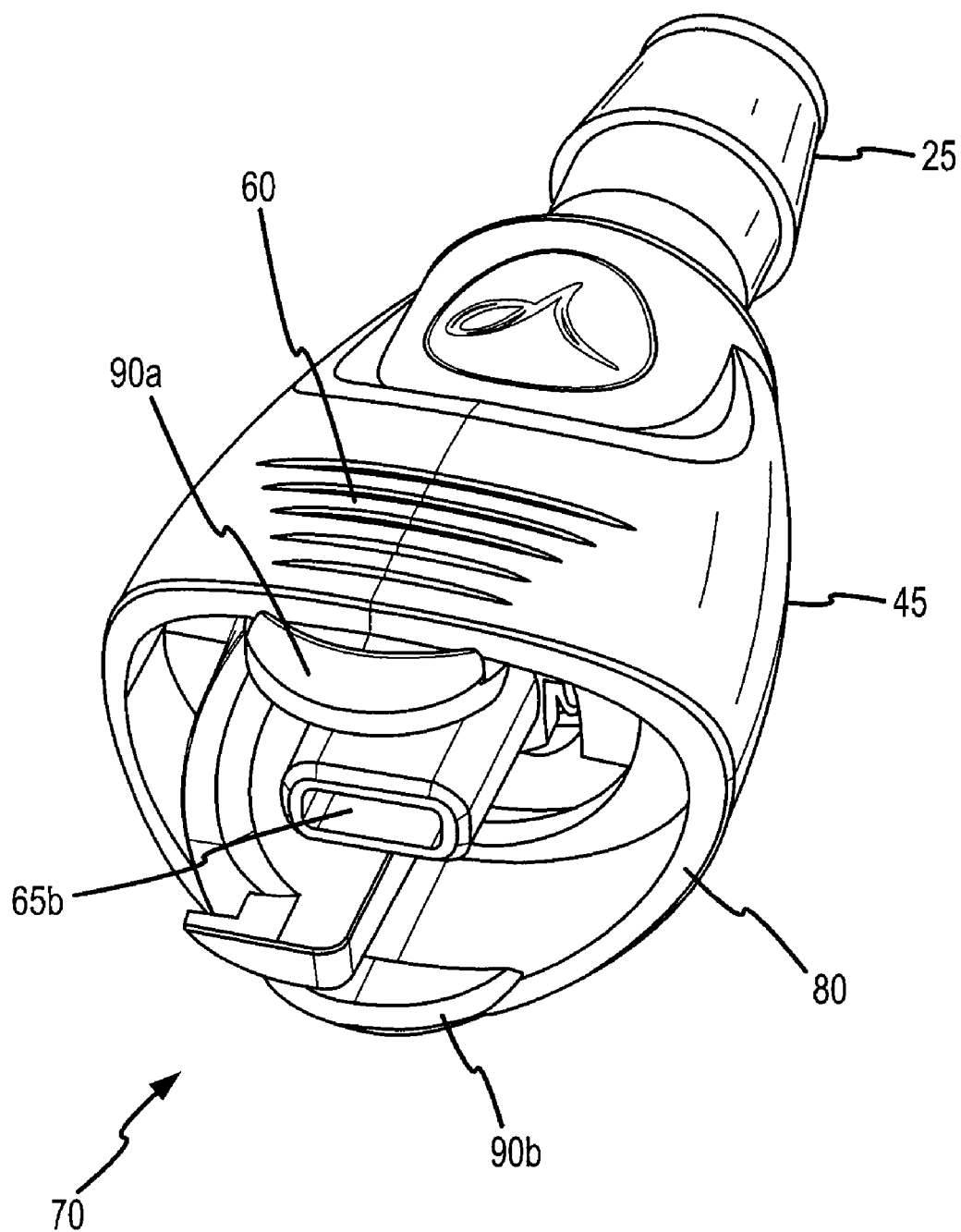
FIG. 5 is an isometric view of the male coupler as viewed from the joining side of the male coupler.
Figure 6:
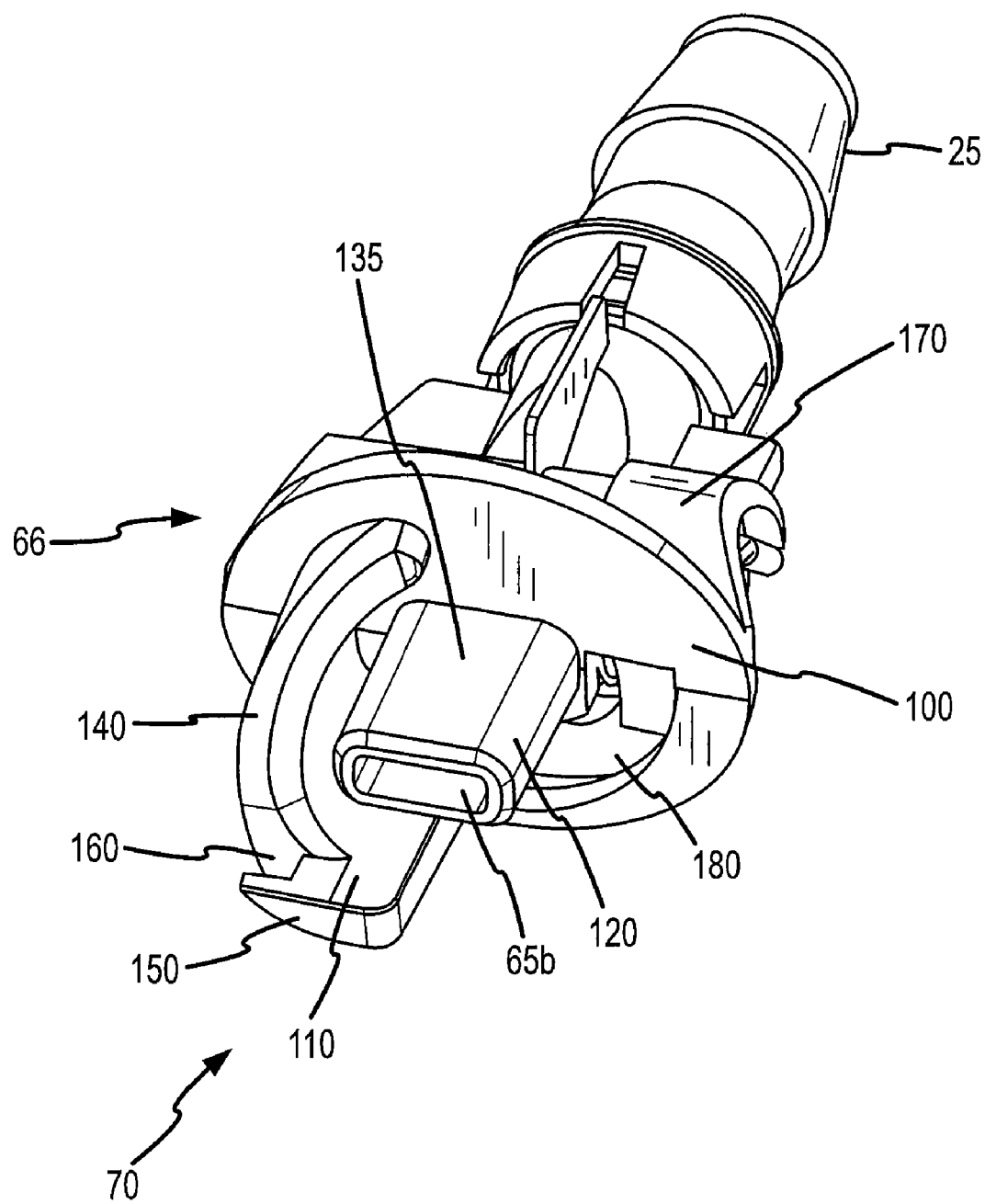
FIG. 6 is the same view of the male coupler depicted in FIG. 5, except the male coupler housing has been removed from the male coupler to reveal the male barrel.
Figure 7:
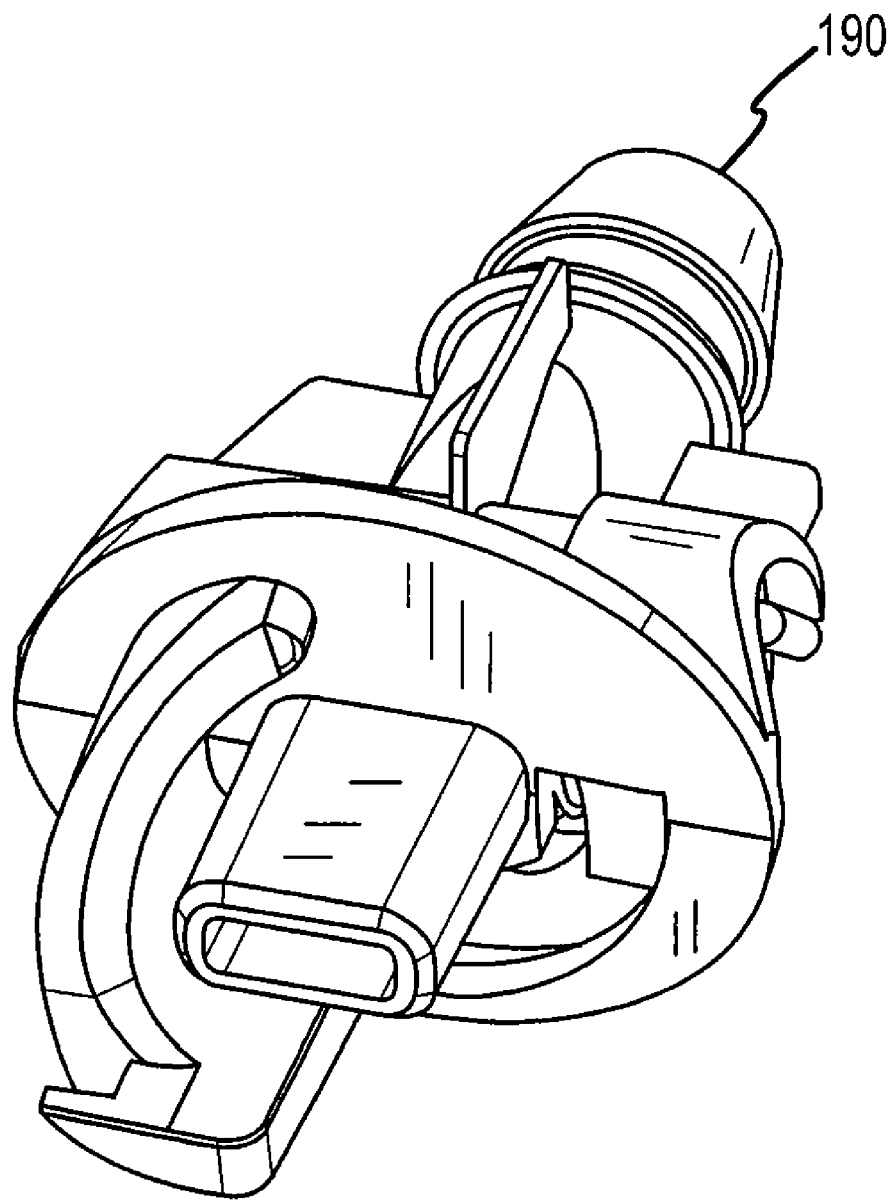
FIG. 7 is the same view of the male barrel depicted in FIG. 6, except the barbed end has been removed from the male barrel.
Figure 8:
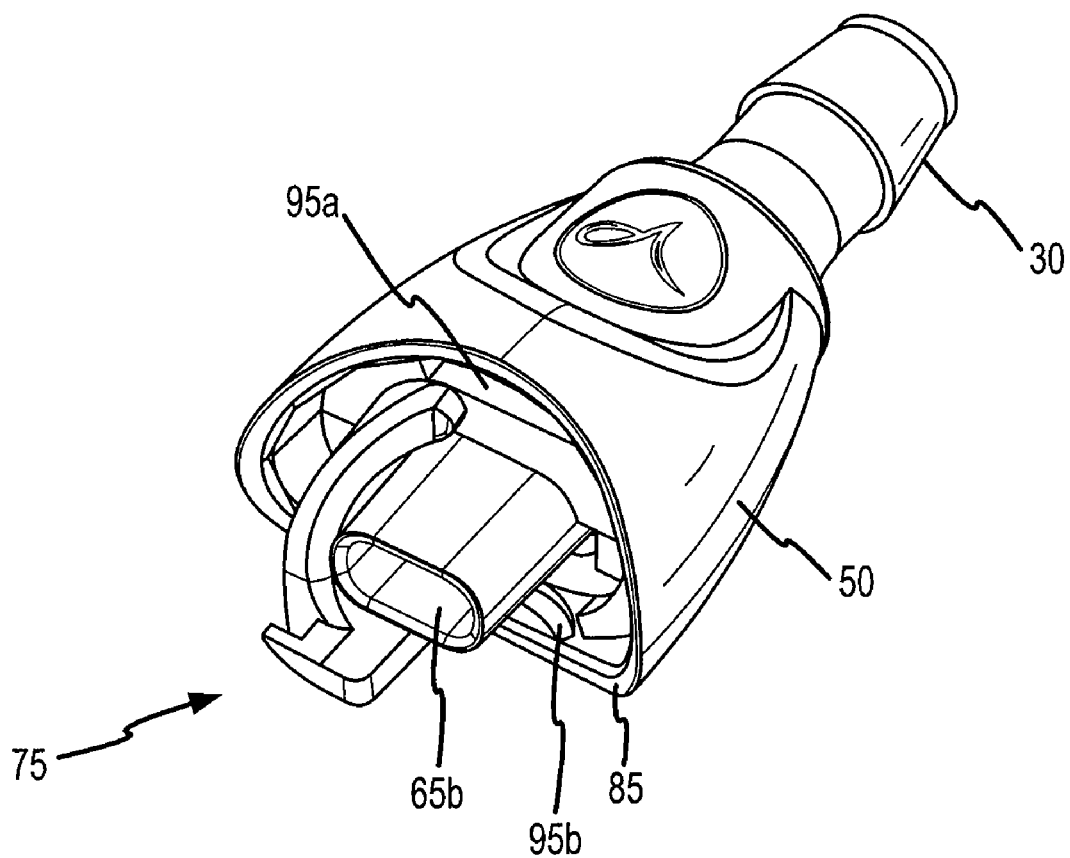
FIG. 8 is an isometric view of the female coupler as viewed from the joining side of the female coupler.
Figure 9:
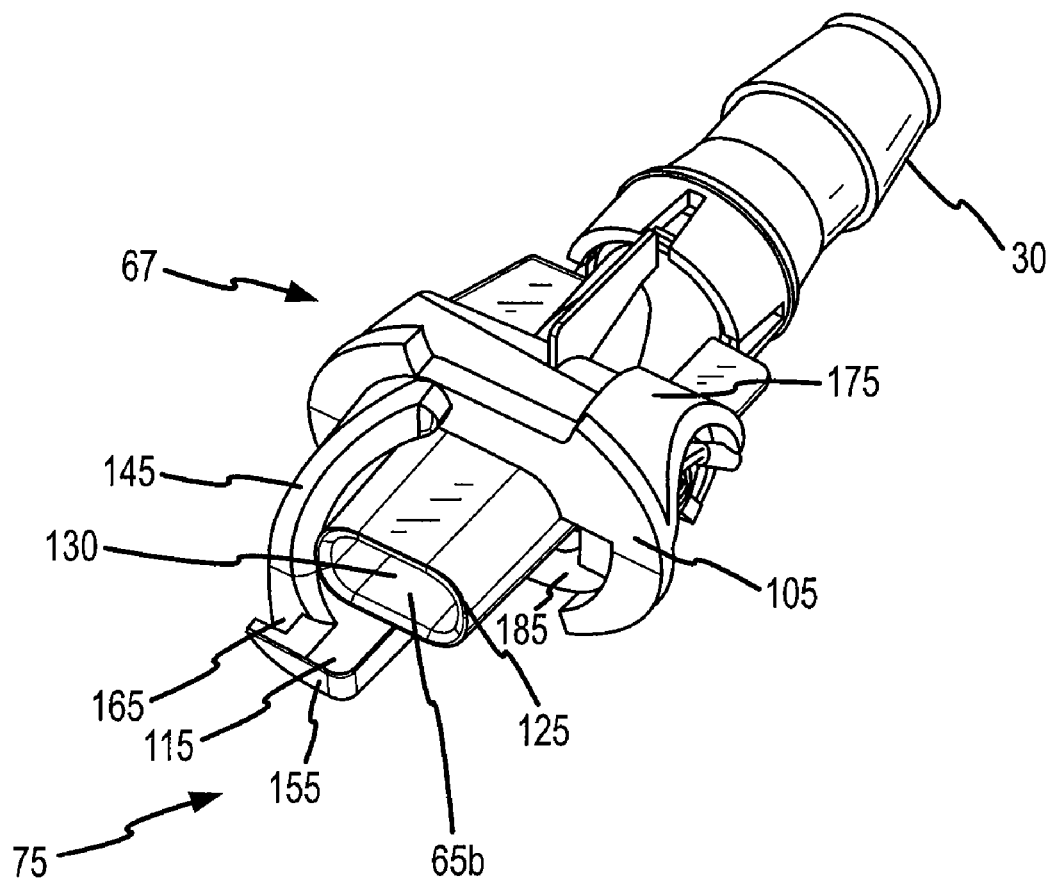
FIG. 9 is the same view of the female coupler depicted in FIG. 8, except the female coupler housing has been removed from the female coupler to reveal the female barrel.
Figure 10:
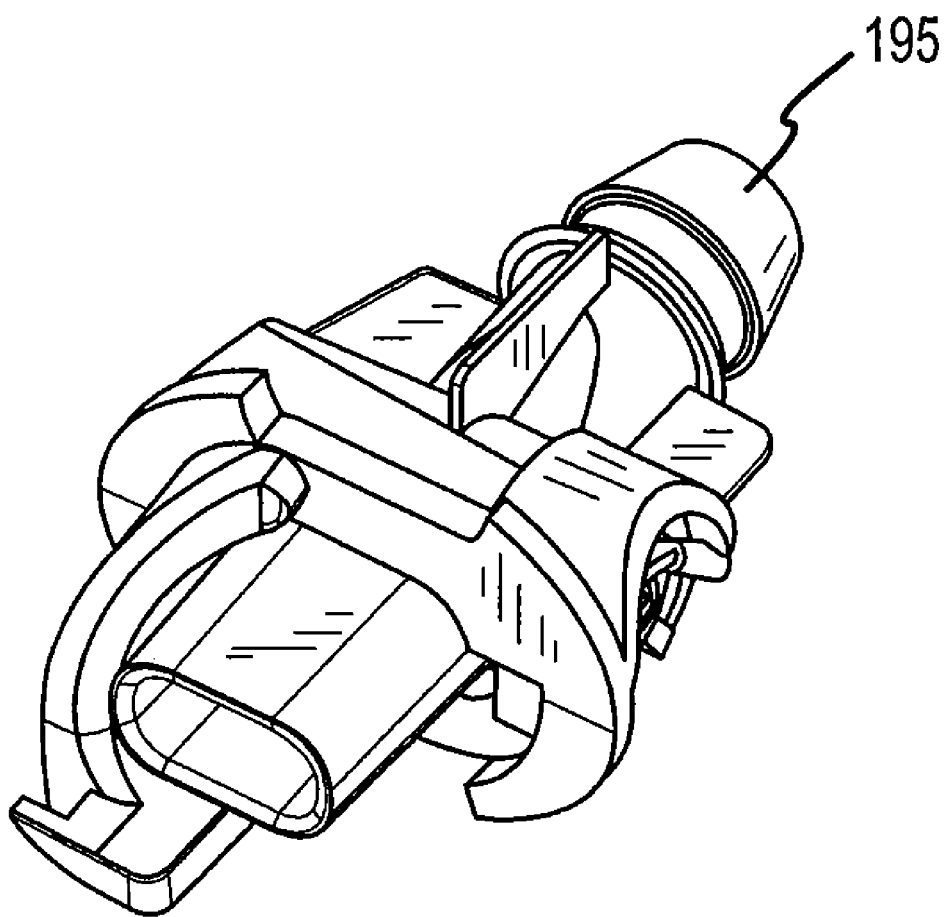
FIG. 10 is the same view of the female barrel depicted in FIG. 8, except the barbed end has been removed from the female barrel.

For a detailed discussion of the male coupler 15 and female coupler 20 as each coupler 15, 20 appears when disconnected from the other coupler 15, 20, reference is made to FIGS. 5-10. FIG. 5 is an isometric view of the male coupler 15 as viewed from the joining side of the male coupler 15. FIG. 6 is the same view of the male coupler 15 depicted in FIG. 5, except the male coupler housing 45 has been removed from the male coupler 15 to reveal the male barrel 66. FIG. 7 is the same view of the male barrel 66 depicted in FIG. 6, except the barbed end 25 has been removed from the male barrel 66. FIG. 8 is an isometric view of the female coupler 20 as viewed from the joining side of the female coupler 20. FIG. 9 is the same view of the female coupler 20 depicted in FIG. 8, except the female coupler housing 50 has been removed from the female coupler 20 to reveal the female barrel 67. FIG. 10 is the same view of the female barrel 67 depicted in FIG. 6, except the barbed end 30 has been removed from the female barrel 67.

As shown in FIGS. 5 and 8, the male and female couplers 15, 20 each have joining ends 70, 75 that mate with, and couple to, the joining end 70, 75 of the other coupler 15, 20. Each joining end 70, 75 includes a seam face 80, 85 that forms a leading surface of each housing 45, 50. When the couplers 15, 20 are connected together, as illustrated in FIGS. 1-3, the seam faces 80, 85 abut to form the seam 55.

As illustrated in FIGS. 5 and 8, the male housing 45 includes upper and lower engagement lips 90a, 90b that extend forwardly from the male housing 45 to engage with upper and lower engagement ridges 95a, 95b formed in the inner surface of the female housing 50. When the joining ends 70, 75 are pushed together in order connect the couplers 15, 20, the lips 90 and ridges 95 engage to maintain the couplers 15, 20 in a connected state. The lips 90 and ridges 95 form the previously mentioned engagement mechanism. The lips 90 are disengaged from the ridges 95 by pressing inward on the slots 60 and pulling the couplers 15, 20 longitudinally away from each other.

As indicated in FIGS. 6 and 9, the male and female couplers 15, 20 respectively include male and female barrels 66, 67 within the housings 45, 50. Each joining end 70, 75 of the male and female barrels 66, 67 includes a faceplate 100, 105, an arm or structural member 110, 115, and a neck 120, 125. Each neck 120, 125 protrudes forwardly from its respective faceplate 100, 105. The rectangular cross-sectioned fluid flow path 65b extends through the longitudinal center of each neck 120, 125. The fluid flow path 65b extends through the female neck 125 via a longitudinally extending orifice 130 that is sufficiently oversized to receive the outer circumferential surface 135 of the male neck 120 when the male neck 120 is plugged into the orifice 130 of the female neck 125. In one embodiment, the outer circumferential surface 135 of the male neck 120 and the orifice 130 of the female neck 125 are sufficiently close in size to form a fluid tight fit when the male neck 120 is plugged into the female neck 125. In one embodiment, an o-ring extends about the outer circumferential surface 135 of the male neck 120 to provide a fluid tight fit when the male neck 120 is received within the orifice 130 of the female neck 125.

As depicted in FIGS. 6 and 9, each structural member 110, 115 extends forwardly from its respective faceplate 100, 105. In one embodiment, each structural member 110, 115 includes an arcuate portion 140, 145 that arcuately sweeps from the faceplate 100, 105 to a point near the tip 150, 155 of the structural member 110, 115. Each arcuate portion 140, 145 acts as an alignment key to achieve proper alignment between the male and female couplers 15, 20 when being coupled together. In one embodiment, each tip 150, 155 of a structural member 110, 115 includes a groove or slot 160, 165 for mating with a slot or groove on an extreme end of a lever arm of a valve as described later in this Detailed Description.

As shown in FIGS. 6 and 9, each barrel 66, 67 includes a valve 170, 175 located along the fluid flow path 65 between the barbed end 25, 30 and the neck 120, 125 of each barrel 66, 67. The valves 170, 175 will be discussed in greater detail later in this Detailed Description.

As illustrated in FIGS. 6 and 9, each faceplate 100, 105 includes an opening 180, 185. Each opening 180, 185 serves as a passage by which the structural member 110, 115 of the other barrel 66, 67 encounters a valve lever arm, as discussed in greater detail later in this Detailed Description.

As can be understood from a comparison between FIGS. 6, 9, 7 and 10, in one embodiment, the barbed ends 25, 30 are rotatable relative to the barrels 66, 67, yet sealable. The barbed ends 25, 30 friction fit onto sub-ends 190, 195. In one embodiment, each barbed end 25, 30 is formed from a generally hard and rigid material such as polycarbonate, polycarbonate blend, or other similar polymers, and each sub-end 190, 195 is formed from a generally soft, pliable and resilient material such as high density polyethylene ("HDPE"), acetale, or other similar polymers. This arrangement eliminates the need for an o-ring to form fluid tight connections between the barbed ends 25, 30 and the sub-ends 190, 195. In other embodiments, the barbed ends 25, 30 and sub-ends 190, 195 are formed from the same hard and rigid material such as polycarbonate, polycarbonate blend, or other similar polymers and are provided with one or more o-rings to create fluid tight connections between the barbed ends 25, 30 and the sub-ends 190, 195. In either case, having a configuration with barbed ends 25, 30 that are rotatable relative to the sub-ends 190, 195, yet sealable with the sub-ends 190, 195, allows a fluid conduit 35, 40 to pivot/rotate about the longitudinal axis of a sub-end 190, 195 without jeopardizing the sealed connection between the fluid conduit 35, 40 and its respective coupler 15, 20.

In one embodiment, the barbed ends 25, 30 are an integral formed as part of the barrels 66, 67 such that there are no sub-ends 190, 195. As a result, the barbed ends 25, 30 are not removable from the barrels 66, 67.

Figure 11:
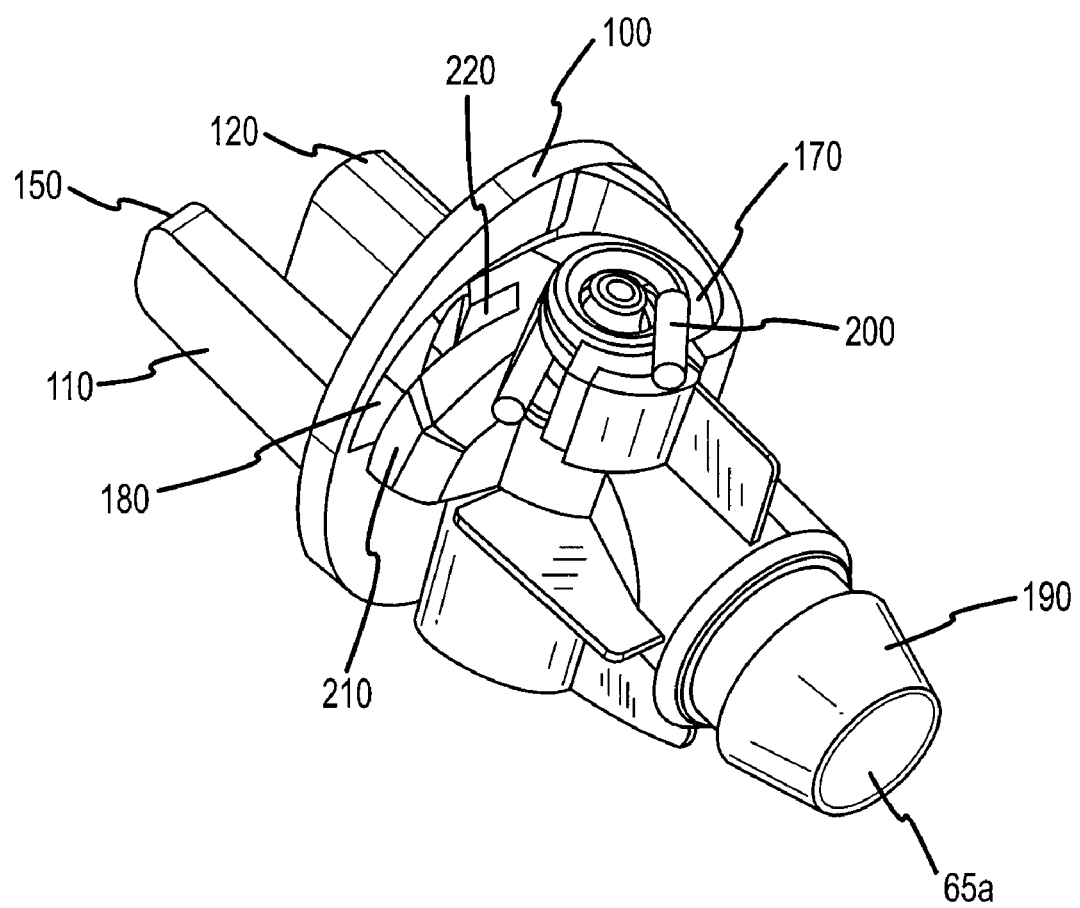
FIG. 11 is an isometric view of the male barrel as viewed from the fluid conduit connecting side of the male barrel.
Figure 12:
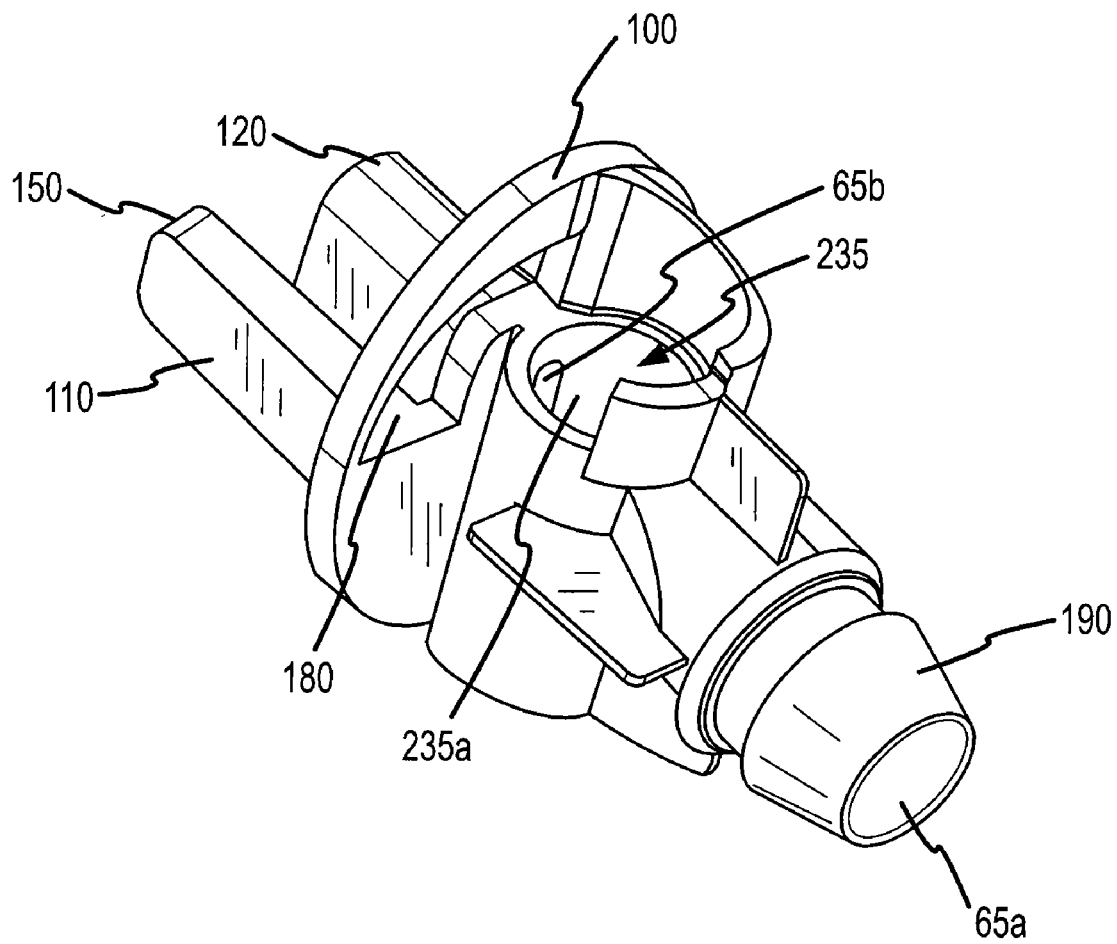
FIG. 12 is the same view of the male barrel depicted in FIG. 1, except the valve has been removed from the male barrel.
Figure 13:
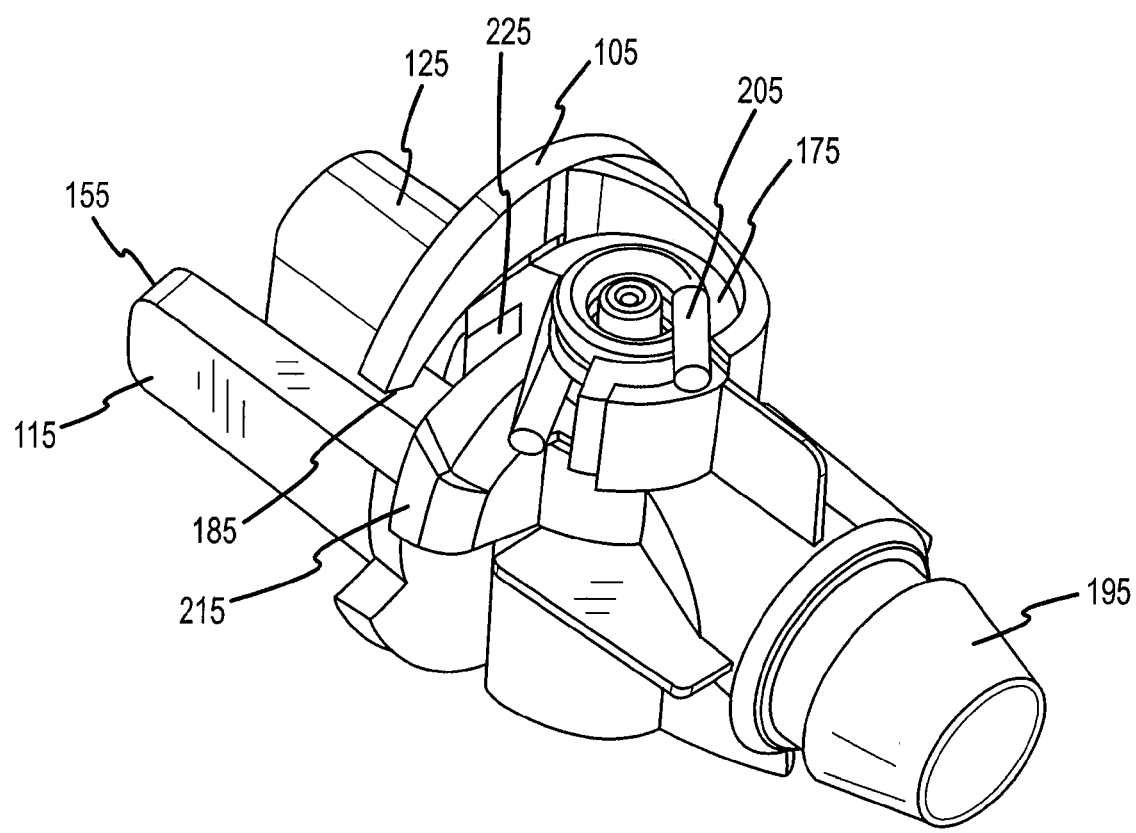
FIG. 13 is an isometric view of the female barrel as viewed from the fluid conduit connecting side of the female barrel.
Figure 14:
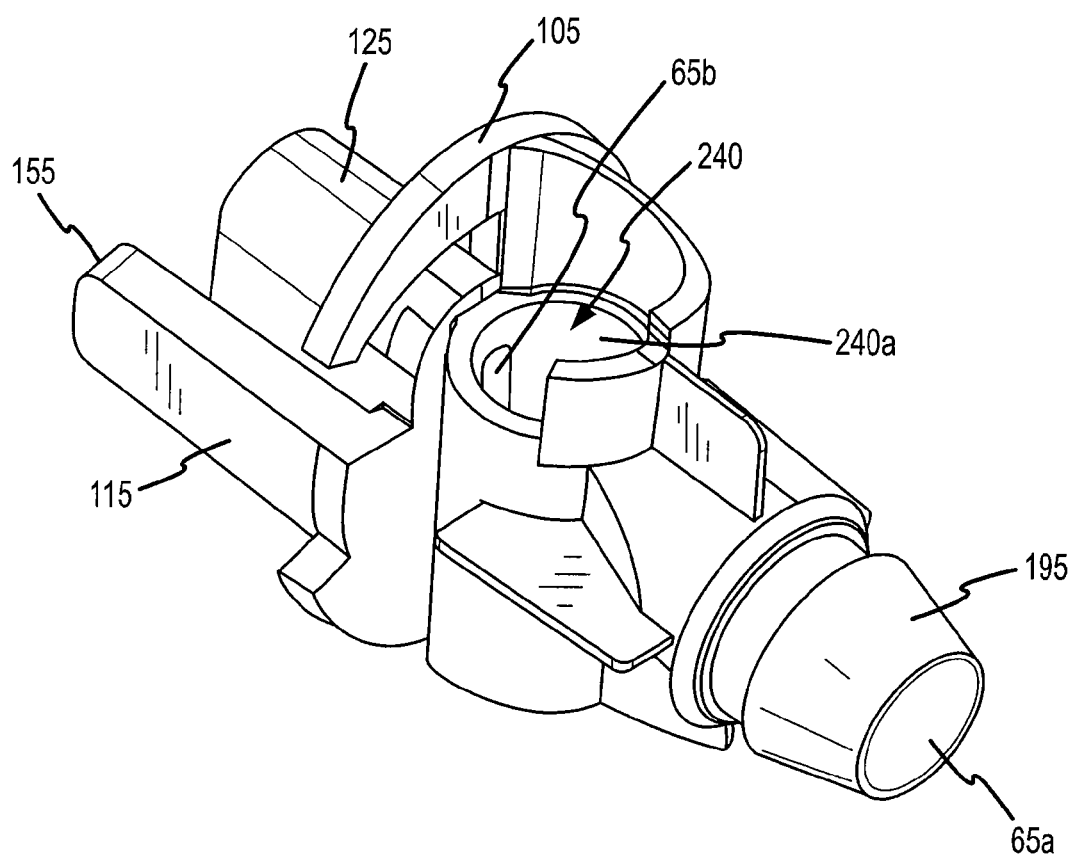
FIG. 14 is the same view of the female barrel depicted in FIG. 13, except the valve has been removed from the female barrel.
Figure 15:
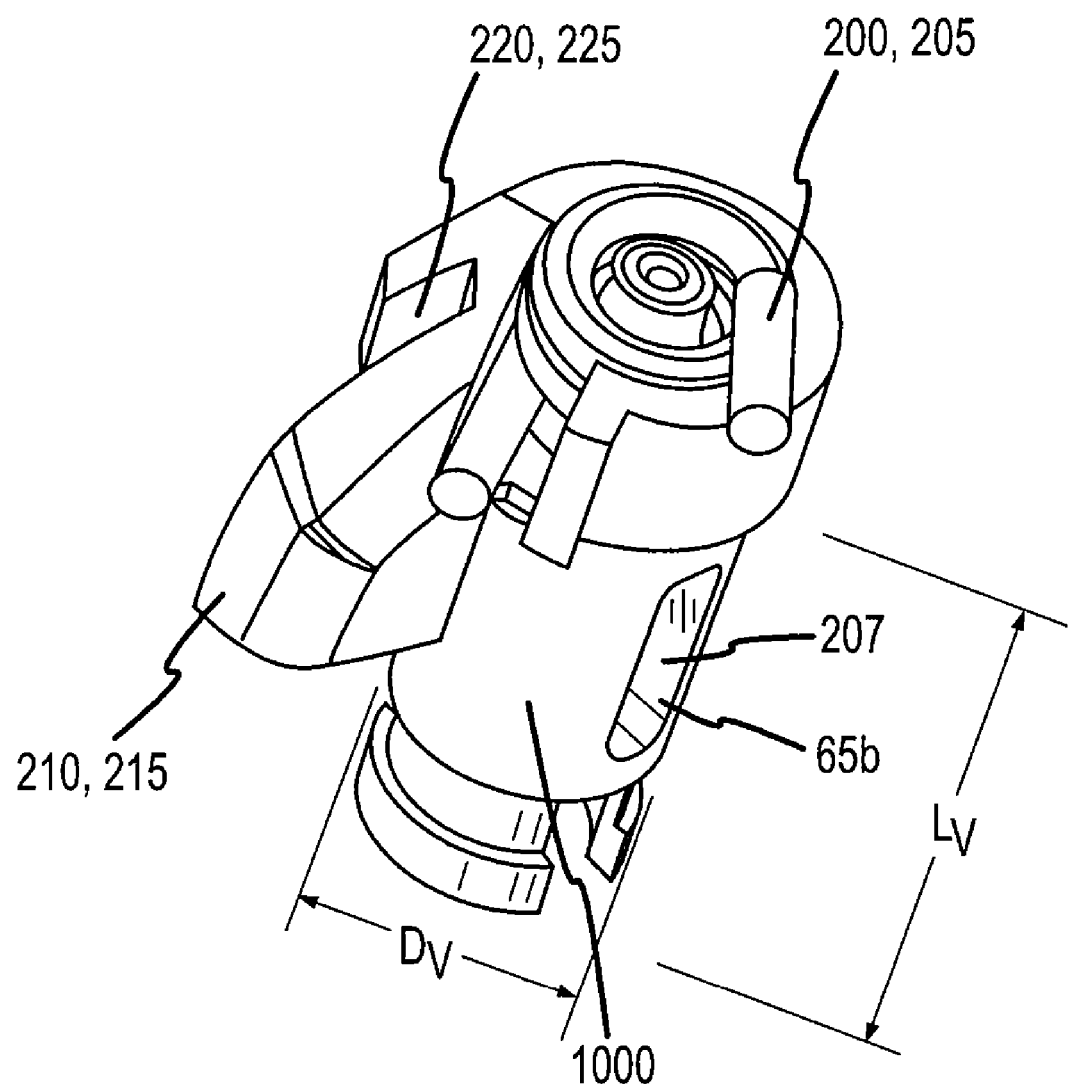
FIG. 15 is an isometric view of a valve and its biasing mechanism or spring as it would appear in FIG. 11 or 13 were the rest of the barrel removed from about the valve.
Figure 16:
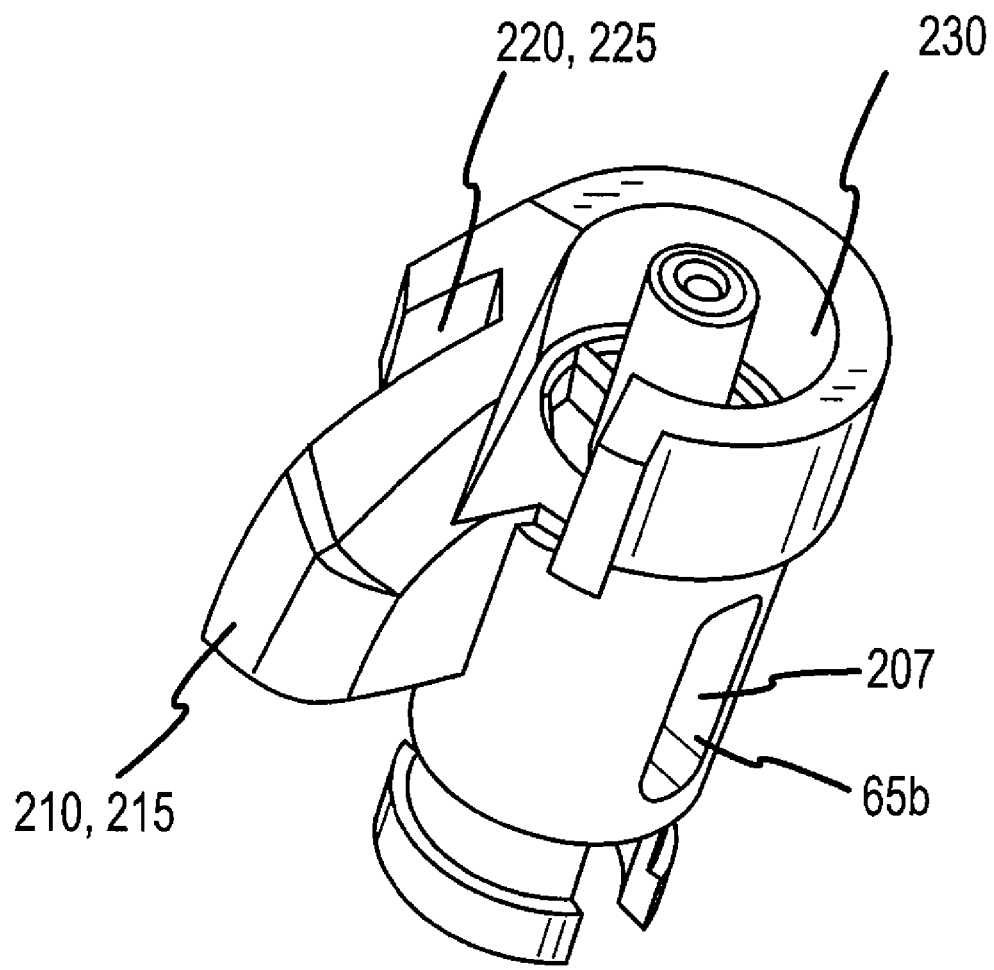
FIG. 16 is the same view of the valve depicted in FIG. 15, except the spring has been removed from the valve.

For a better understanding of the valve configuration of each barrel 66, 67, reference is made to FIGS. 11-16. FIG. 11 is an isometric view of the male barrel 66 as viewed from the fluid conduit connecting side of the male barrel 66. FIG. 12 is the same view of the male barrel 66 depicted in FIG. 11, except the valve 170 has been removed from the male barrel 66. FIG. 13 is an isometric view of the female barrel 67 as viewed from the fluid conduit connecting side of the female barrel 67. FIG. 14 is the same view of the female barrel 67 depicted in FIG. 13, except the valve 175 has been removed from the female barrel 67. FIG. 15 is an isometric view of a valve 170, 175 and its biasing mechanism or spring 200, 205 as it would appear in FIG. 11 or 13 were the rest of the barrel 66, 67 removed from about the valve 170, 175. FIG. 16 is the same view of the valve 170, 175 depicted in FIG. 15, except the spring 200, 205 has been removed from the valve 170, 175.

As indicated in FIGS. 11 and 13, each barrel 66, 67 includes a valve 170, 175 that is located between the back surface of the faceplate 100, 105 and the sub-end 190, 195. As shown in FIGS. 15 and 16, each valve 170, 175 has a cylindrical or barrel shaped body and includes a non-circular shaped orifice 207 that extends through the body of the valve 170, 175 perpendicular to the longitudinal axis of the body of the valve 170, 175. In one embodiment, the orifice 207 is rectangular and oriented such that its longitudinal axis coincides with the longitudinal axis of the body of the valve 170, 175. The orifice 207 serves as part of the rectangular cross-section fluid flow path 65b in each barrel 66, 67.

As shown in FIGS. 11, 13, 15 and 16, each valve 170, 175 includes a lever arm 210, 215 and a biasing mechanism or spring 200, 205. Each lever arm 210, 215 radially extends outward from the valve 170, 175 and includes a groove or slot 220, 225 that mates with the groove or slot 160, 165 in the tip 150, 155 of the structural member 110, 115 of the other barrel 66, 67, as will be discussed more fully later in this Detailed Description. Each biasing mechanism or spring 200, 205 acts between structural features of the valve 170, 175 and structural features of the barrel 66, 67 to bias the lever arm 210, 215 towards the opening 180, 185 in the faceplate 100, 105 immediately adjacent the valve 170, 175. In one embodiment, the biasing mechanism 200, 205 is a helical spring 200, 205 that resides within a cylindrical recess 230 in an end of the valve 170, 175.

As indicated in FIGS. 12 and 14, each barrel 66, 67 includes a cylindrical opening 235, 240 that receives therein the body of the valve 170, 175 and serves as a valve seat for the valve 170, 175. The rectangular cross-section fluid flow path 65b penetrates each cylindrical opening 235, 240 to form a pair of rectangular openings 65b in the inner circumferential surface 235a, 240a of the cylindrical opening 235, 240. Each valve 170, 175 is pivotally displaceable about its longitudinal axis within its cylindrical opening or valve seat 235, 240 of a barrel 66, 67.

As can be understood from FIGS. 11-16, when the valve 170, 175 pivotally is displaced within the valve seat 235, 240 of a barrel 66, 67 such that the valve's lever arm 210, 215 is displaced away from the faceplate 100, 105 of the barrel 66, 67, the rectangular orifice 207 extending through each valve 170, 175 aligns with the rectangular openings 65b in the inner circumferential surface 235a, 240a of the valve seat 235, 240. As a result, the fluid flow path 65 extends uninterrupted through the barrel 66, 67 from the sub-end 190, 195 to the neck 120, 125. Conversely, when the valve 170, 175 pivotally displaced within the valve seat 235, 240 of a barrel 66, 67 such that the valve's lever arm 210, 215 is displaced towards the faceplate 100, 105 of the barrel 66, 67, the rectangular orifice 207 extending through each valve 170, 175 does not coincide to any extent with the rectangular openings 65b in the inner circumferential surface 235a, 240a of the valve seat 235, 240. As a result, the fluid flow path 65 is sealed off or interrupted at the location of the valve 170, 175.

Figure 17:
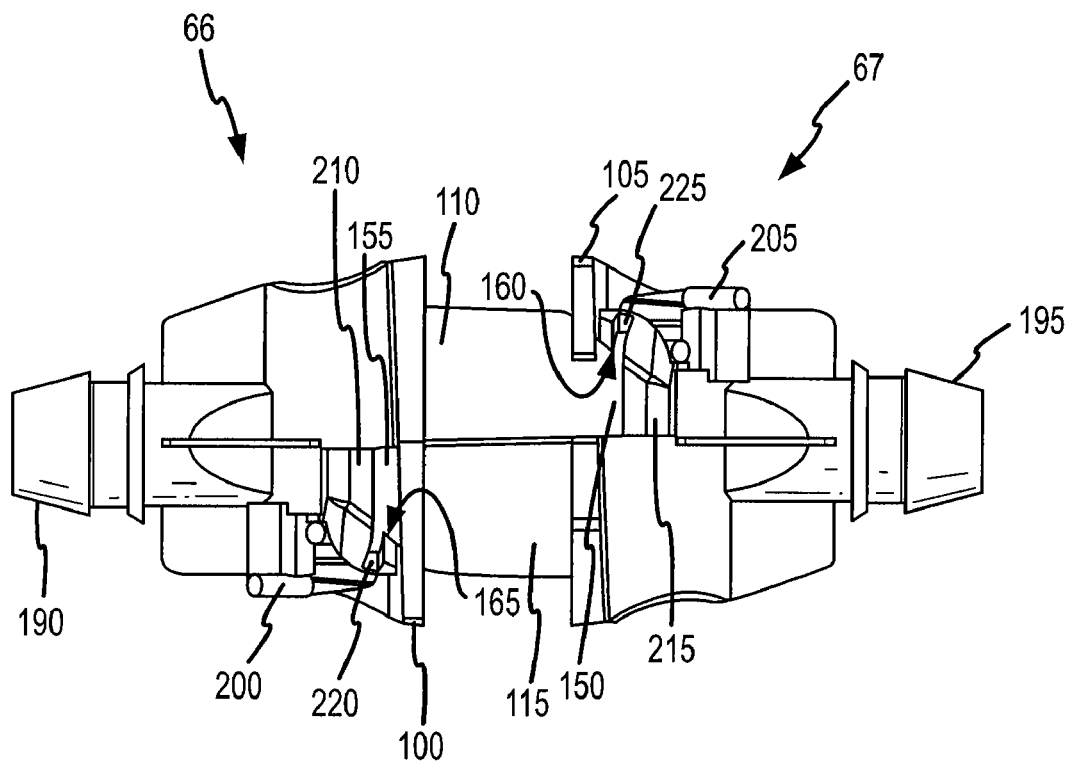
FIG. 17 is the same top plan of the coupling assembly as depicted in FIG. 2 and wherein the coupling assembly is in a connected state, except the housings and barbed ends have been removed to show the barrels.
Figure 18:
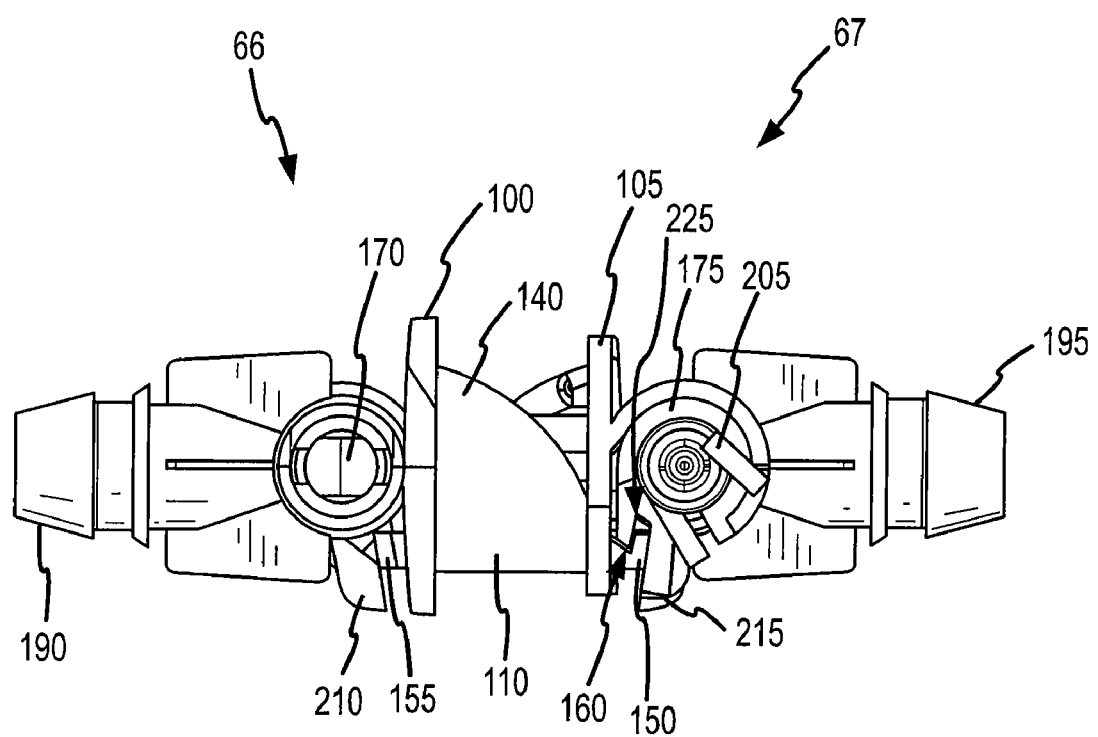
FIG. 18 is a side elevation of the barrels in the same connected state depicted in FIG. 17.
Figure 19:
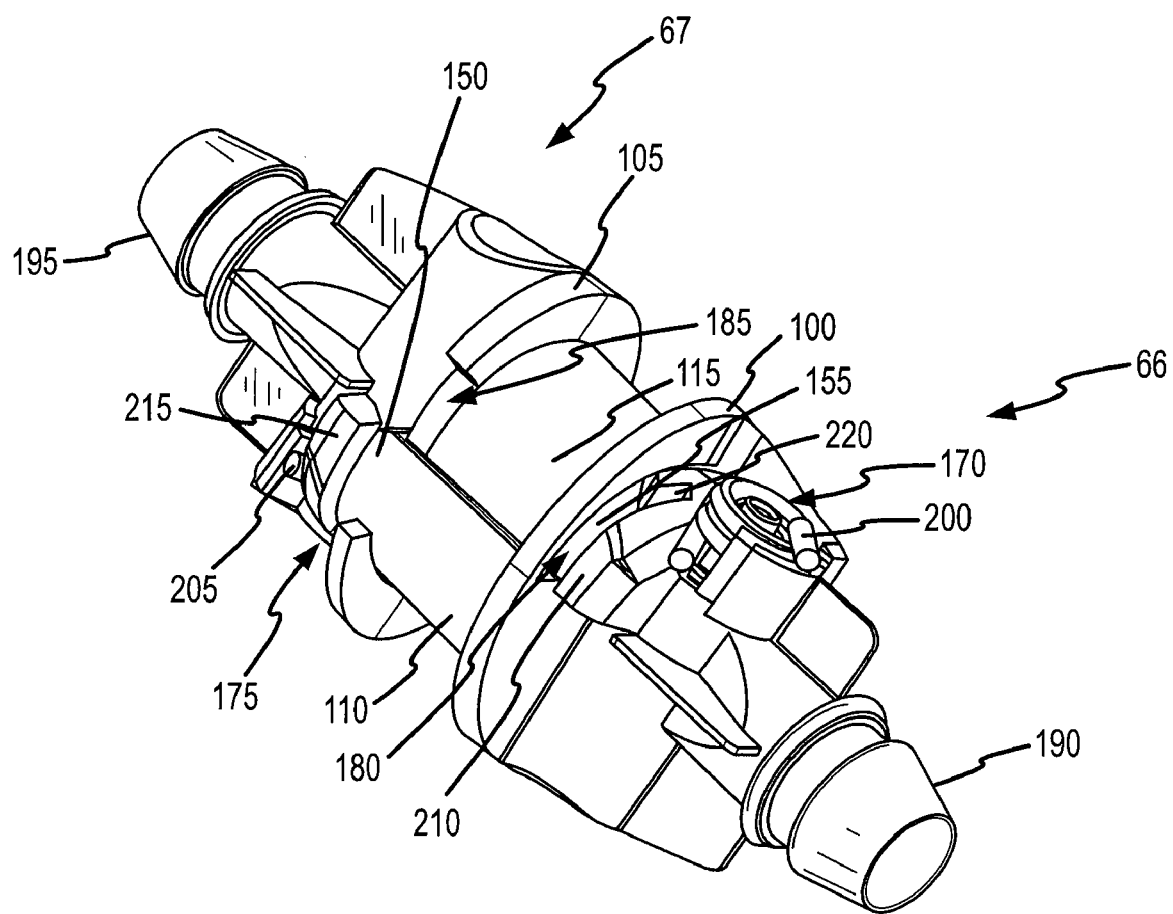
FIG. 19 is an isometric view of the barrels in the same connected state depicted in FIG. 17.
Figure 20:
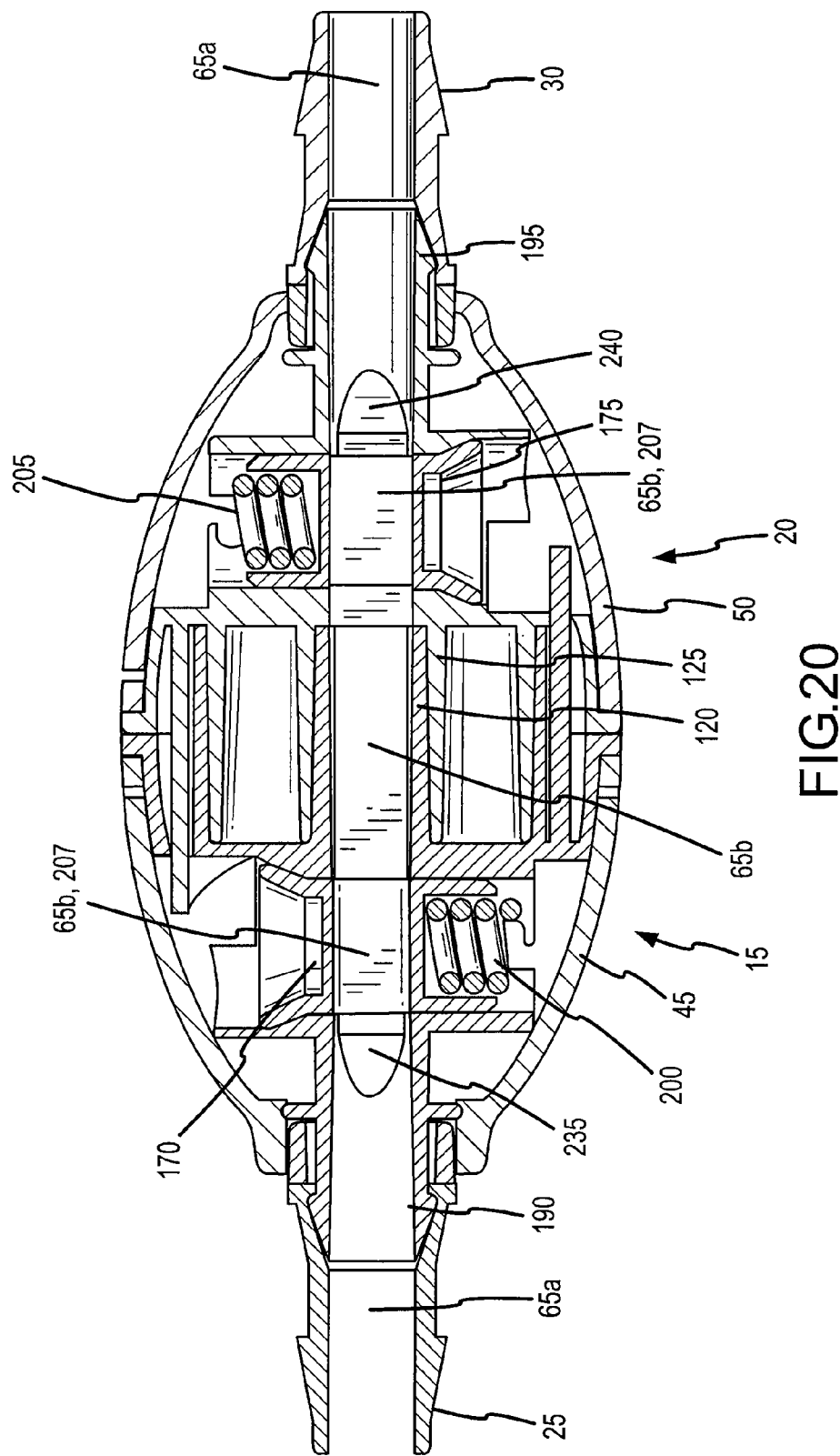
FIG. 20 is a cross-sectional top plan of the coupling assembly in a connected state as taken along section line 20-20 in FIG. 3.

For a better understanding of the interaction of the various components of the quick disconnect coupling assembly 10 when the male and female couplers 15, 20 are connected as illustrated in FIGS. 1-3, reference is made to FIGS. 17-19. FIG. 17 is the same top plan of the coupling assembly 10 as depicted in FIG. 2 and wherein the coupling assembly 10 is in a connected state, except the housings 45, 50 and barbed ends 25, 30 have been removed to show the barrels 66, 67. FIG. 18 is a side elevation of the barrels 66, 67 in the same connected state depicted in FIG. 17. FIG. 19 is an isometric view of the barrels 66, 67 in the same connected state depicted in FIG. 17. FIG. 20 is a cross-sectional top plan of the coupling assembly 10 in a connected state as taken along section line 20-20 in FIG. 3.

As can be understood from FIGS. 1-3, 5, 8 and 17-20, when the joining ends 70, 75 of the male and female couplers 15, 20 are pressed together, the male neck 120 is received within the orifice 130 of the female neck 125 to place the rectangular cross-section fluid flow path 65b of the male coupler 15 into fluid communication with the rectangular cross-section fluid flow path 65b of the female coupler. At the same time, the structural member 110 of the male barrel 66 passes through the faceplate opening 185 of the female barrel 67 to push the valve lever arm 215 of the female barrel 67 away from the faceplate 105 of the female barrel 67, and the structural member 115 of the female barrel 67 passes through the faceplate opening 180 of the male barrel 66 to push the valve lever arm 210 of the male barrel 66 away from the faceplate 100 of the male barrel 66. As a result, each valve 170, 175 pivots within its respective valve seat 235, 240 such that each rectangular valve orifice 207 aligns with the rectangular fluid flow paths 65b extending through the barrels 66, 67. In other words, each valve 170, 175 pivots from a closed position to an open position wherein the fluid flow path 65 extends in an uninterrupted path through the coupling assembly 10. As the structural members 110, 115 displace the valve lever arms 210, 215 such that the valves 170, 175 pivot towards the valve open position, the slot or groove 220, 225 on the end of each lever arm 210, 215 mates with the slot or groove 160, 165 on the tip 150, 155 of each structural member 110, 115. The mating of the slots or grooves 160, 165, 220, 225 locks the lever arms 210, 215 to the structural members 110, 115, thereby locking the valves 170, 175 pivotally in the open position. As previously discussed, the engagement mechanism 90, 95 on the male and female housings 45, 50 engage to maintain the couplers 15, 20 in the connected state depicted in FIGS. 1-3, 5, 8 and 17-20.

As shown in FIG. 20, when the couplers 15, 20 are connected together as depicted in FIGS. 1-3 and 17-19, the fluid flow path 65 extends uninterrupted through the coupling assembly 10 from the male barbed end 25 to the female barbed end 30. In one embodiment, as depicted in FIG. 20, the fluid flow path 65 transitions from a circular cross-section fluid flow path 65a to a rectangular cross-section fluid flow path 65b at fluid flow path transitions 235, 240 located at the following locations: (1) between the male barbed end 25 and the male valve 170; and between the female barbed end 30 and the female valve 175. As a result, in one embodiment, the rectangular cross-section fluid flow path 65b extends in a continuous non-varying path through the orifices 207 of each valve and the distance between the transitions 235, 240 including the necks 120, 125 of the male and female barrels 66, 67.

As can be understood from FIGS. 1-3, 5, 8 and 17-20, by pressing on the slots 60 on the outer surface of the male housing 45, the engagement mechanism 90, 95 is disengaged. With the engagement mechanism 90, 95 disengaged, the couplers 15, 20 are longitudinally displaced away from each other, which causes the male neck 120 to withdraw from within the orifice 130 of the female neck 125 and the structural members 110, 115 to pull away from the lever arms 210, 215 and withdraw from the faceplate openings 180, 185. As a result, each valve 170, 175 is biased via its respective spring 200, 205 to pivot to the closed position wherein the end of each valve lever arm 210, 215 resides near the faceplate 100, 105 and no portion of the each valve orifice 207 coincides with the rectangular fluid flow path 65b extending through each barrel 66, 67. Consequently, the valves 170, 175 automatically seal closed the fluid flow path 65 in each coupler 15, 20.

b. Second Embodiment of the Quick Disconnect Coupling Assembly

Figure 21:
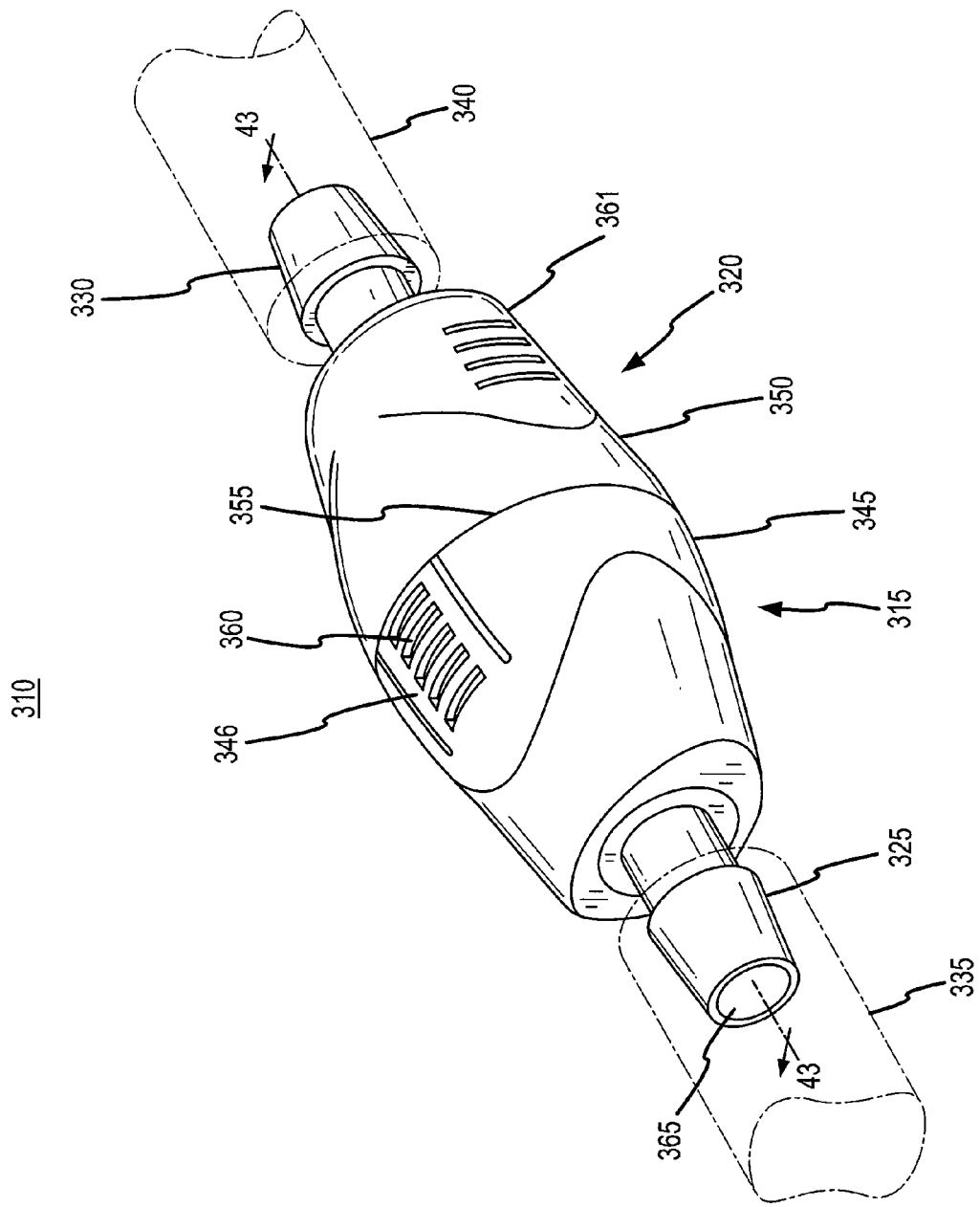
FIG. 21 is an isometric view of the quick disconnect coupling assembly, wherein the male coupler and female coupler are connected.

For a discussion of the second embodiment of the quick disconnect coupling assembly 310 of the present invention, reference is made to FIGS. 21-25. FIG. 21 is an isometric view of the quick disconnect coupling assembly 310, wherein the male coupler 315 and female coupler 320 are connected.

Figure 22:
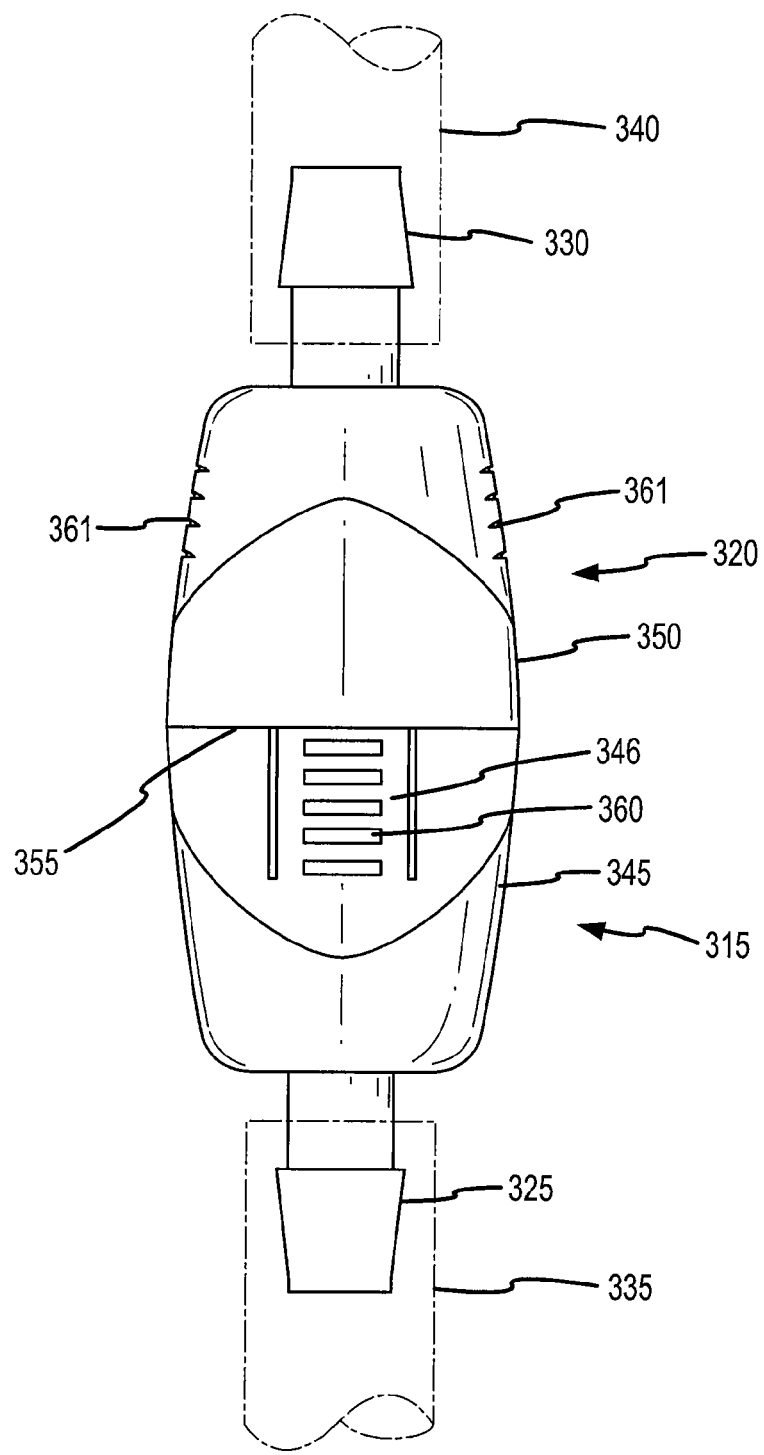
FIG. 22 is a top plan of the coupling assembly in the same connected state as depicted in FIG. 21.
Figure 23:
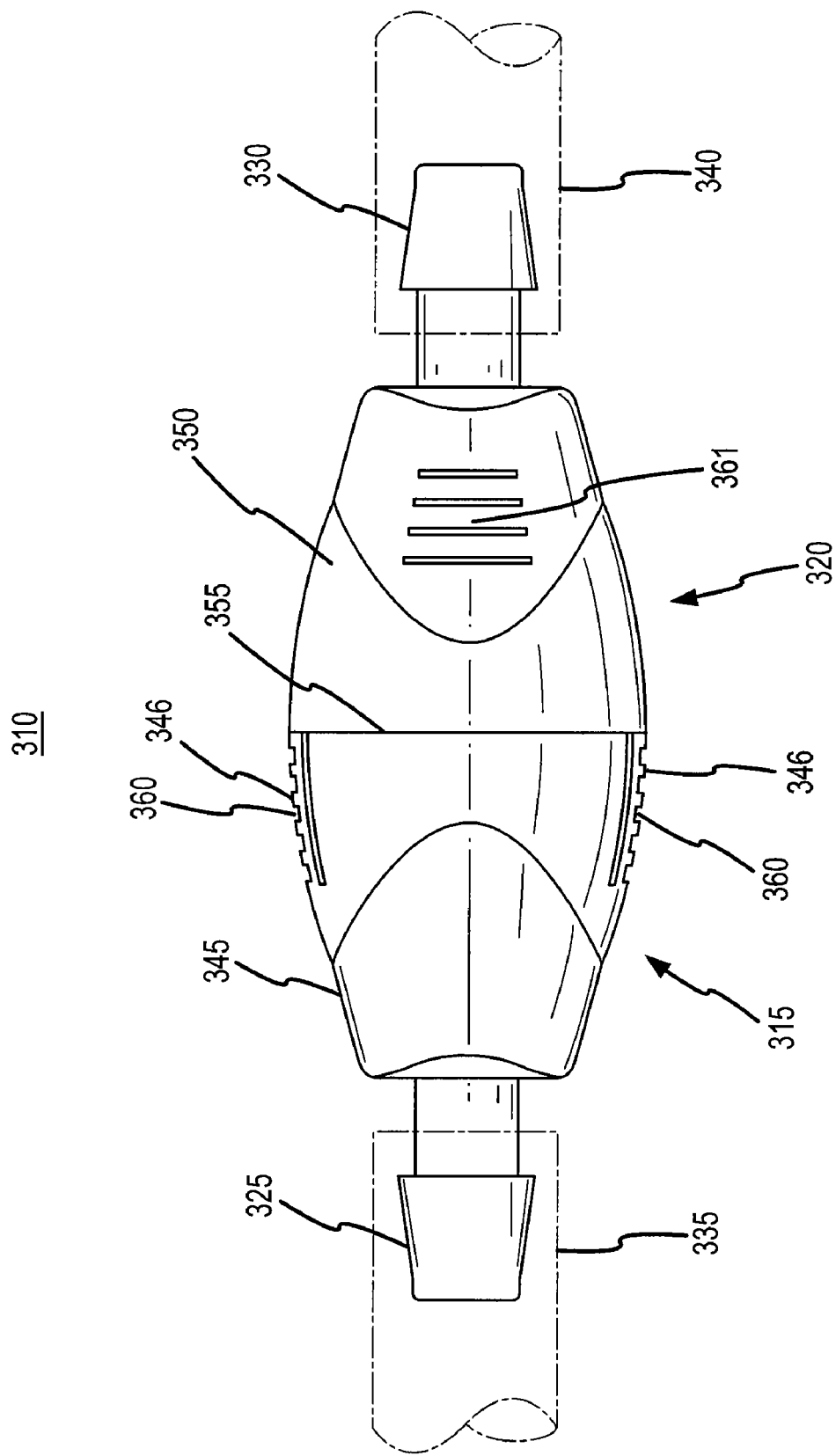
FIG. 23 is a side elevation of the coupling assembly in the same connected state depicted in FIG. 21.
Figure 24:
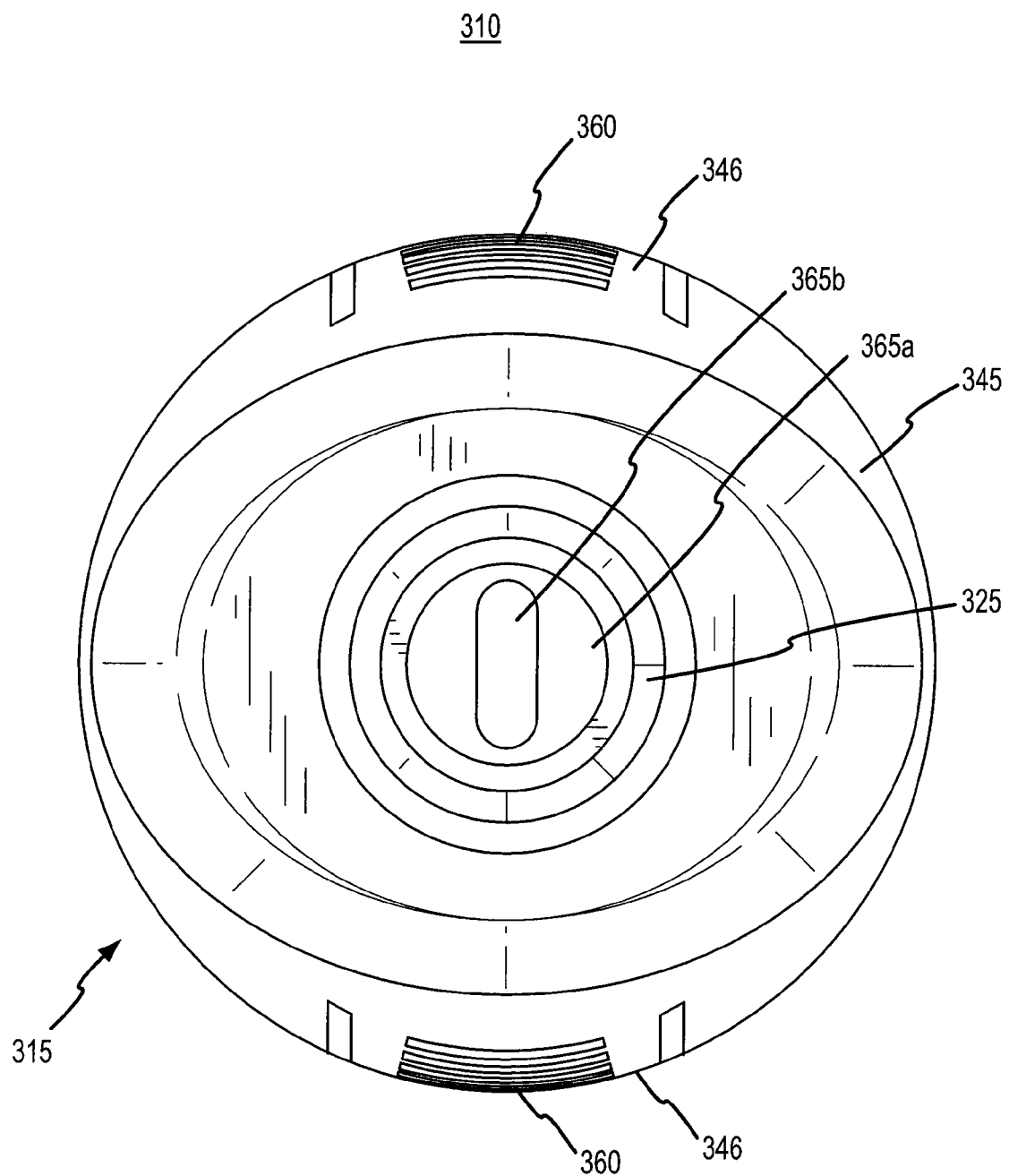
FIG. 24 is an end elevation of the coupling assembly in the same connected state depicted in FIG. 21 and as viewed from the male coupler end.
Figure 25:
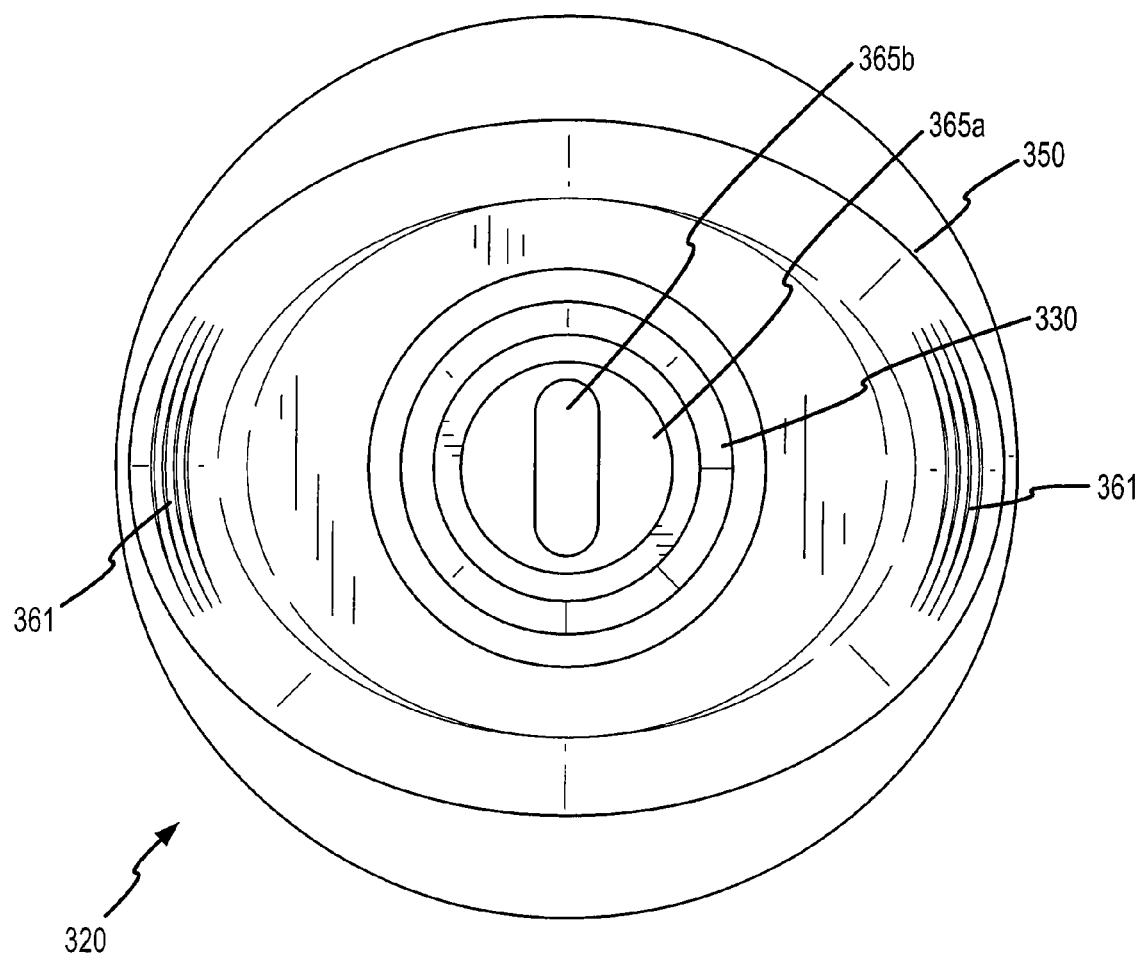
FIG. 25 is an end elevation of the coupling assembly in the same connected state depicted in FIG. 21 and as viewed from the female coupler end.

FIG. 22 is a top plan of the coupling assembly 310 in the same connected state as depicted in FIG. 21. While a bottom plan of the coupling assembly 310 is not provided, it should be understood that it would appear identical to the view depicted in FIG. 22. FIG. 23 is a side elevation of the coupling assembly 310 in the same connected state depicted in FIG. 21. While a view of the opposite side of the coupling assembly 310 is not provided, it should be understood that it would appear identical to the view depicted in FIG. 23. FIG. 24 is an end elevation of the coupling assembly 310 in the same connected state depicted in FIG. 21 and as viewed from the male coupler end. FIG. 25 is an end elevation of the coupling assembly 310 in the same connected state depicted in FIG. 21 and as viewed from the female coupler end.

As shown in FIG. 21-23, the quick disconnect coupling assembly 310 includes a male coupler 315 and a female coupler 320. Each coupler 315, 320 includes a barbed end 325, 330 for insertion into, and connection with, a fluid conduit 335, 340 such as medical grade flexible tubing. Each coupler 315, 320 includes a housing or shroud 345, 350 that forms the exterior shell of each coupler 315, 320. When the couplers 315, 320 are connected, as depicted in FIGS. 21-23, the housings 345, 350 form a body that is semi-elliptical or egg-shaped as viewed from above, below or from the sides, as shown in FIGS. 22 and 23.

When the couplers 315, 320 are connected, the joining ends of the housings 345, 350 of the coupler 315, 320 abut along a seam 355 that circumferentially latitudinally extends about the exterior shell of the coupling assembly 310. The male coupling housing 345 includes a pair of buttons 346 that are pressed inward to disengage an engagement mechanism (shown in later figures) that holds the couplers 315, 320 together. A group of latitudinal extending slots 360 are located on each button 346 to provide friction contact points for a user's fingers when pressing on the button to disengage the engagement mechanism. Additional groups of latitudinal slots 361 are also located on the female housing 350 to facilitate a user's grasp of the female coupler 320 when longitudinally pulling the couplers 315, 320 apart after having disengaged the engagement mechanism.

As can be understood from FIGS. 21, 24 and 25, a fluid flow path 365 extends through the coupler assembly 310 from the male coupler barbed end 325 to the female coupler barbed end 330. In one embodiment, as indicated in FIGS. 24 and 25, and as will be described with greater detail later in this Detailed Description, the fluid flow path 365 makes the following transitions as it extends through the coupler assembly from the male barbed end 325 to the female barbed end 330: circular cross-section 365a to a rectangular cross-section 365b to a circular cross-section 365a to a rectangular cross-section to a circular cross-section 365a.

Figure 26:
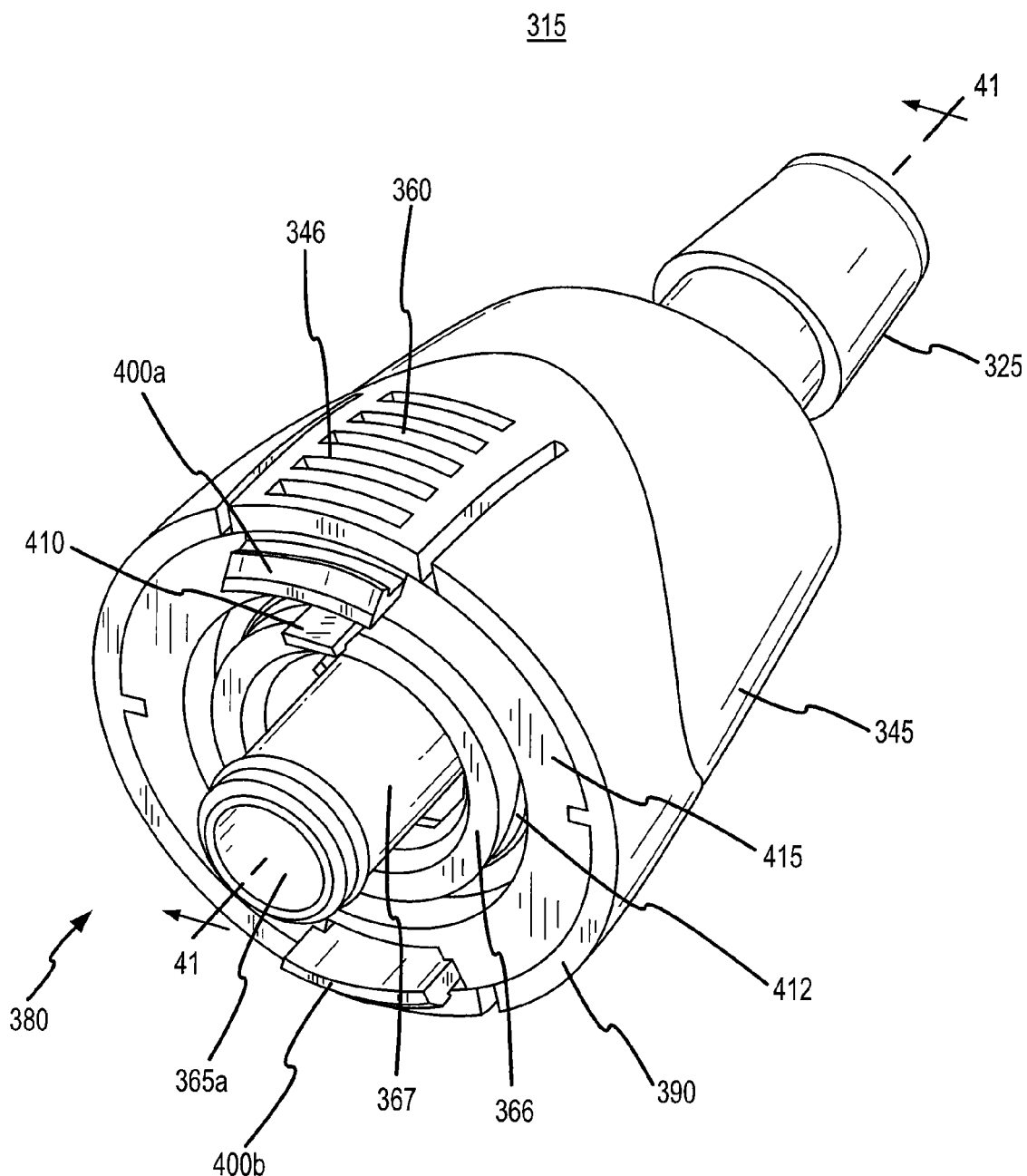
FIG. 26 is an isometric view of the male coupler as viewed from the joining side of the male coupler and indicating how a valve actuator of the male coupler would appear relative to a barrel of the male coupler when the male coupler is connected to the female coupler as illustrated in FIGS. 21-23.
Figure 27:
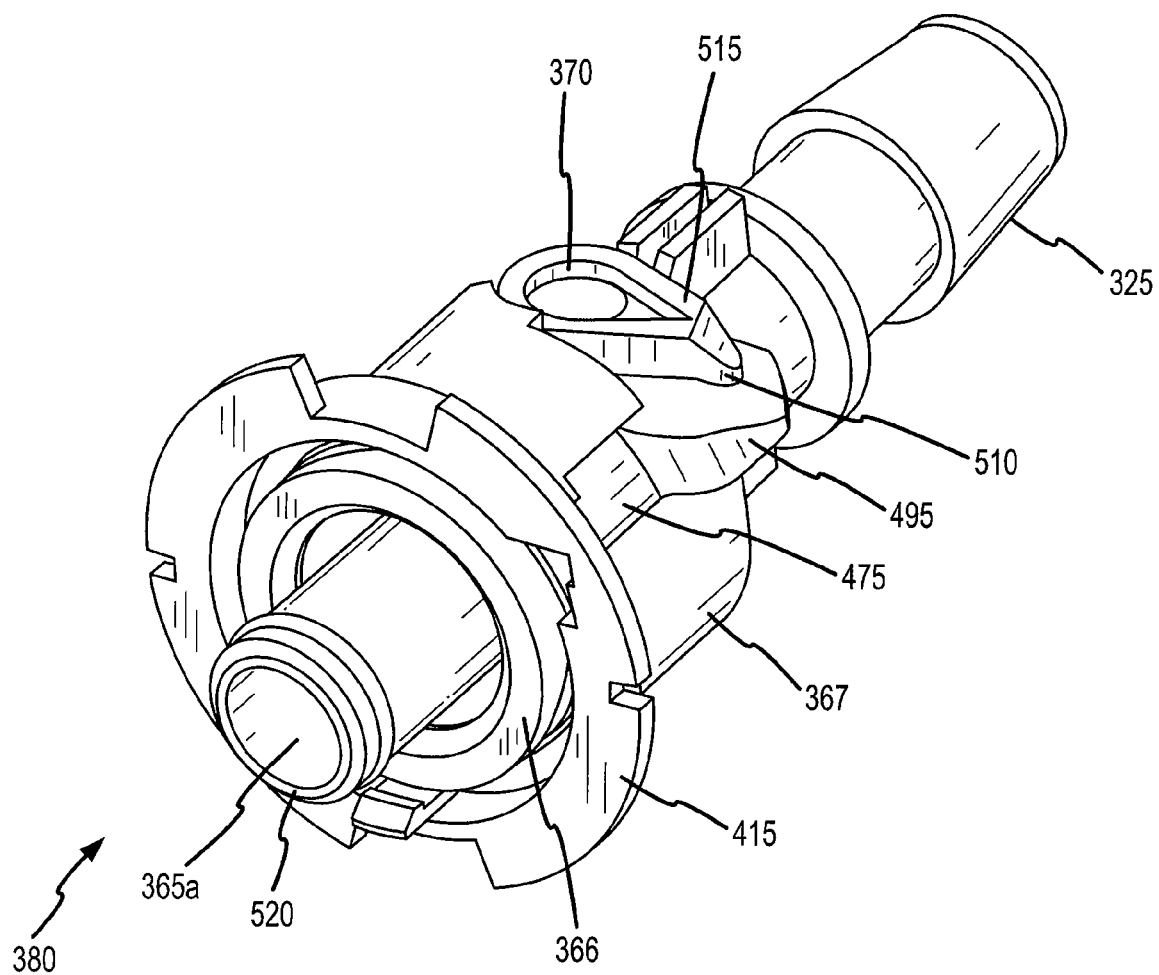
FIG. 27 is the same view of the male coupler depicted in FIG. 26, except the male coupler has been rotated about its longitudinal axis approximately 180 degrees to better depict its features and the male coupler housing has been removed from the male coupler to more fully reveal the male barrel.
Figure 28:
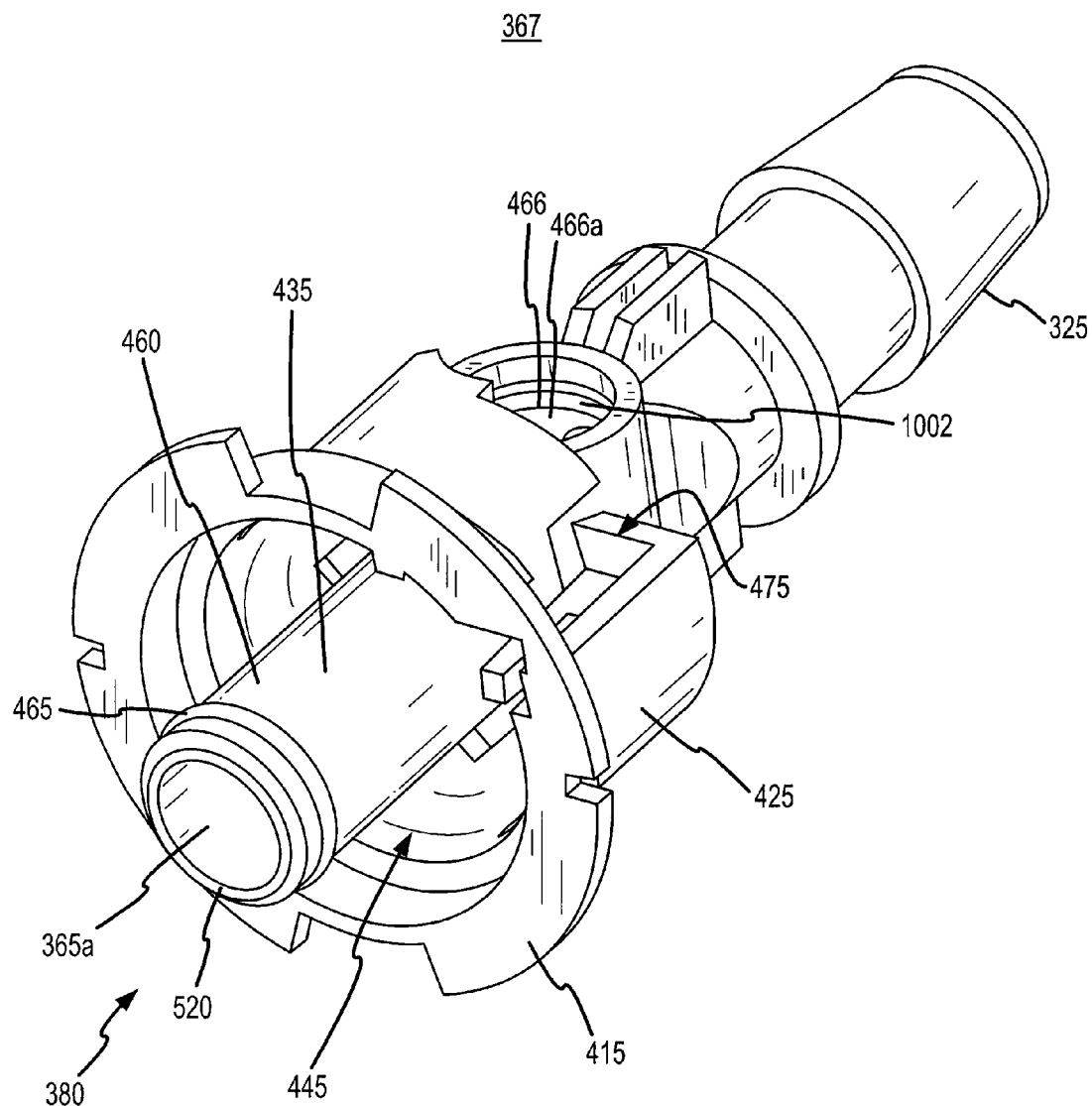
FIG. 28 is the same view of the male barrel depicted in FIG. 27, except the male valve actuator and the male valve have been removed from the male barrel to better illustrate its features.

For a detailed discussion of the elements of the male coupler 315 and female coupler 320, reference is made to FIGS. 26-33. FIG. 26 is an isometric view of the male coupler 315 as viewed from the joining side of the male coupler 315 and indicating how a valve actuator 366 of the male coupler 315 would appear relative to a barrel 367 of the male coupler 315 when the male coupler 315 is connected to the female coupler 320 as illustrated in FIGS. 21-23. FIG. 27 is the same view of the male coupler 315 depicted in FIG. 26, except the male coupler 315 has been rotated about its longitudinal axis approximately 180 degrees to better depict its features and the male coupler housing 345 has been removed from the male coupler 315 to more fully reveal the male barrel 367. FIG. 28 is the same view of the male barrel 367 depicted in FIG. 27, except the male valve actuator 366 and the male valve 370 have been removed from the male barrel 367 to better illustrate its features.

Figure 29:
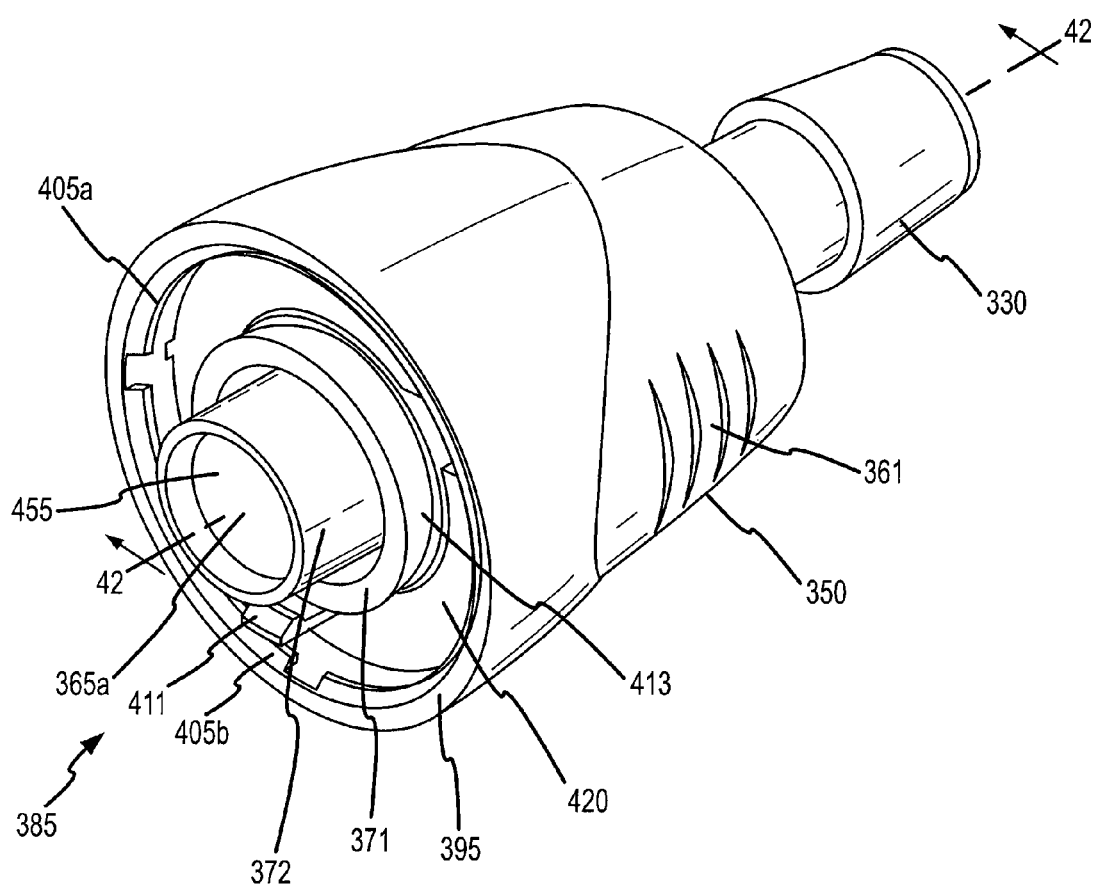
FIG. 29 is an isometric view of the female coupler as viewed from the joining side of the female coupler and indicating how a valve actuator of the female coupler would appear relative to a barrel of the female coupler when the female coupler is connected to the male coupler as illustrated in FIGS. 21-23.
Figure 30:
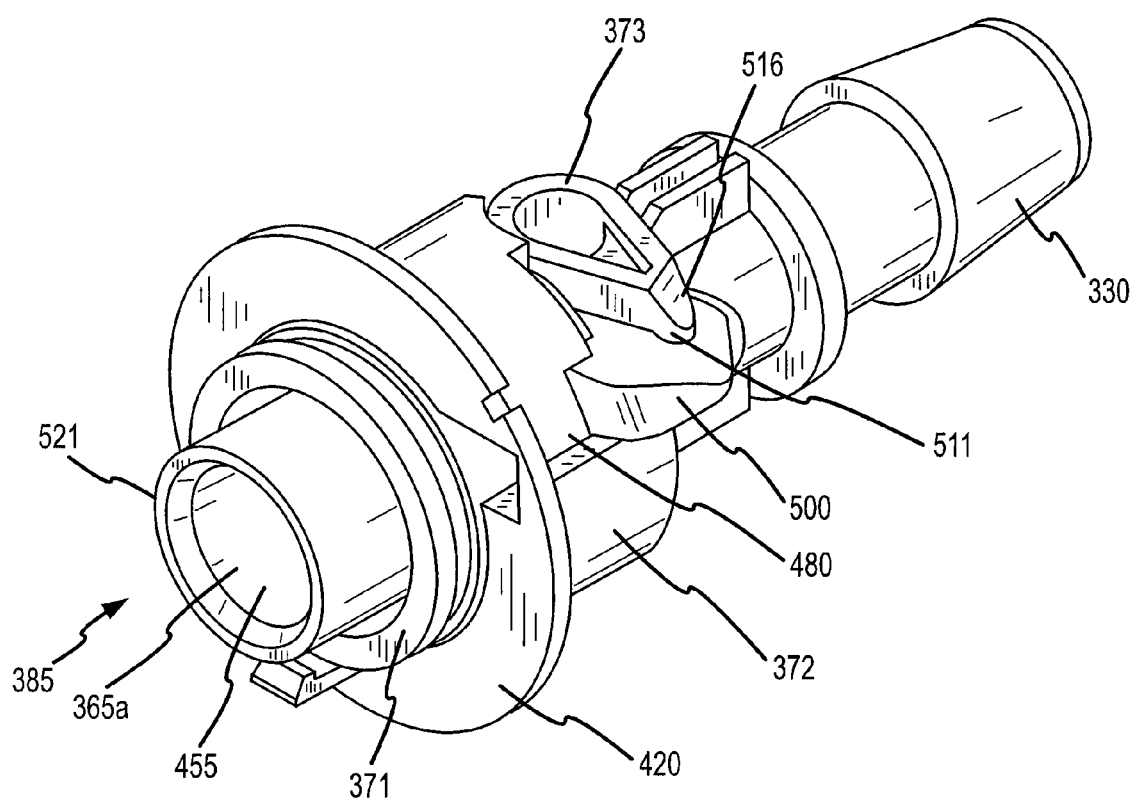
FIG. 30 is the same view of the female coupler depicted in FIG. 29, except the female coupler housing has been removed from the female coupler to more fully reveal the female barrel.
Figure 31:
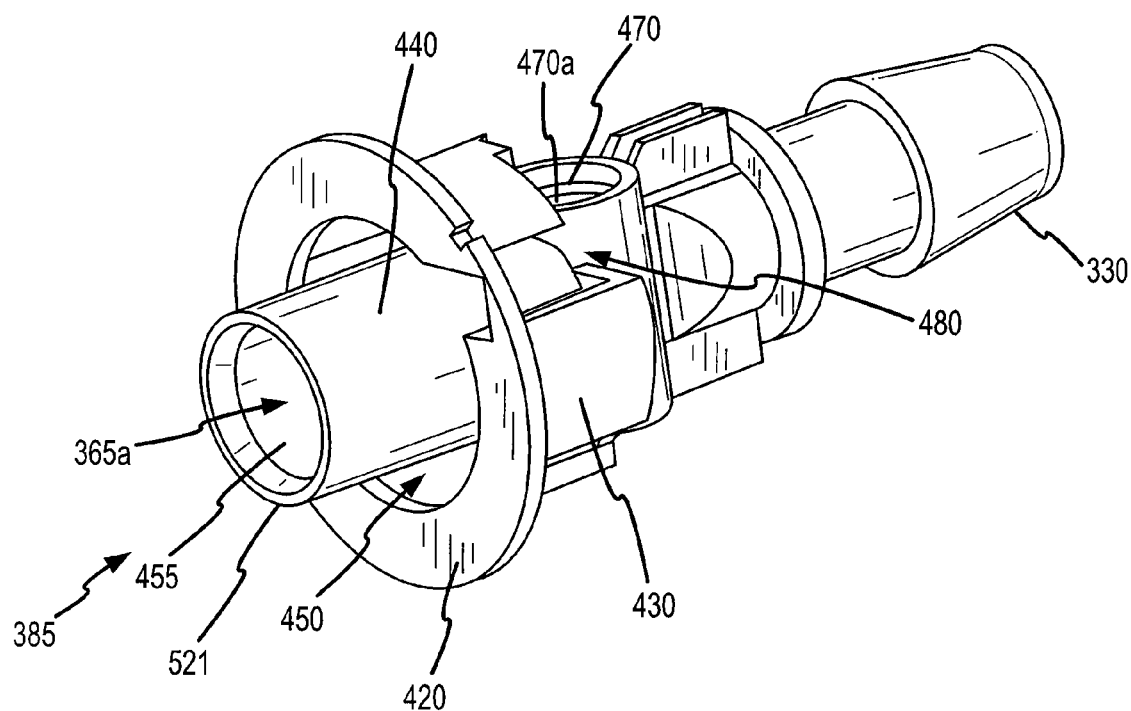
FIG. 31 is the same view of the female barrel depicted in FIG. 30, except the female valve actuator and the female valve have been removed from the female barrel to better illustrate its features.

FIG. 29 is an isometric view of the female coupler 320 as viewed from the joining side of the female coupler 320 and indicating how a valve actuator 371 of the female coupler 320 would appear relative to a barrel 372 of the female coupler 320 when the female coupler 320 is connected to the male coupler 315 as illustrated in FIGS. 21-23. FIG. 30 is the same view of the female coupler 320 depicted in FIG. 29, except the female coupler housing 350 has been removed from the female coupler 320 to more fully reveal the female barrel 372. FIG. 31 is the same view of the female barrel 372 depicted in FIG. 30, except the female valve actuator 371 and the female valve 373 have been removed from the female barrel 372 to better illustrate its features.

Figure 32:
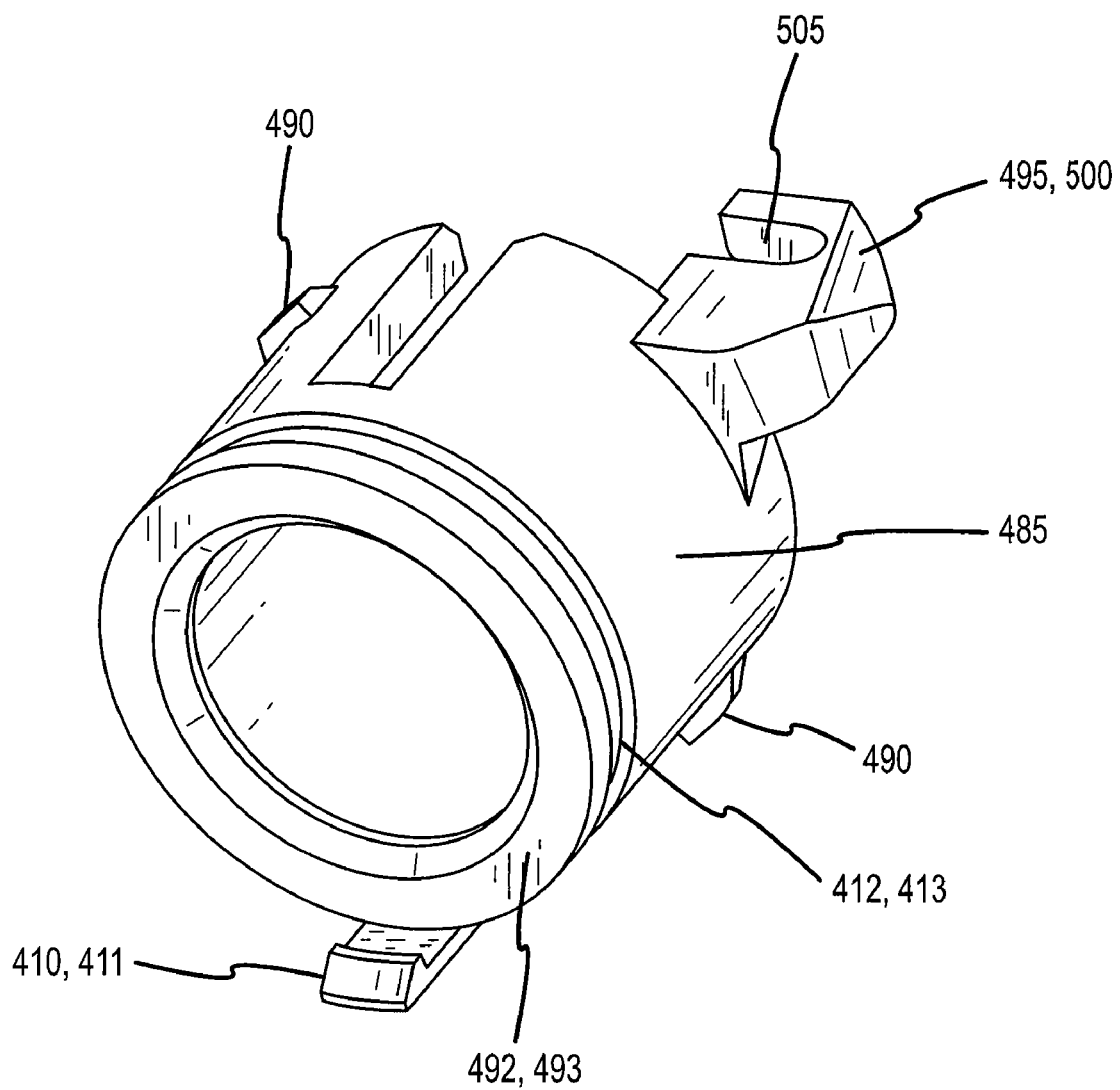
FIG. 32 is an isometric view of a valve actuator as employed in the male and female couplers.
Figure 32A:
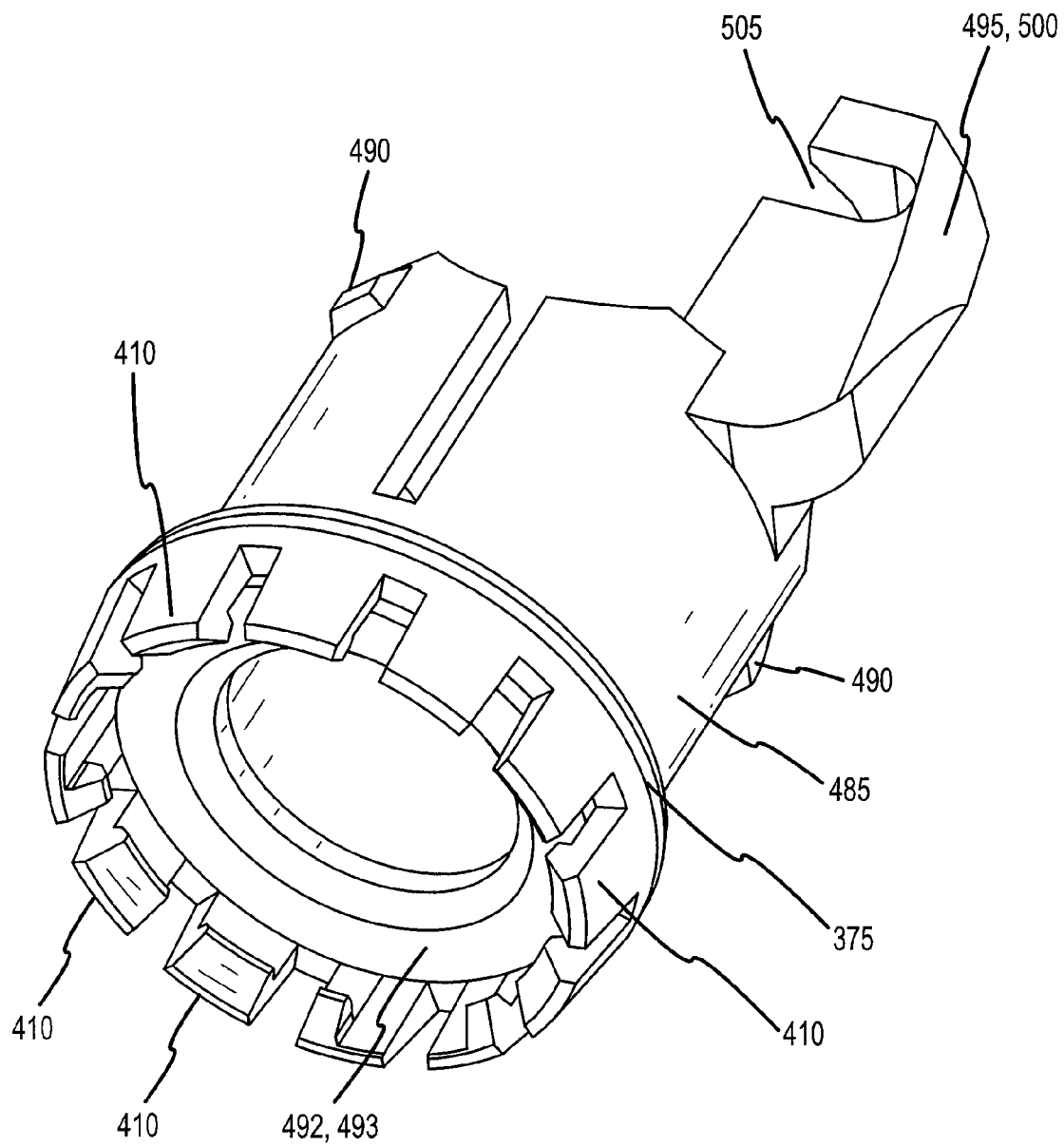
FIG. 32A is an isometric view of a second version of a valve actuator that is similar to the valve actuator depicted in FIG. 32, except the second version employs a latch ring with a plurality of latch fingers.
Figure 33:
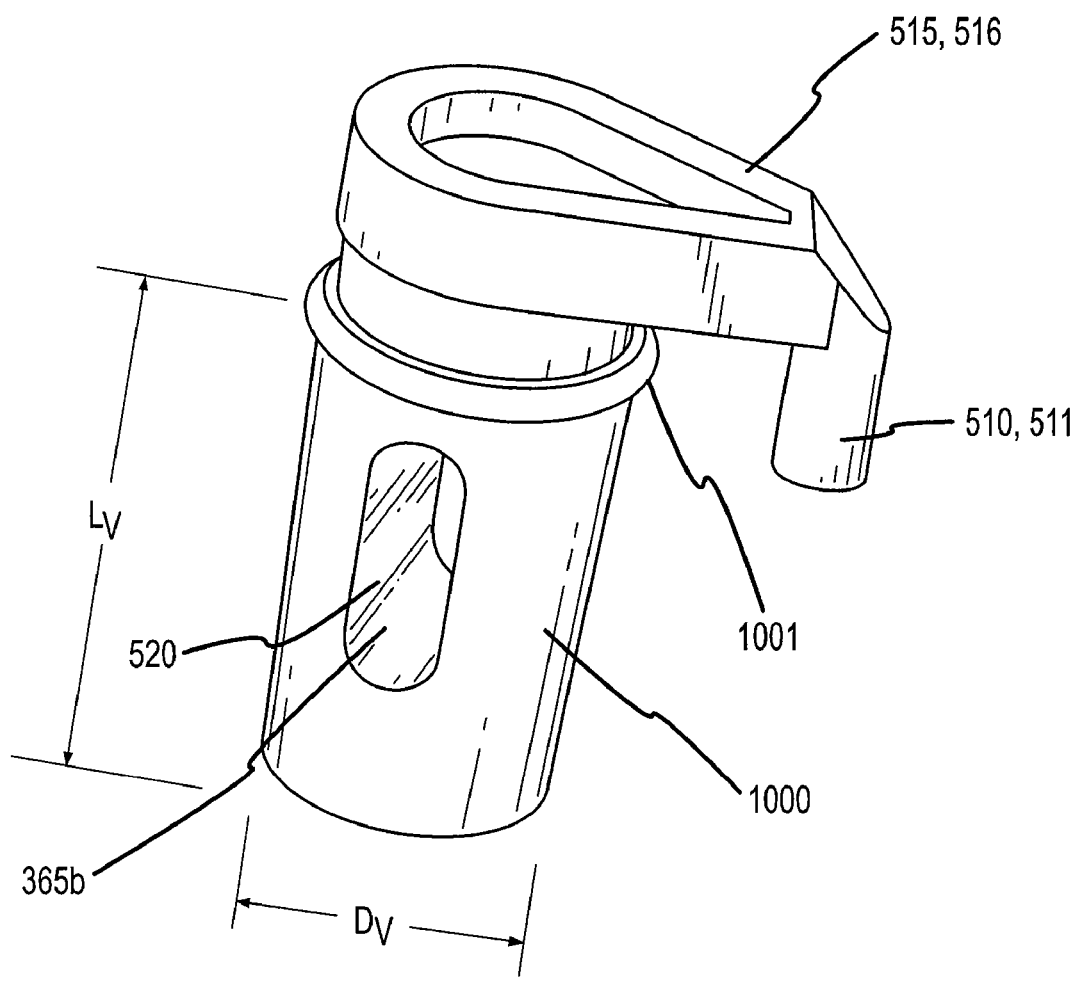
FIG. 33 is an isometric view of a valve as employed in the male and female couplers.

FIG. 32 is an isometric view of a valve actuator 366, 371 as employed in the male and female couplers 315, 320. FIG. 32A is an isometric view of a second version of a valve actuator 366, 371 that is similar to the valve actuator depicted in FIG. 32, except the second version employs a latch ring 375 with a plurality of latch fingers 410. FIG. 33 is an isometric view of a valve 370, 373 as employed in the male and female couplers 315, 320.

As shown in FIGS. 26 and 29, the male and female couplers 315, 320 each have joining ends 380, 385 that mate with, and couple to, the joining end 380, 385 of the other coupler 315, 320. Each joining end 380, 385 includes a seam face 390, 395 that forms a leading surface of each housing 345, 350. When the couplers 315, 320 are connected together, as illustrated in FIGS. 21-23, the seam faces 390, 395 abut to form the seam 355.

As illustrated in FIGS. 26 and 29, the male housing 345 includes upper and lower buttons 360 with engagement lips 400a, 400b that extend forwardly from the male housing 345 to engage with upper and lower engagement ridges or ring portions 405a, 405b formed in the inner surface of the female housing 350. As indicated in FIGS. 26, 29 and 32, in one version of the second embodiment, the leading end of each male and female valve actuator 366, 371 includes a latch finger 410, 411 that engages a groove 412, 413 that circumferentially extends about the outer circumferential surface of the leading tip of each barrel 366, 371. In another version of the second embodiment, as depicted in FIG. 32A, one of the valve actuators 366, 371 will have latch ring 375 with a plurality of latch fingers 410, and the other valve actuator 366, 371 will have a groove 413 for engagement by the plurality of latch fingers 410.

As will be discussed in greater detail later in this Detailed Description, when initially aligning the couplers 315, 320 in preparation for being connected to each other, but prior to pushing the joining ends 380, 385 together such that the housings 345, 350 engage each other, the latch fingers 410, 411 engage the grooves 412, 413. When the joining ends 380, 385 are then pushed together in order to cause the housings 345, 350 to engage such that the couplers 315, 320 fully engage, the lips 400 and ridges 405 engage to maintain the couplers 315, 320 in a connected state. The lips 400 and ridges 405 form the previously mentioned engagement mechanism. The lips 400 are disengaged from the ridges 405 by pressing inward on the buttons 360 and pulling the couplers 315, 320 longitudinally away from each other.

As indicated in FIGS. 28 and 31, the male and female couplers 315, 320 respectively include male and female barrels 367, 372 within the housings 345, 350. Each male and female barrel 367, 372 includes a faceplate 415, 420, an outer cylindrical wall 425, 430, a cylindrical neck 435, 440 coaxially centered within the cylindrical volume defined by the outer cylindrical wall 425, 430, and a cylindrical or ring shaped gap 445, 450 defined between the outer circumferential surface of the neck 435, 440 and the inner circumferential surface of the outer wall 425, 430.

Each neck 435, 440 protrudes forwardly relative to its respective faceplate 415, 420. The circular cross-sectioned fluid flow path 365a extends through the longitudinal center of each neck 435, 440. The fluid flow path 365a extends through the female neck 440 via a longitudinally extending orifice 455 that is sufficiently oversized to receive the outer circumferential surface 460 of the male neck 435 when the male neck 435 is plugged into the orifice 455 of the female neck 440. In one embodiment, the outer circumferential surface 460 of the male neck 435 and the orifice 455 of the female neck 440 are sufficiently close in size to form a fluid tight fit when the male neck 435 is plugged into the female neck 440. In one embodiment, an o-ring 465 extends in a groove about the outer circumferential surface 460 of the male neck 435 to provide a fluid tight fit when the male neck 435 is received within the orifice 455 of the female neck 440.

As shown in FIGS. 28 and 31, each barrel 367, 372 includes a barbed end 325, 330 on the end opposite from the joining ends 380, 385, a cylindrical opening or valve seat 466, 470 for receiving the valve 370, 373, and a longitudinally extending slot 475, 480 in the outer cylindrical wall 425, 430. The fluid flow path 365 extends through each barrel 367, 372 from the leading tip of each neck 435, 440 to the extreme tip of the barb end 325, 330.

As illustrated in FIG. 32, each valve actuator 366, 371 has a cylindrically shaped body 485, guides 490, a latch finger 410, 411, a groove 412, 413, a leading end face 492, 493, and an arm 495, 500. Alternatively, as depicted in FIG. 32A, one of the valve actuators 366, 371 will have a latch ring 375 with a plurality of latch fingers 410, and the other valve actuator 366, 371 will not have a latch ring 375 or latch fingers 410, 411, but will instead have only a groove 413 for engagement by the plurality of latch fingers 410 extending from the latch ring 375.

As shown in FIGS. 32 and 32A, each arm 495, 500 radially extends from the outer circumferential surface of the body 485 near the rear portion of the body 485. Each arm 495, 500 includes a slot or hole 505 that, as indicated in FIGS. 27 and 30, pivotally receives a pivot pin 510, 511 that extends from a lever arm 515, 516 of the valve 370, 373. As shown in FIGS. 28 and 31, the guides 490 radially extend from the outer circumferential surface of the body 485 to engage slots in the barrel 367, 372 to prevent the valve actuator 366, 371 from rotating within the barrel 367, 372.

As can be understood from FIGS. 27 and 30, the valve actuators 366, 371 are longitudinally displaceable about the necks 435, 440 of the barrels 367, 372 within the ring-like voids 445, 450 defined between the outer circumferential surfaces of the necks 435, 440 and the inner circumferential surfaces of the outer cylindrical walls 425, 430 of the barrels 367, 372. When the valve actuators 366, 371 longitudinally displace within the voids 445, 450, the arms 495, 500 displace within the longitudinally extending slots 475, 480 in the outer cylindrical walls 425, 430, which causes the valves 370, 373 to pivot within the valve seats 466, 470.

When the couplers 315, 320 are initially aligned for connection, the leading end faces 492, 493 are aligned and abutted against each other. At this time, each latch finger 410, 411 engages the groove 412, 413 of the other valve actuator 366, 371 to maintain the leading edge faces 482, 493 in alignment. When the couplers 315, 320 are then forced towards each other to cause the housings 345, 350 to become engaged via the coupling mechanism 400, 405, the valve actuators 366, 371 telescopically retreat against a biasing force about their respective necks 367, 372 into the ring-shaped voids 445, 450 in the barrels 367, 372. Each valve actuator 366, 371 is biased via a biasing mechanism (shown in later figures) towards the leading tip 520, 521 of each neck 435, 440. In one embodiment, the biasing mechanism is a helical spring (shown in later figures) extending about the outer circumferential surface of each neck 435, 440 between the neck 435, 440 and the inner circumferential surface of the valve actuator 367, 372.

As indicated in FIGS. 27 and 30, each barrel 367, 372 includes a valve 370, 373 that is located along the fluid flow path 365 between the back edge of the outer cylindrical wall 425, 430 and the barbed end 325, 330. As shown in FIG. 33, each valve 370, 373 has a cylindrical or barrel shaped body and includes a non-circular shaped orifice 520 that extends through the body of the valve 370, 373 perpendicular to the longitudinal axis of the body of the valve 370, 373. In one embodiment, the orifice 520 is rectangular and oriented such that its longitudinal axis coincides with the longitudinal axis of the body of the valve 370, 373. The orifice 520 serves as part of the rectangular cross-section fluid flow path 365b in each barrel 367, 372.

As shown in FIG. 33, each valve 370, 373 includes a lever arm 515, 516 that radially extends outward from the valve 370, 373. Each lever arm 515, 516 includes a pivot pin 510, 511 that extends downward from the lever arm 515, 516 generally parallel to the longitudinal axis of the body of the valve 370, 373. As indicated in FIGS. 27 and 30, each pivot pin 510, 511 is pivotally received in the slot or hole 505 (see FIG. 32) in the end of the arm 495, 500 of a valve actuator 366, 371.

As indicated in FIGS. 27, 28, 30 and 31, each barrel 367, 372 includes a cylindrical opening 466, 470 that receives therein the body of the valve 370, 373 and serves as a valve seat for the valve 370, 373. In a manner similar to that previously discussed regarding FIGS. 12 and 14 with respect to the first embodiment, the rectangular cross-section fluid flow path 365b penetrates each cylindrical opening 466, 470 to form a pair of rectangular openings 365b in the inner circumferential surface 466a, 470a of the cylindrical opening 466, 470. Each valve 370, 373 is pivotally displaceable about its longitudinal axis within its cylindrical opening or valve seat 466, 470 of a barrel 367, 372.

As can be understood from FIGS. 27 and 30, when the valve 370, 373 is pivotally displaced within the valve seat 466, 470 of a barrel 367, 372 such that the valve's lever arm 495, 500 is displaced away from the faceplate 415, 420 of the barrel 367, 372, the rectangular orifice 520 extending through each valve 370, 373 aligns with the rectangular openings 365b in the inner circumferential surface 466a, 470a of the valve seat 466, 470. As a result, the fluid flow path 365 extends uninterrupted through the barrel 367, 372 from the extreme end of the barbed end 320, 330 to the leading tip 520, 521 of the neck 435, 440. Conversely, when the valve 370, 373 is pivotally displaced within the valve seat 466, 470 of a barrel 367, 372 such that the valve's lever arm 495, 500 is displaced towards the faceplate 415, 420 of the barrel 367, 372, the rectangular orifice 520 extending through each valve 370, 373 does not coincide to any extent with the rectangular openings 365b in the inner circumferential surface 466a, 470a of the valve seat 466, 470. As a result, the fluid flow path 365 is sealed off or interrupted at the location of the valve 370, 373.

Figure 34:
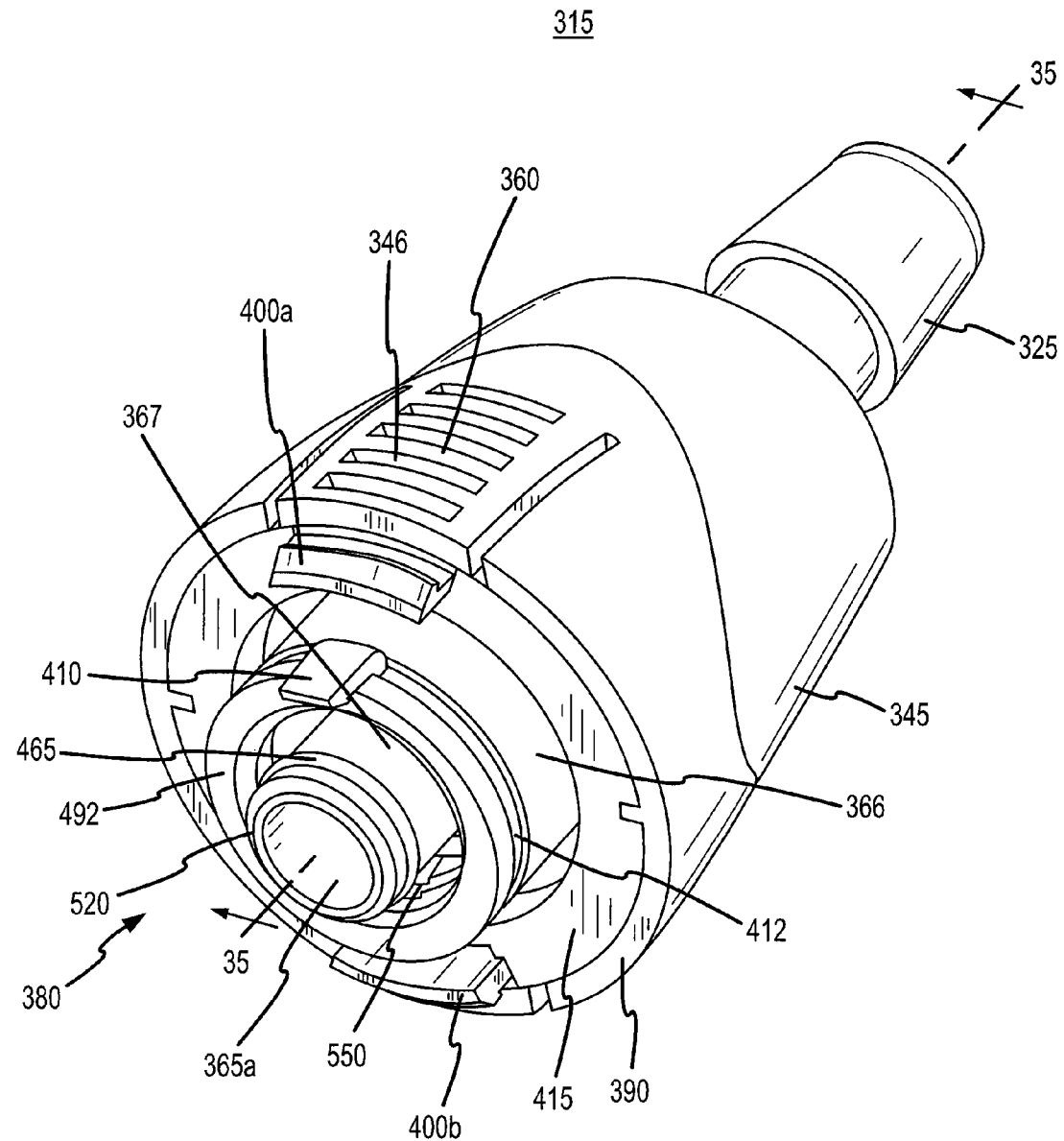
FIG. 34 is an isometric view of the male coupler as viewed from the joining side of the male coupler and indicating how a valve actuator of the male coupler would appear relative to a barrel of the male coupler when the male coupler is not connected to the female coupler.
Figure 35:
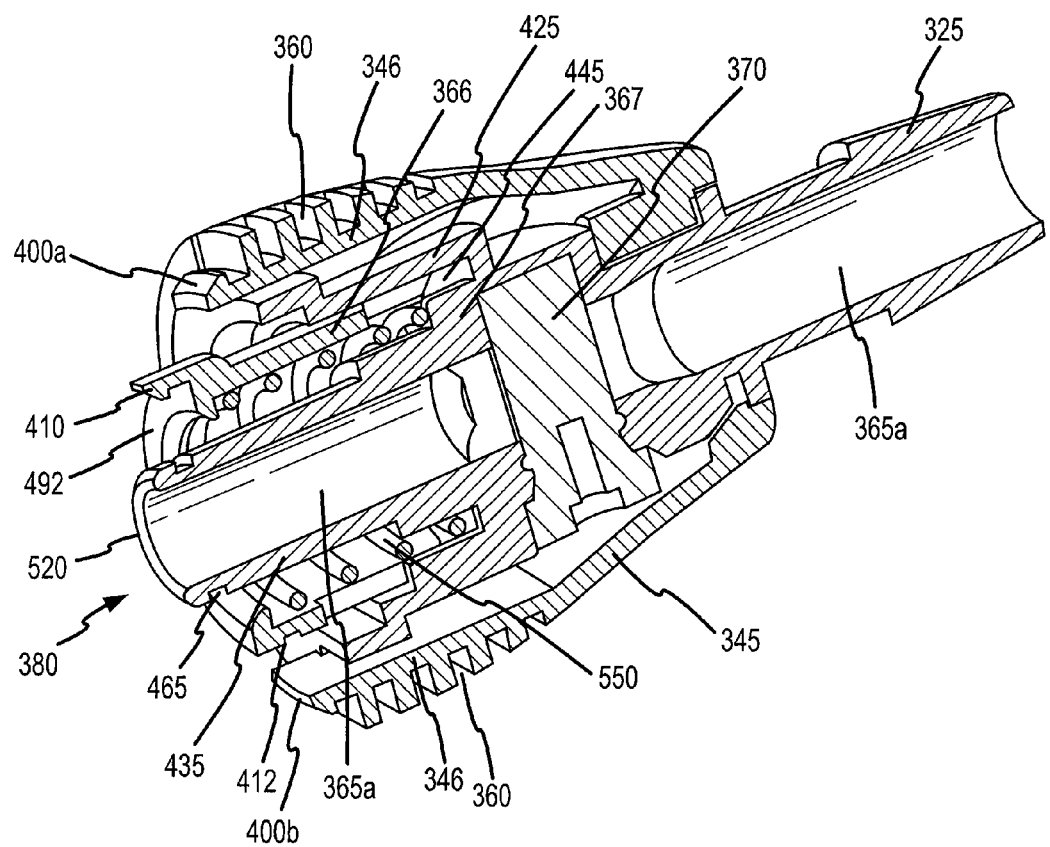
FIG. 35 is an isometric cross-sectional view of the male coupler as taken along section line 35-35 in FIG. 34.
Figure 36:
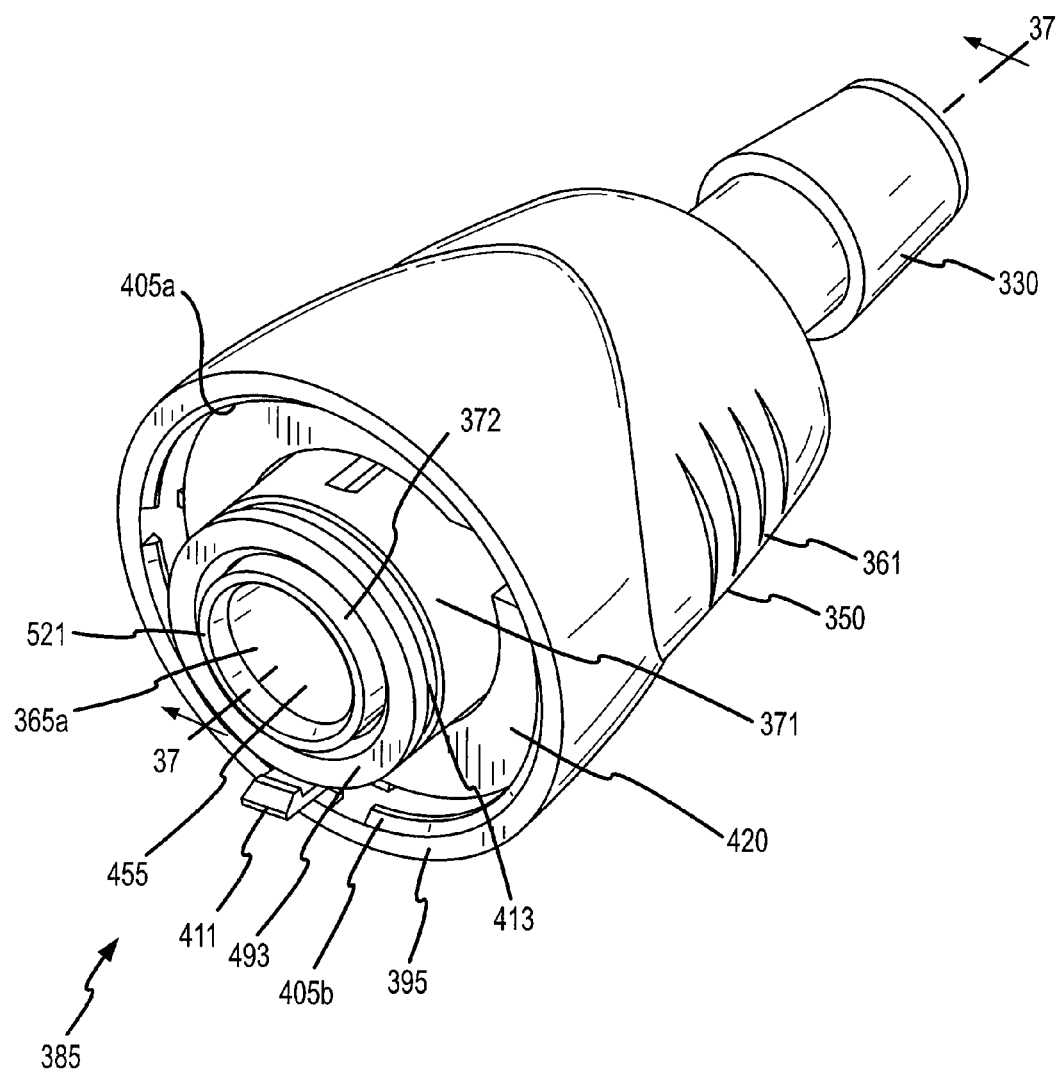
FIG. 36 is an isometric view of the female coupler as viewed from the joining side of the female coupler and indicating how a valve actuator of the female coupler would appear relative to a barrel of the female coupler when the female coupler is not connected to the male coupler.
Figure 37:
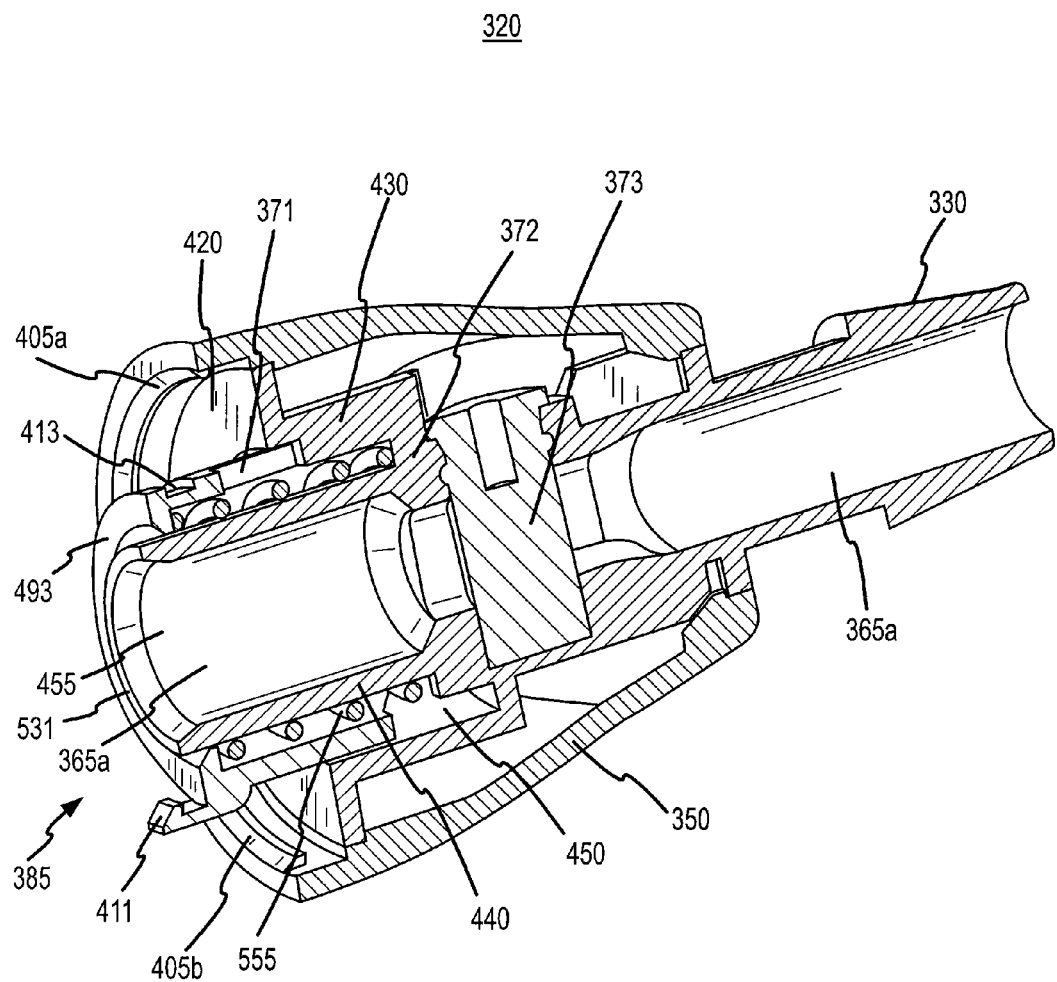
FIG. 37 is an isometric cross-sectional view of the female coupler as taken along section line 37-37 in FIG. 36.
Figure 38:
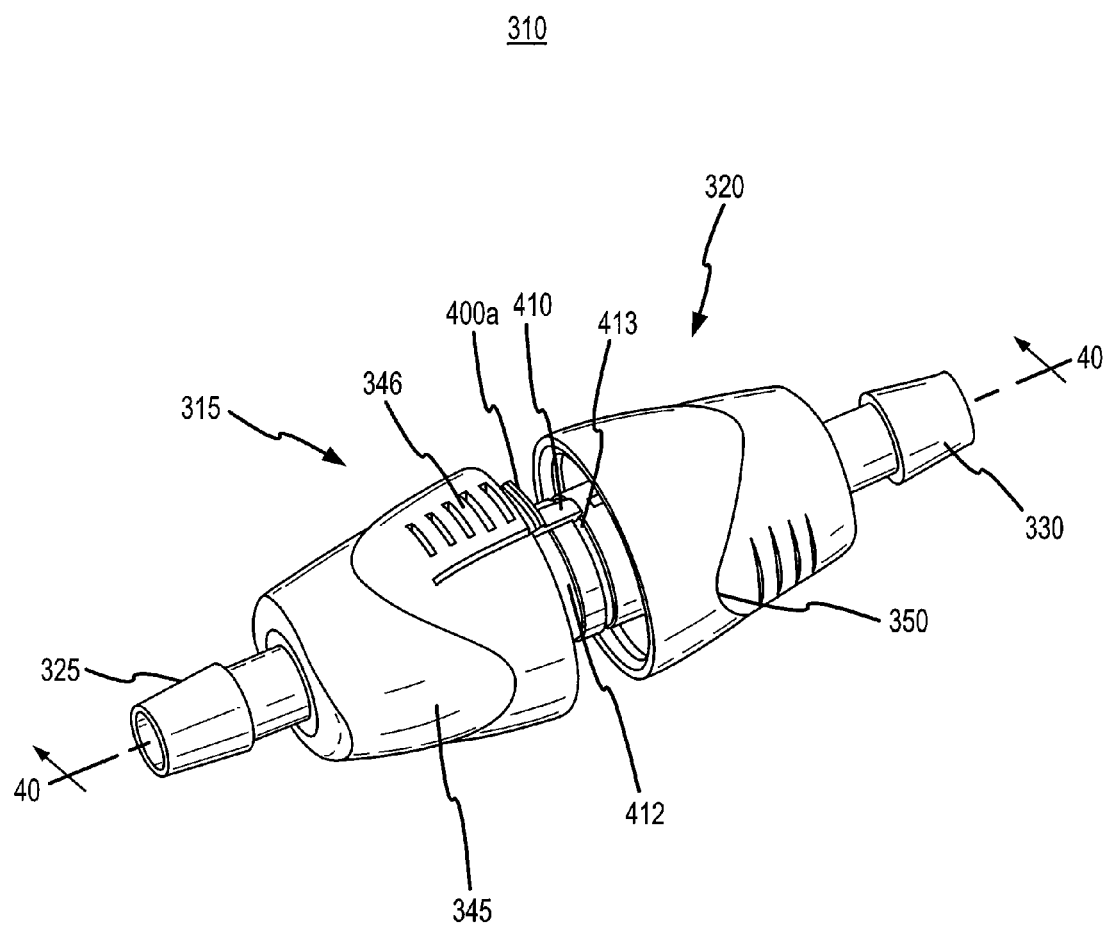
FIG. 38 is an isometric view of the male coupler being aligned for engagement with the female coupler, wherein the leading end faces of the valve actuators have abutted and the latch fingers have engaged the grooves on the valve actuators to maintain the valve actuators in an abutting alignment.
Figure 38A:
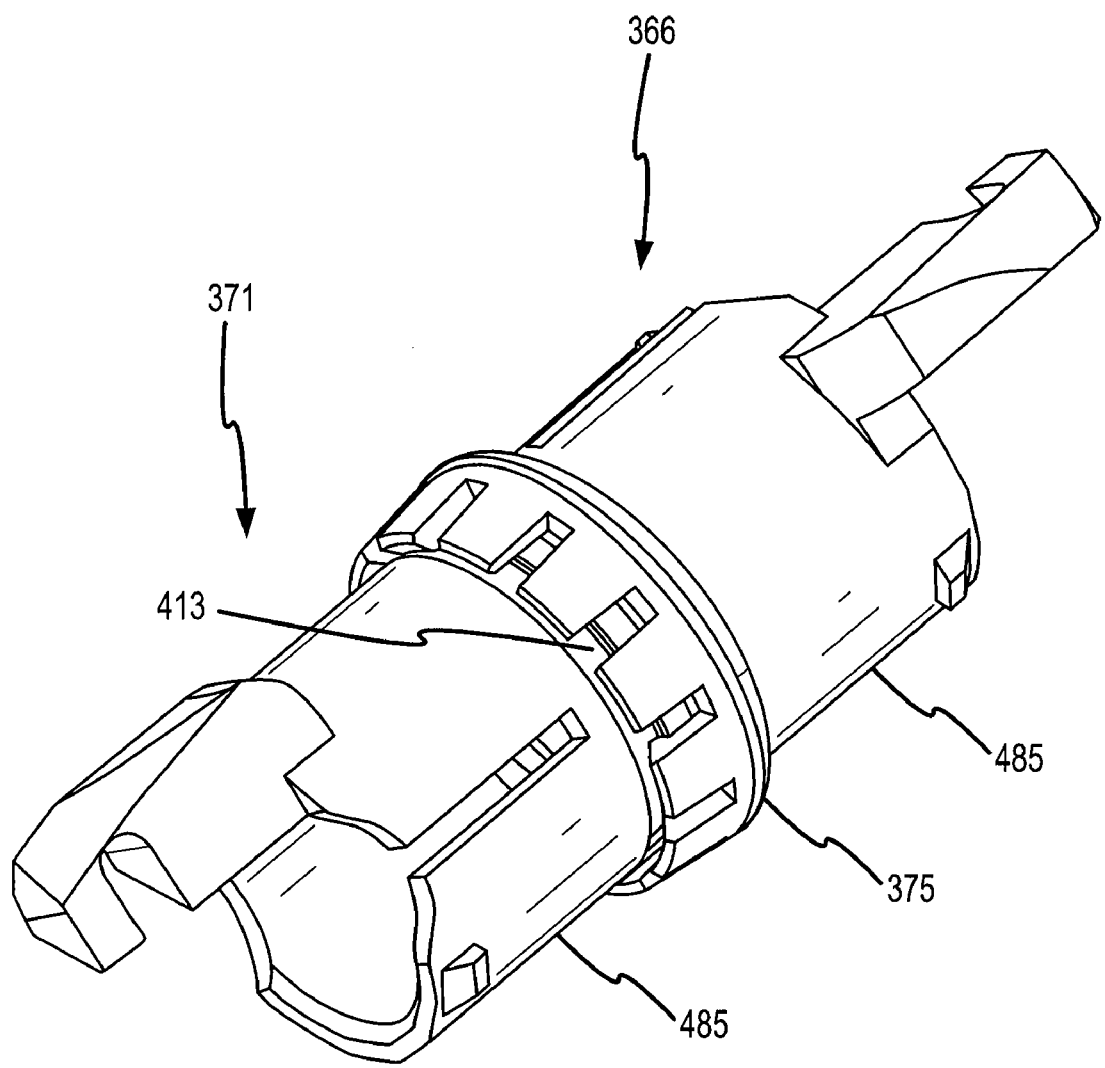
FIG. 38A is similar to FIG. 38, except only the valve actuators are illustrated and the valve actuator depicted in FIG. 32A is employed such that the plurality of latch fingers of a latch ring have engaged the groove of the opposing actuator when the actuators are in abutting contact.
Figure 39:
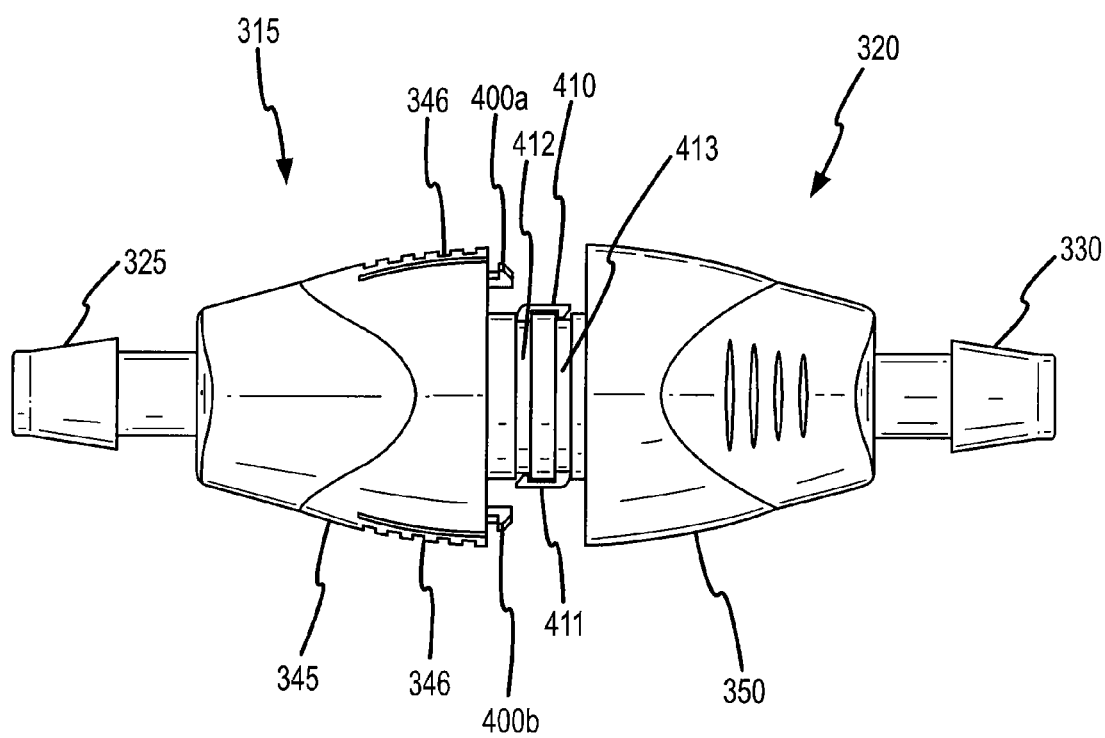
FIG. 39 is a side elevation of the male and female couplers as depicted in FIG. 38.
Figure 40:
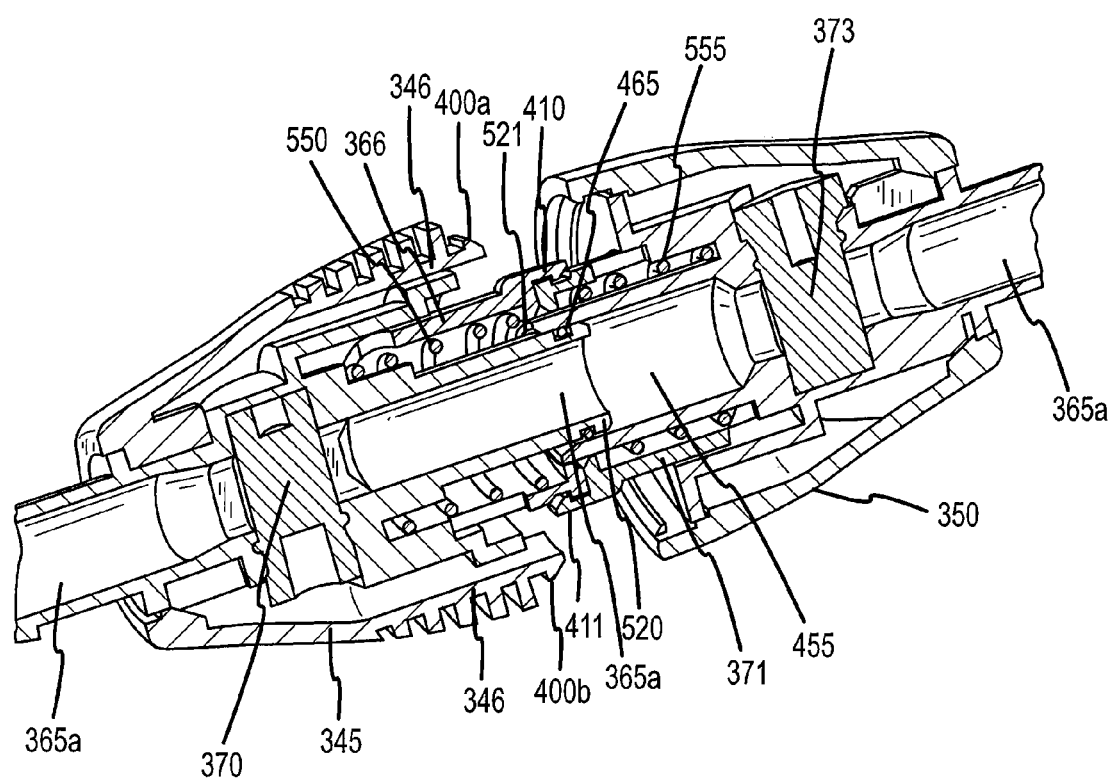
FIG. 40 is an isometric cross-sectional view of the male and female couplers as taken along section line 40-40 in FIG. 38.
Figure 41:
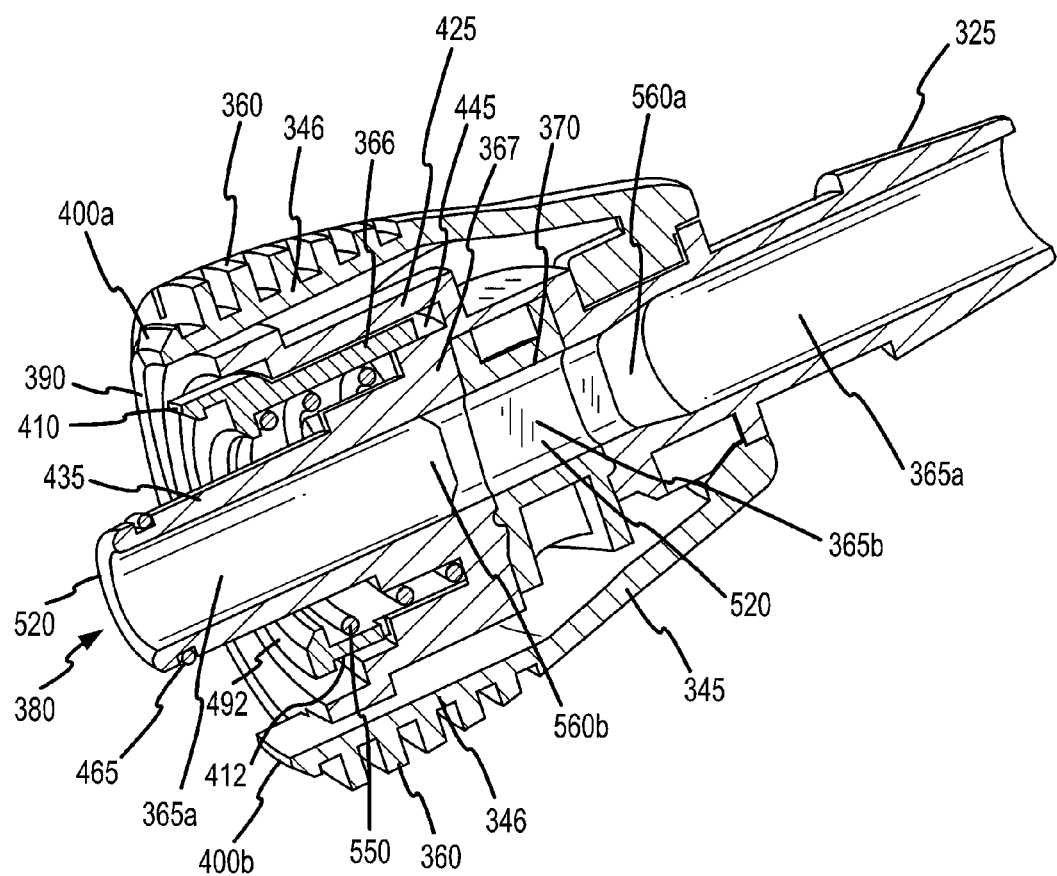
FIG. 41 is an isometric cross-sectional view of the male coupler as taken along section line 41-41 in FIG. 26.
Figure 42:
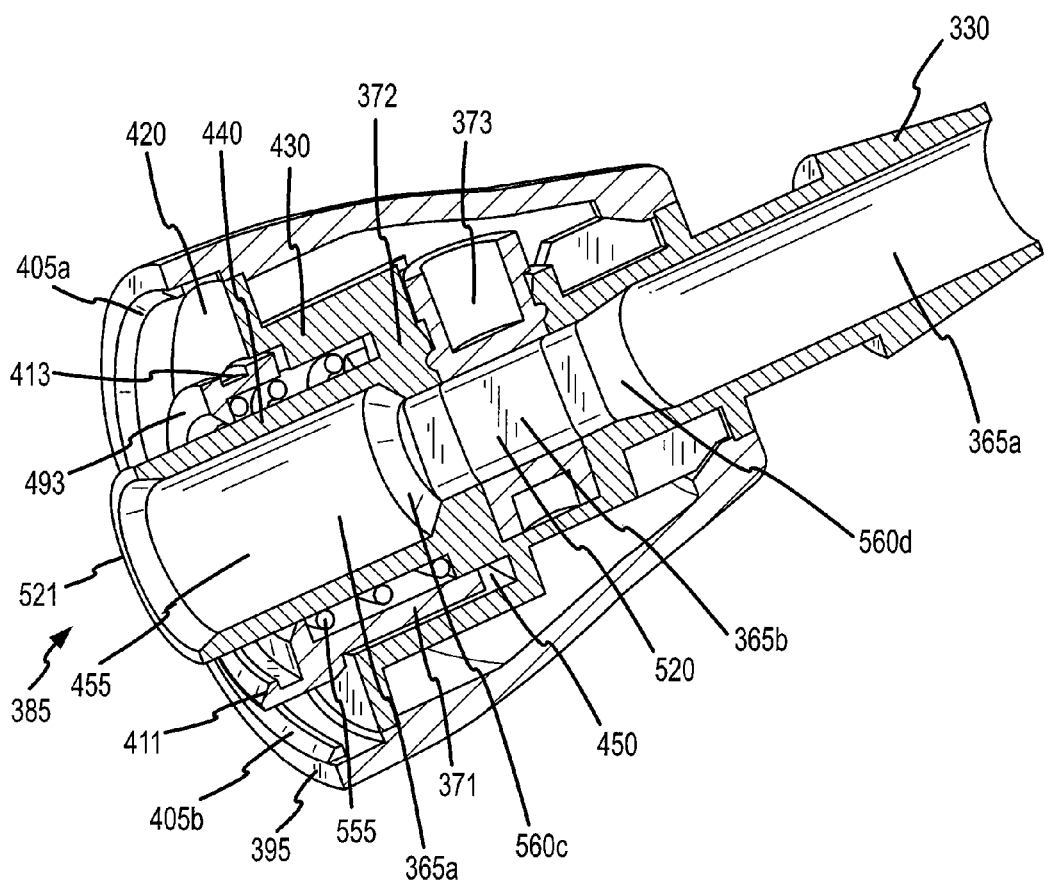
FIG. 42 is an isometric cross-sectional view of the female coupler as taken along section line 42-42 in FIG. 29.
Figure 43:
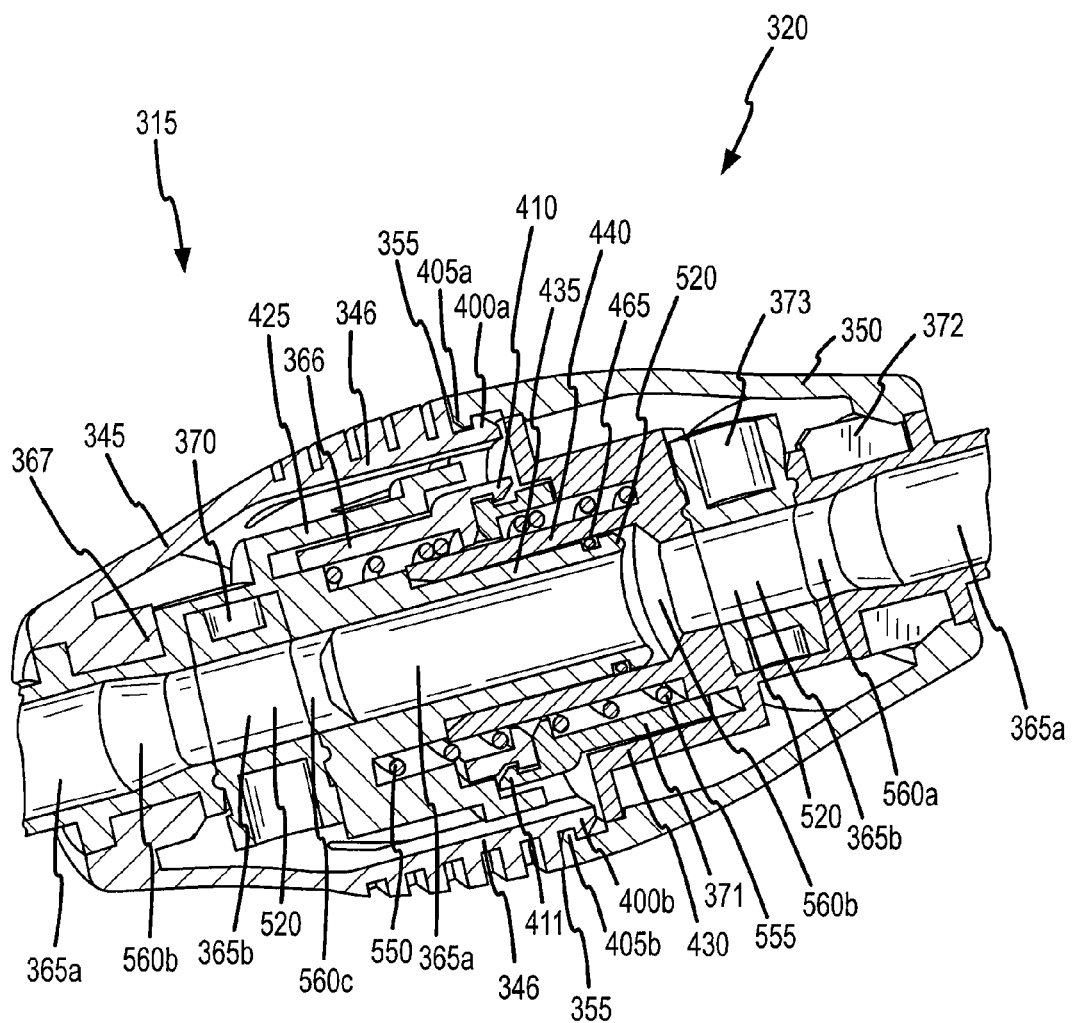
FIG. 43 is an isometric cross-sectional view of the male and female couplers as taken along section line 43-43 in FIG. 21.

For a better understanding of the interaction of the various components of the quick disconnect coupling assembly 310 when the male and female couplers 315, 320 are connected as illustrated in FIGS. 21-23, reference is made to FIGS. 21-23, 26, 27, 29, 30, and 34-43. FIG. 34 is an isometric view of the male coupler 315 as viewed from the joining side of the male coupler 315 and indicating how a valve actuator 366 of the male coupler 315 would appear relative to a barrel 367 of the male coupler 315 when the male coupler 315 is not connected to the female coupler 320. FIG. 35 is an isometric cross-sectional view of the male coupler 315 as taken along section line 35-35 in FIG. 34. FIG. 36 is an isometric view of the female coupler 320 as viewed from the joining side of the female coupler 320 and indicating how a valve actuator 371 of the female coupler 320 would appear relative to a barrel 372 of the female coupler 320 when the female coupler 320 is not connected to the male coupler 315. FIG. 37 is an isometric cross-sectional view of the female coupler 320 as taken along section line 37-37 in FIG. 36. FIG. 38 is an isometric view of the male coupler 315 being aligned for engagement with the female coupler 320, wherein the leading end faces 492, 493 of the valve actuators 366, 371 have abutted and the latch fingers 410, 411 have engaged the grooves 412, 413 on the valve actuators 366, 371 to maintain the valve actuators 366, 377 in an abutting alignment. FIG. 38A is similar to FIG. 38, except only the valve actuators 366, 371 are illustrated and the valve actuator depicted in FIG. 32A is employed such that the plurality of latch fingers 410 of a latch ring 375 have engaged the groove 413 of the opposing actuator 371 when the actuators 366, 371 are in abutting contact. FIG. 39 is a side elevation of the male and female couplers 315, 320 as depicted in FIG. 38. FIG. 40 is an isometric cross-sectional view of the male and female couplers 315, 320 as taken along section line 40-40 in FIG. 38. FIG. 41 is an isometric cross-sectional view of the male coupler 315 as taken along section line 41-41 in FIG. 26. FIG. 42 is an isometric cross-sectional view of the female coupler 320 as taken along section line 42-42 in FIG. 29. FIG. 43 is an isometric cross-sectional view of the male and female couplers 315, 320 as taken along section line 43-43 in FIG. 21.

As shown in FIGS. 34-37, when the male and female couplers 315, 320 are disconnected from each other, their respective valve actuators 366, 371 are biased by a biasing mechanism (e.g., a helical spring 550, 555) towards the leading tip 520, 521 of each neck 435, 440. As can be understood from FIGS. 27 and 30 and as indicated in FIGS. 35 and 37, because the valve actuators 366, 371 are biased in a position near the leading tips 520, 521 when the male and female couplers 315, 320 are not connected to each other, the valve actuator arms 495, 500 are positioned in the longitudinally extending barrel slots 475, 480 near the barrel faceplates 415, 420. As a result, the valves 370, 373 are caused to pivot within the valve seats 466, 470 via the linkage between the valve actuator arms 495, 500 and the valve lever arms 515, 516 such that the valve orifices 520 do not coincide with any part of the fluid flow path 365. Accordingly, the fluid flow path 365 is sealed at each valve 370, 373.

In aligning the couplers 315, 320 to facilitate their engagement, as depicted in FIGS. 21-23, the couplers 315, 320 are brought together such that the leading end faces 492, 493 of the valve actuators 366, 371 abut as shown in FIGS. 38-40 and 38A. When bringing the leading end faces 492, 493 into abutment, the latch fingers 410, 411 serve as guides to assist in achieving proper alignment between the couplers 315, 320. Also, when the leading end faces 492, 493 abut against each other, the latch fingers 410, 411 engage the grooves 412, 413 on the valve actuators 366, 371 to maintain the valve actuators 366, 377 in proper abutting alignment.

As indicated in FIG. 40, when the leading end faces 492, 493 of the valve actuators 366, 371 are in proper abutting alignment, the leading tip 520 of the male neck 435 is received in the orifice 455 of the leading tip 521 of the female neck 440. However, the valves 370, 373 remain pivoted in the closed positions because the valve actuators 366, 371 have not been caused to telescopically retreat against their respective biasing forces. The o-ring 465 provides a seal between the outer circumferential surface of the male neck 435 and the circumferential surface of the orifice 455.

After being properly abuttingly aligned as depicted in FIGS. 38-40 and 38A, the couplers 315, 320 can be fully engaged, as depicted in FIGS. 21-23 and 43, by pressing the couplers 315, 320 together with sufficient force to overcome the biasing force provided by the helical springs 550, 555 of the respective couplers 315, 320. In doing so, the valve actuators 366, 371 are caused to telescopically displace about the necks 435, 440 as the valve actuators 366, 371 retreat into the ring-like voids 445, 450 defined between the outer circumferential surfaces of the necks 435, 440 and the inner circumferential surfaces of the outer cylindrical walls 425, 430 of the barrels 367, 372.

As can be understood from FIGS. 27 and 30 and as indicated in FIGS. 41-43, because the valve actuators 366, 371 are forced away from the leading tips 520, 521 and well into the ring-like voids 445, 450 when the male and female couplers 315, 320 are connected to each other, the valve actuator arms 495, 500 are positioned in the longitudinally extending barrel slots 475, 480 near the valve seats 466, 470. As a result, the valves 370, 373 are caused to pivot within the valve seats 466, 470 via the linkage between the valve actuator arms 495, 500 and the valve lever arms 515, 516 such that the valve orifices 520 fully coincide with the fluid flow path 365. Accordingly, the fluid flow path 365 extends uninterrupted through the entire coupling assembly 10, including through each valve 370, 373.

As shown in FIG. 43, when the couplers 315, 320 are fully engaged, the engagement lips 400a, 400b of the male housing 345 attach to the ring portions 405a, 405b of the female housing 350 such that the seam face 390 (see FIG. 41) of the male housing 345 abuts against the seam face 395 (see FIG. 42) of the female housing 350 to form the seam 355 (see FIGS. 21-23). Also, as indicated in FIG. 43, when the couplers 315, 320 are fully engaged, the male neck 435 is fully inserted into the orifice 455 of the female neck 440.

As illustrated in FIGS. 41-43, the fluid flow path 365 has four transition points 560 where the fluid flow path 365 changes between circular and rectangular cross-sections. Following the fluid flow path 365 from the male barb end 325 towards the female barb end 330, the fluid flow path 365 begins as a circular cross-section fluid flow path 365a and transitions at a first transition point 560a to a rectangular cross-section fluid flow path 365b just prior to reaching the male valve 370. Shortly after passing through the male valve 370, the rectangular cross-section fluid flow path 365b transitions at a second transition point 560b to a circular cross-section fluid flow path 365a, which continues through the male neck 435. Shortly before reaching the female valve 373, the circular cross-section fluid flow path 365a transitions at a third transition point 560c to a rectangular cross-section fluid flow path 365b. Shortly after passing through the female valve 373, the rectangular cross-section fluid flow path 365b transitions at a fourth transition point 560d to a circular cross-section fluid flow path 365a, which continues to the female barbed end 330.

As can be understood from FIG. 33, transitioning from a circular to a rectangular cross-section fluid flow path 365 prior to passing through the orifice 520 of the valves 370, 373 allows the use of small diameter valve bodies and seats without having to settle for valve orifices 520 that have small fluid flow path cross-sections. As a result of using the generally rectangular valve orifices 520, the couplers 315, 320 of the present invention can have relatively thin housings 345, 350 without having valves 370, 373 with significant fluid flow constrictions that result in large pressure drops, as typically found in the art.

The couplers 315, 320 are disengaged from each other by first pressing inward the buttons 346 on the male housing 345 to cause the engagement lips 400a, 400b to detach from the ring portions 405a, 405b of the female housing 350. The couplers 315, 320 are then pulled longitudinally away from each other while continuing to press inward on the buttons 346. As the couplers 315, 320 are withdrawn from each other, the valve actuators 366, 371 are allowed to bias back towards the leading tip 520, 521 of the necks 435, 440, thereby causing the valves 370, 373 to pivot back to the closed position depicted in FIGS. 35, 37 and 40.

As can be understood from a review of FIGS. 11-16, 28, 31, 33, 35, 37 and 41-43, in one embodiment, the cylindrical or barrel shaped bodies of the valves 170, 175, 370, 373 are conically shaped such that they taper slightly when traveling along the longitudinal axis of the valve body away from the lever arm end. The conically shaped bodies of the valves are received in conically shaped cylindrical openings 235, 240, 466, 470 in the barrels 66, 67, 367, 372. The conically shaped cylindrical openings taper in a manner similar to the conically shaped cylindrical bodies of the valves.

For each of the disclosed embodiments of the fluid coupling assembly 10, 310, the various parts comprising the fluid coupling assembly are formed from polymer materials. In one embodiment, the housings 15, 20, 315, 320 are made from copolyester, nylon, CYROLITE®, or other similar polymers. In one embodiment, the actuators 366, 371 are made from copolyester, polycarbonate, polycarbonate blend, or other similar polymers. In one embodiment, the barrels 66, 67, 367, 372, including their cylindrical openings 235, 240, 466, 470, are formed from generally rigid types of polymer materials (e.g., hard polycarbonates, Teflon® impregnated polycarbonates, nylon 66, high density polyethylene ("HDPE"), etc.), and the cylindrical or barrel shaped bodies of the valves 170, 175, 370, 373 are formed from less rigid polymer materials (e.g., Delrin®, polyethylene, nylon 66, etc.).

In one embodiment, the barrels 66, 67, 367, 372 will be formed from a polymer material (e.g., hard polycarbonates, Teflon® impregnated polycarbonates, nylon 66, etc.) having a durometer range of approximately 118 to approximately 122 Rockwell R Scale, and the cylindrical or barrel shaped bodies of the valves 170, 175, 370, 373 will be formed from a polymer material (e.g., Delrin®, polyethylene, nylon 66, acetale, etc.) having a durometer range of approximately 107 to approximately 120 Rockwell R Scale.

In one embodiment, the barrels 66, 67, 367, 372 will be formed from a polymer material (e.g., hard polycarbonates, Teflon® impregnated polycarbonates, nylon 66, etc.) having a durometer range of approximately 118 to approximately 122 Rockwell R Scale, and the cylindrical or barrel shaped bodies of the valves 170, 175, 370, 373 will be formed from a polymer material (e.g., HDPE, nylon 66, Kynar®, etc.) having a durometer range of approximately 60 to approximately 65 Rockwell R Scale.

In one exemplary embodiment, where the diameter $D_v$ of the cylindrical body of the valve 170, 175, 370, 373 (see FIGS. 15 and 33) ranges between approximately 0.2 inch and approximately 0.5 inch and the length $L_v$ of the cylindrical body 1000 ranges between approximately 0.5 inch to 1.0 inch, a hard polycarbonate cylindrical opening 235, 240, 466,

470 is combined with a Delrin® or HDPE cylindrical valve body, and both the opening and valve body 1000 are conically shaped. In such a valve arrangement, the valve will be able to provide leak-free shutoff with a gas or liquid at a pressure of up to 60 psi and a fluid flow path 65, 365 through the valve that has a diameter (in a direction normal to the longitudinal axis of the cylindrical valve body) of approximately 10% to 75% (in one preferable embodiment, 60%) of the diameter $D_v$ of the cylindrical body of the valve. Thus, in one embodiment, where the diameter $D_v$ of the cylindrical body of the valve is 0.27 inch, the fluid flow path may be as large as approximately 0.20 inch in a direction transverse to the longitudinal axis of the cylindrical valve body.

Despite having fluid flow paths with diameters that are nearly as large as the diameters $D_v$ of the valve bodies, valves of the aforementioned sizes, configurations and materials are advantageous because they are able to provide the aforementioned leak-free shutoff performance without employing o-rings or other separate sealing elements between the surfaces of the cylindrical openings 235, 240, 466, 470 and the cylindrical bodies of the valves 170, 175, 370, 373.

During assembly, the conical valve bodies 1000 are forced into the conical openings 235, 240, 466, 470 in the barrels to seat the valve bodies 1000 in said openings. For example, in one embodiment, conical valve bodies 1000 are forced into the conical openings in the barrels via a valve body insertion force of between approximately 5 pounds and approximately 10 pounds of force. As each valve body 1000 is forced into its respective opening 235, 240, 466, 470 in a barrel 66, 67, 367, 372, a retaining rim 1001 (see FIG. 33) snaps into place within a groove 1002 (see FIG. 28) in the opening. As a result, the valve body 1000 is retained in the opening 235, 240, 466, 470 via a press fit (i.e., the engagement between the rim 1001 and groove 1002). The press fit maintains a press fit force between the conical valve body 1000 and conical opening 235, 240, 466, 470 that provides a pressure between the abutting surfaces of the conical valve body 1000 and the conical opening 235, 240, 466, 470 that is between approximately 2.0 psi and approximately 45.0 psi.

Because of the aforementioned material combinations and the wedging effect of the conical surfaces when the valve bodies are forced into and maintained within the openings, the surface irregularities common to polymer parts are eliminated, thereby providing the fit between the valve bodies and valve seats that is necessary to provide the aforementioned leak-free performance without the use of o-rings or other separate sealing elements between the surfaces of the valve bodies and valve seats. In other words, the pressure between the abutting surfaces of the valve bodies and valve seats, as maintained via the press fit, forms or flattens away the surface irregularities that plague polymer parts. Because of the elimination of the surface irregularities, the diameter of the fluid flow path through the valve body can be a substantially larger percentage of the diameter $D_v$ of the valve body than would otherwise be possible, especially considering no o-rings are utilized. Thus, the valve arrangement of the subject invention provides for substantially greater flow rates as compared to similarly sized valve arrangements in the art.

In one version of each of the disclosed embodiments of the fluid coupling assembly 10, 310, the fluid flow path 65, 365 extending through the assembly will have a circular cross-section. In another version of each of the disclosed embodiments of the fluid coupling assembly, the fluid flow path 65, 365 will transition between circular cross-sections and non-circular cross-sections, as previously described in this Detailed Description.

Figure 44:
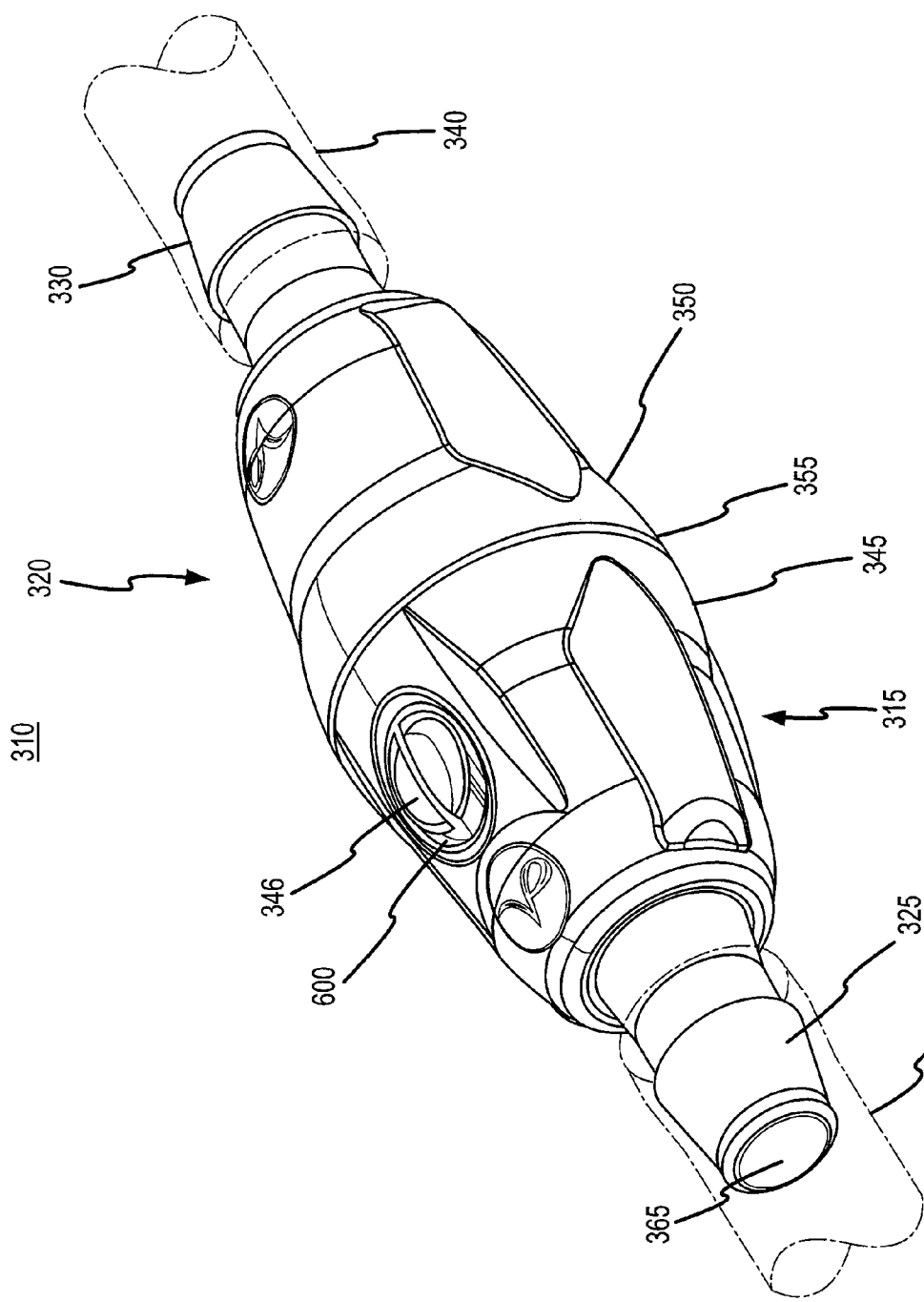
FIG. 44 is an isometric view of the quick disconnect coupling assembly, wherein the male coupler and female coupler are connected.
Figure 45:
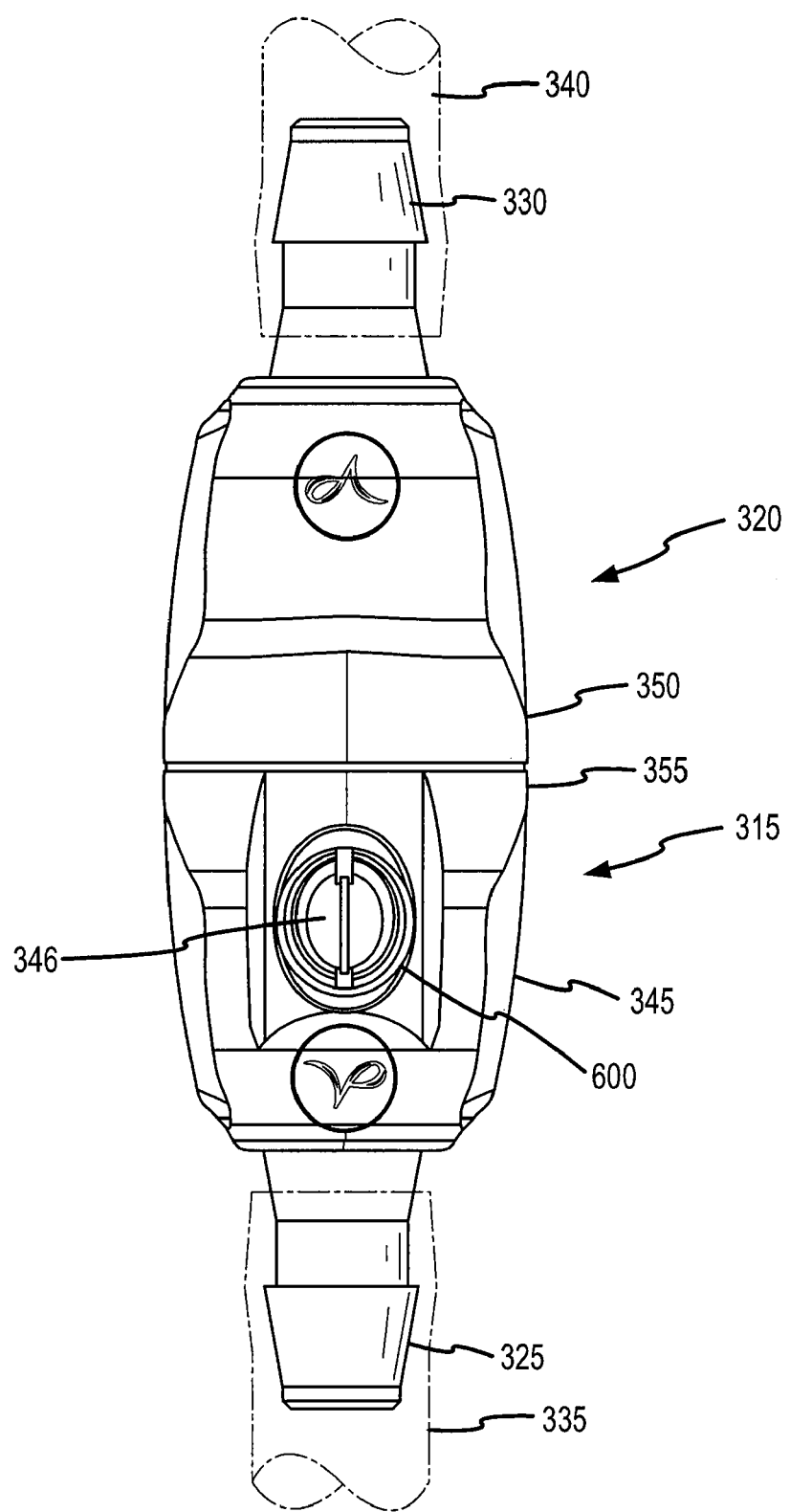
FIG. 45 is a top plan of the coupling assembly in the same connected state as depicted in FIG. 44.
Figure 46:
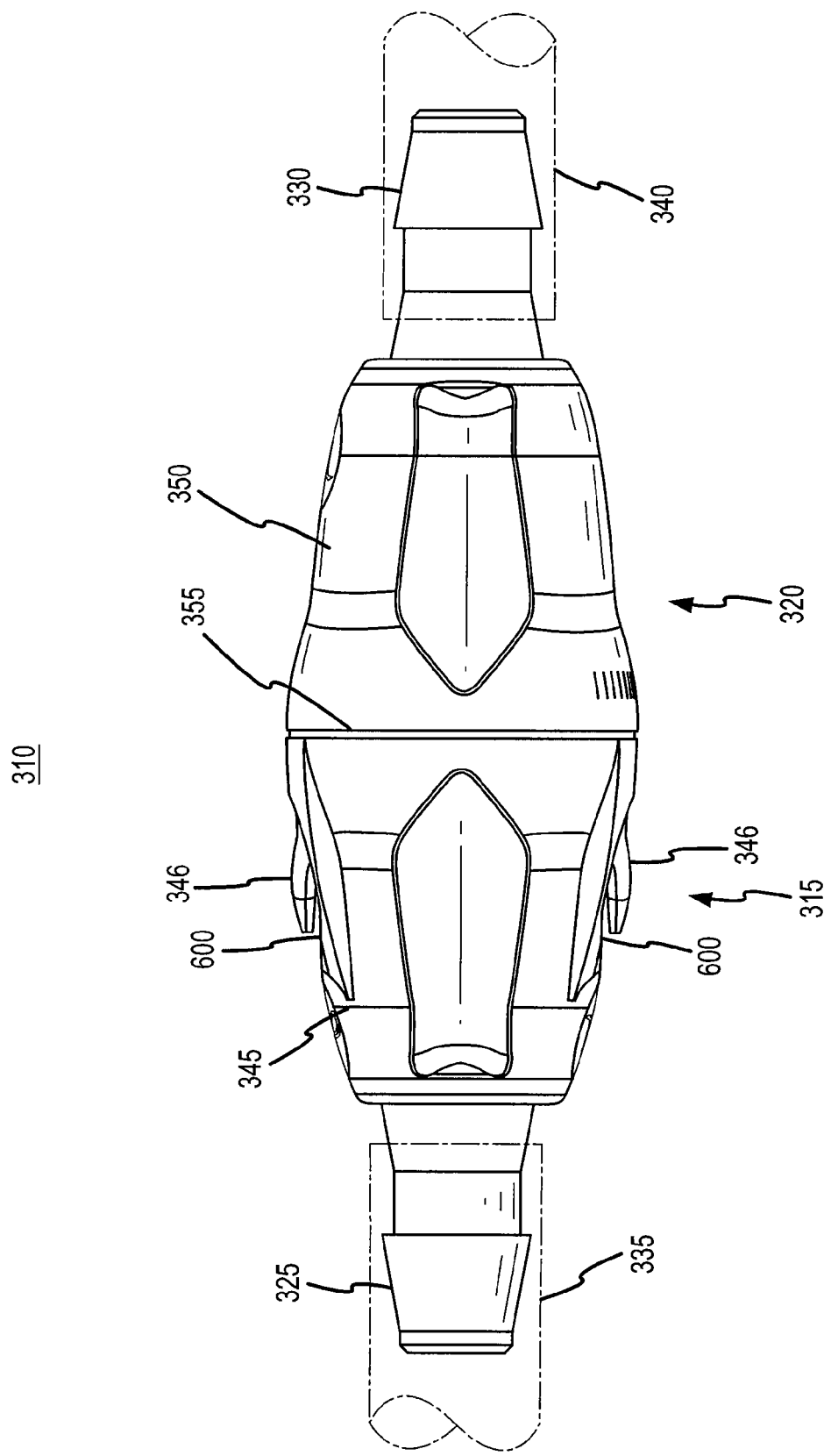
FIG. 46 is a side elevation of the coupling assembly in the same connected state depicted in FIG. 44.
Figure 47:
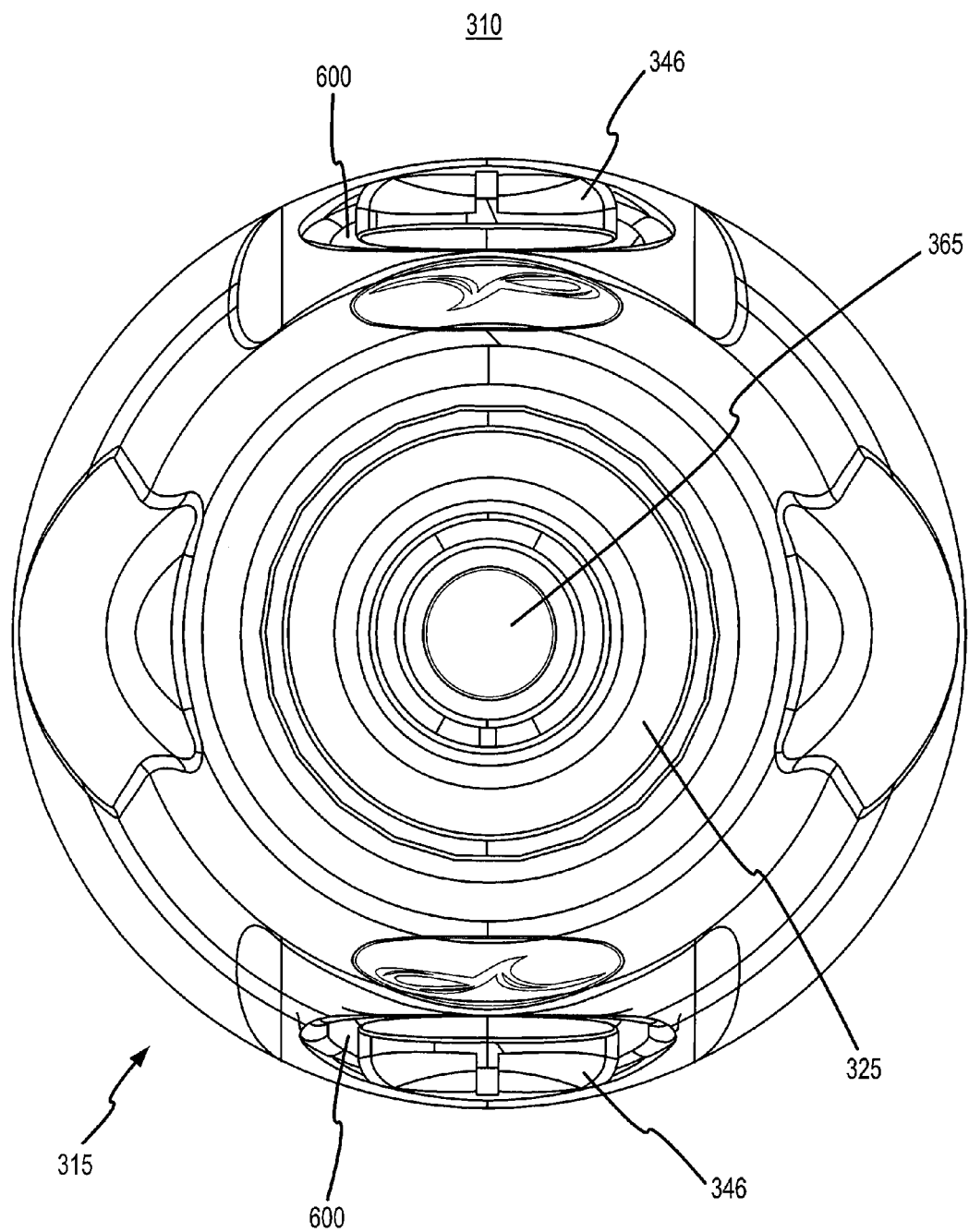
FIG. 47 is an end elevation of the coupling assembly in the same connected state depicted in FIG. 44 and as viewed from the male coupler end.
Figure 48:
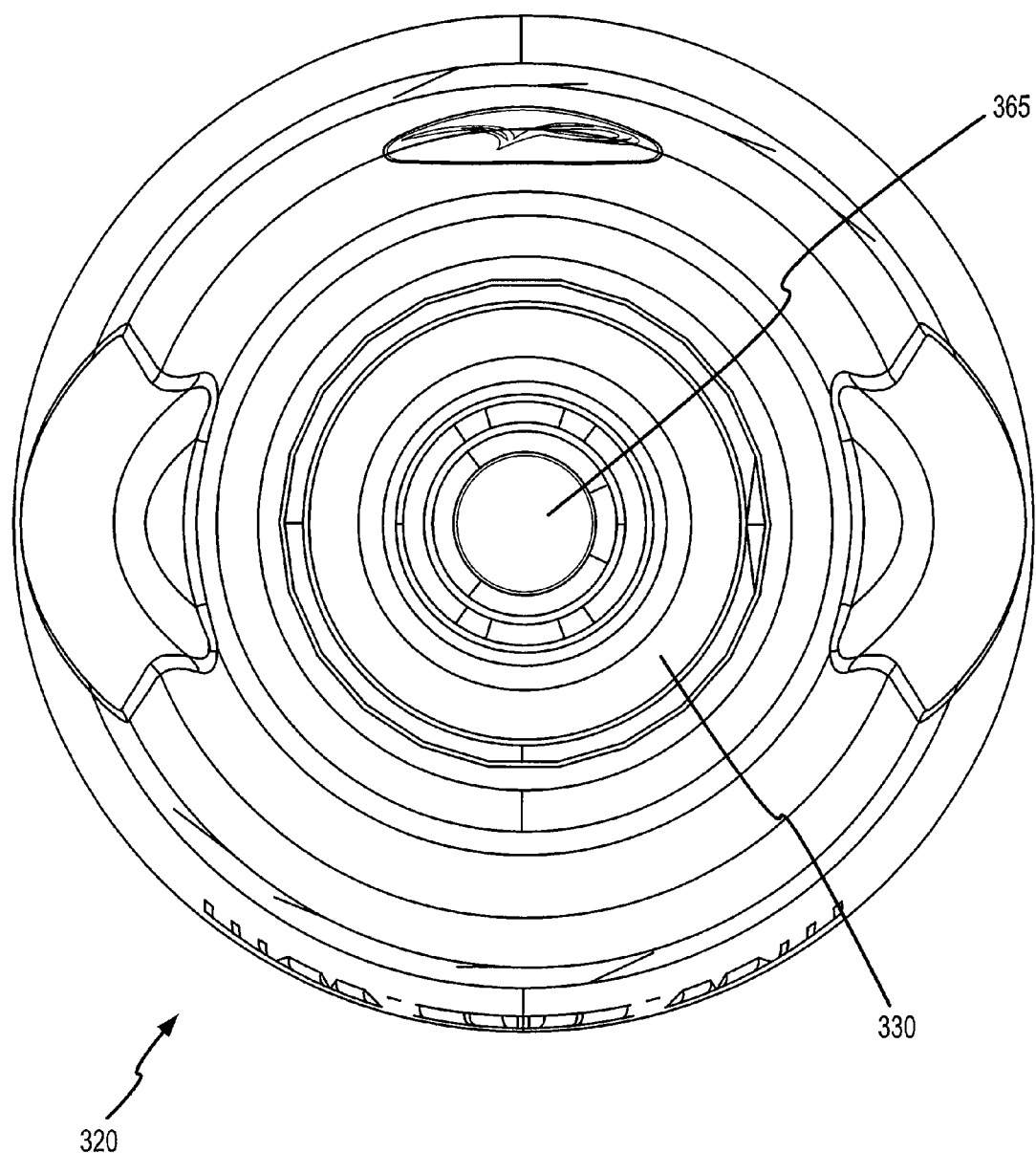
FIG. 48 is an end elevation of the coupling assembly in the same connected state depicted in FIG. 44 and as viewed from the female coupler end.
Figure 49:
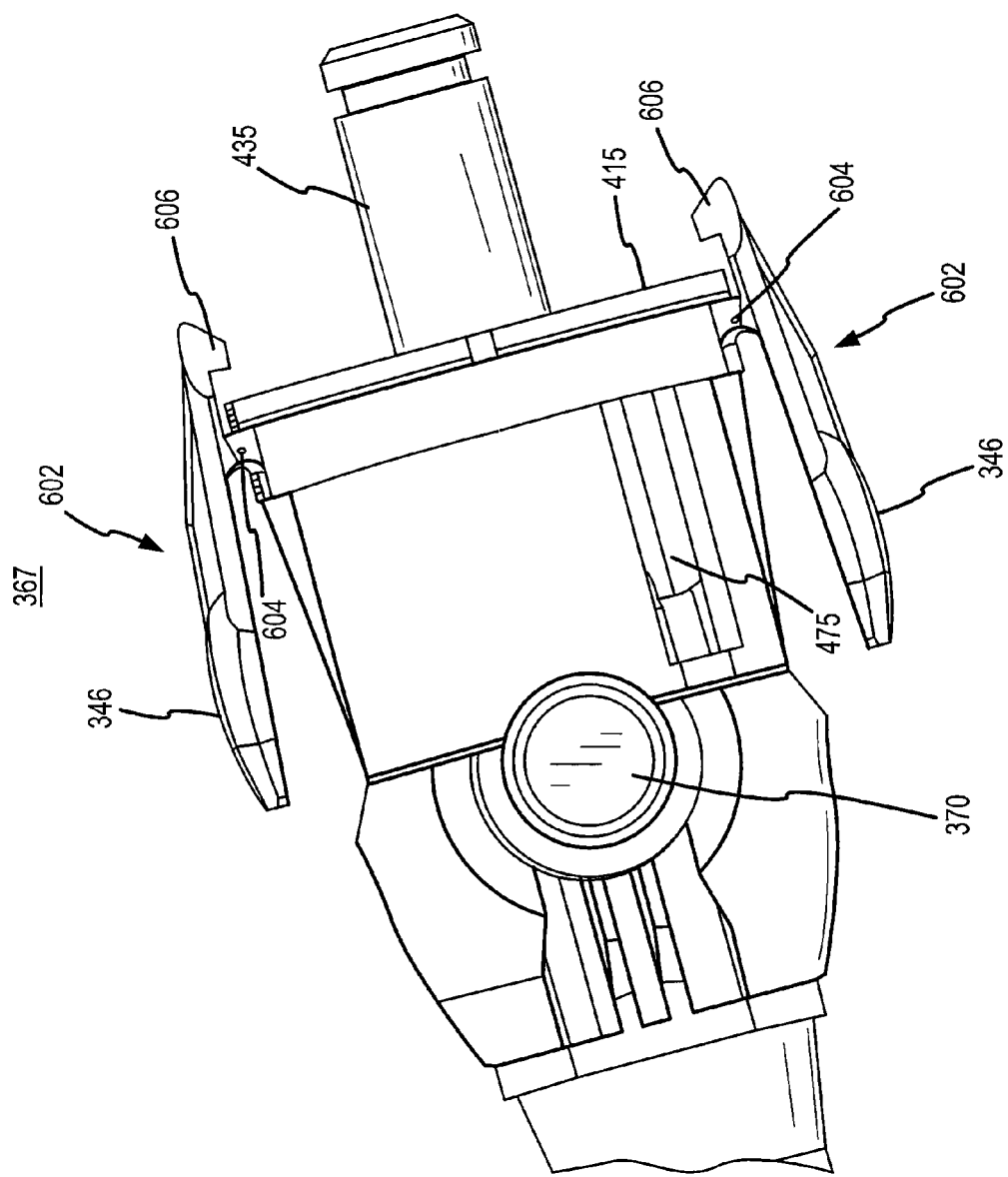
FIG. 49 is a side view of the male coupler with the male housing and the female coupler hidden to illustrate the engagement mechanism employed in the second version of the second embodiment of the coupling assembly.
Figure 50:
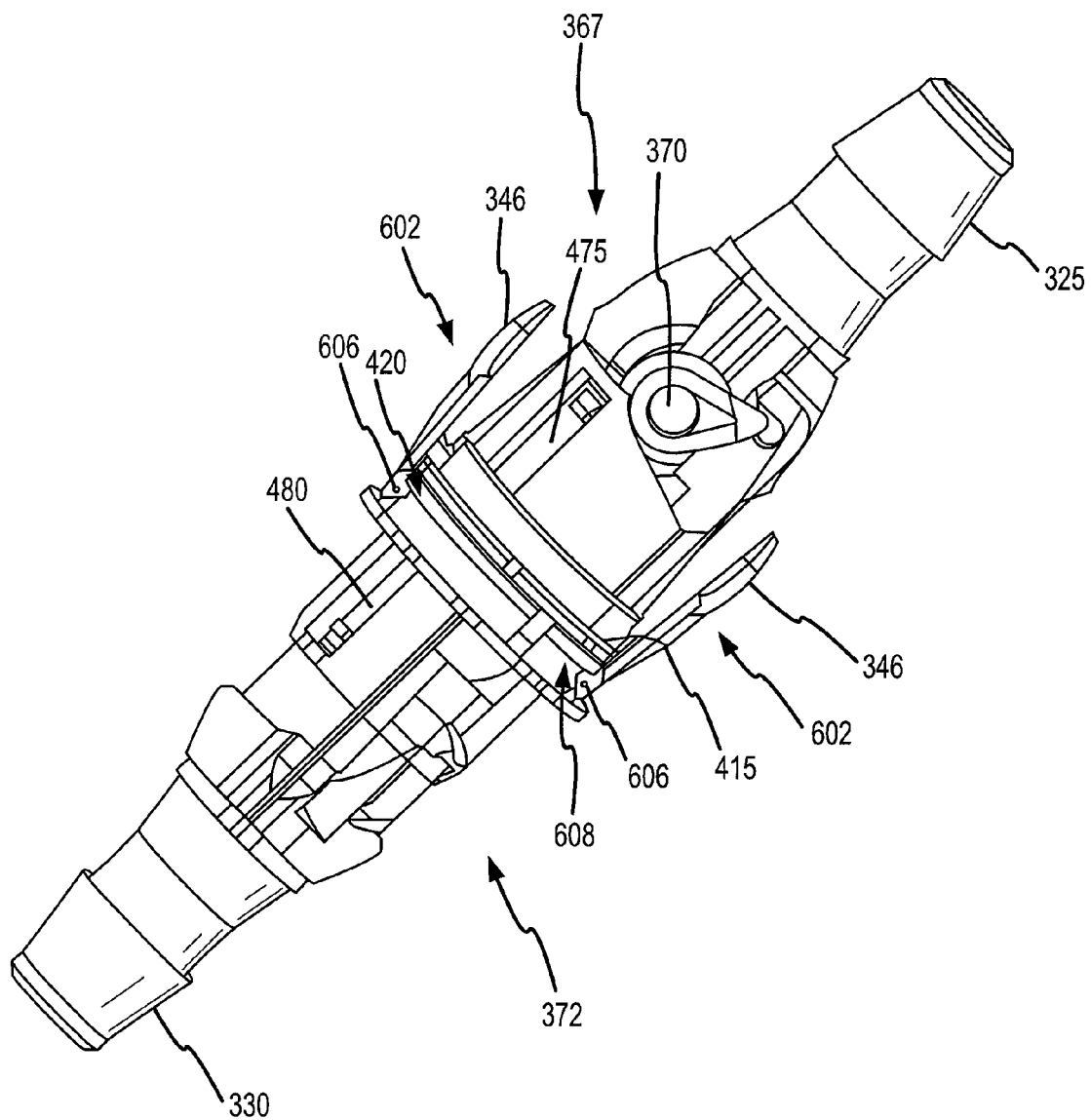
FIG. 50 is a side view of the coupling assembly that is generally similar to the side view depicted in FIG. 46, except the male and female housings are hidden to illustrate the engagement mechanism employed in the second version of the second embodiment of the coupling assembly.

For a discussion of a second version of the second embodiment of the quick disconnect coupling assembly 310 of the present invention, reference is made to FIGS. 44-50. FIG. 44 is an isometric view of the quick disconnect coupling assembly 310, wherein the male coupler 315 and female coupler 320 are connected. FIG. 45 is a top plan of the coupling assembly 310 in the same connected state as depicted in FIG. 44. While a bottom plan of the coupling assembly 310 is not provided, it should be understood that it would appear identical to the view depicted in FIG. 44. FIG. 46 is a side elevation of the coupling assembly 310 in the same connected state depicted in FIG. 44. While a view of the opposite side of the coupling assembly 310 is not provided, it should be understood that it would appear identical to the view depicted in FIG. 46. FIG. 47 is an end elevation of the coupling assembly 310 in the same connected state depicted in FIG. 44 and as viewed from the male coupler end. FIG. 48 is an end elevation of the coupling assembly 310 in the same connected state depicted in FIG. 44 and as viewed from the female coupler end. FIG. 49 is a side view of the male coupler 315 with the male housing 345 and the female coupler 320 hidden to illustrate the engagement mechanism employed in the second version of the second embodiment of the coupling assembly 310. FIG. 50 is a side view of the coupling assembly that is generally similar to the side view depicted in FIG. 46, except the male and female housings 345, 350 are hidden to illustrate the engagement mechanism employed in the second version of the second embodiment of the coupling assembly 310.

With the exception of the appearance of the male and female housings 345, 350 and the engagement mechanism illustrated in FIGS. 49 and 50, the second version of the second embodiment of the coupling assembly 310 has the same features and operation (including with respect to the valves 370, 373 and the valve actuators 366, 371) as the first version of the second embodiment of the coupling assembly 310 depicted in FIGS. 21-43. Accordingly, the preceding discussion of the features and operation of the first version of the second embodiment of the coupling assembly 310, as depicted in FIGS. 21-43, should be considered equally applicable to the second version of the second embodiment depicted in FIGS. 44-50, except as noted in the following discussion pertaining to the engagement mechanism and overall appearance of the male and female housings 345, 350.

As shown in FIG. 44-46, the quick disconnect coupling assembly 310 includes a male coupler 315 and a female coupler 320. Each coupler 315, 320 includes a barbed end 325, 330 for insertion into, and connection with, a fluid conduit 335, 340 such as medical grade flexible tubing. Each coupler 315, 320 includes a housing or shroud 345, 350 that forms the exterior shell of each coupler 315, 320. When the couplers 315, 320 are connected, as depicted in FIGS. 44-46, the housings 345, 350 form a body that is semi-elliptical or egg-shaped as viewed from above, below or from the sides, as shown in FIGS. 45 and 46.

When the couplers 315, 320 are connected via the engagement mechanism described in the following discussion, the joining ends of the housings 345, 350 of the coupler 315, 320 abut along a seam 355 that circumferentially latitudinally extends about the exterior shell of the coupling assembly 310. The male coupling housing 345 includes a pair of holes 600 on opposite sides of the housing 345. A button 346 extends through each hole 600 in the male housing 345.

As illustrated in FIGS. 49 and 50, the male and female barrels 367, 372 have the same general configuration and appearance as the male and female barrels 367, 372 illustrated in FIGS. 27, 28, 30 and 31, except the male barrel 367 includes a pair of resilient latching fingers 602 that are positioned on opposite sides of the male barrel 367 and are pivotal about a pivot 604 that integrally extends from the male barrel 367 in the vicinity of the face plate 415. Each latching finger 602 includes a button 346 at its proximal end and an engagement or hook end 606 at its distal end.

As illustrated in FIG. 49, the latching fingers 602 are biased so the hook ends 606 are biased towards each other and the buttons 346 are biased away from each other. As indicated in FIG. 50, when the male and female barrels 367, 372 are pushed together in mating engagement, the hook ends 606 engage the faceplate 420 or groove feature 608 on the exterior of the female barrel 372. Thus, the engagement mechanism used to couple the male and female couplers 315, 320 to each other for the second version of the second embodiment depicted in FIGS. 44-50 are elements of the barrels 367, 372 that engage each other. This is unlike the engagement mechanism utilized in the first version of the second embodiment depicted in FIGS. 21-43, wherein elements of the male and female housings 345, 350 engage each other (see FIGS. 21-23, 26, 29, 39, 40 and 43).

As indicated in FIGS. 44-48, because of the bias of the latching fingers 602, the buttons 346 protrude from their respective holes 600 until depressed by a user's finger when trying to disengage the male and female couplers 315, 320. When the buttons 346 are depressed, the hook ends 606 are caused to pivot out of engagement with the faceplate 420 or groove feature 608 on the exterior of the female barrel 372, and the male and female couplers 315, 320 and be withdrawn from each other.

As can be understood from FIGS. 44, 47 and 48, a fluid flow path 365 extends through the coupler assembly 310 from the male coupler barbed end 325 to the female coupler barbed end 330. In one embodiment, the fluid flow path 365 of the coupler assembly 310 depicted in FIGS. 44-50 will be similar to the fluid flow path 365 depicted in FIGS. 24 and 25, wherein the fluid flow path 365 makes the following transitions as it extends through the coupler assembly from the male barbed end 325 to the female barbed end 330: circular cross-section 365a to a rectangular cross-section 365b to a circular cross-section 365a to a rectangular cross-section to a circular cross-section 365a. In another embodiment, the fluid flow path of the coupler assembly 310 depicted in FIGS. 44-50 will have a circular cross-section along the entire length of the coupler assembly 310.

In summary, the present invention, as disclosed in the embodiments depicted in FIGS. 1-20 and 21-43, is a fluid conduit coupling assembly 10, 310 comprising a first coupler 15, 315 and a second coupler 20, 320. The couplers 15, 315, 20, 320 are adapted to couple to each other. Each coupler 15, 315, 20, 320 includes a valve 170, 175, 370, 373 that is automatically caused to pivot from a closed position to an open position via the act of coupling together the couplers 15, 315, 20, 320. Decoupling the couplers 15, 315, 20, 320 results in the valves 170, 175, 370, 373 automatically pivoting closed, thereby providing a positive shutoff for each coupler 170, 175, 370, 373 when decoupled.

Figure 51:
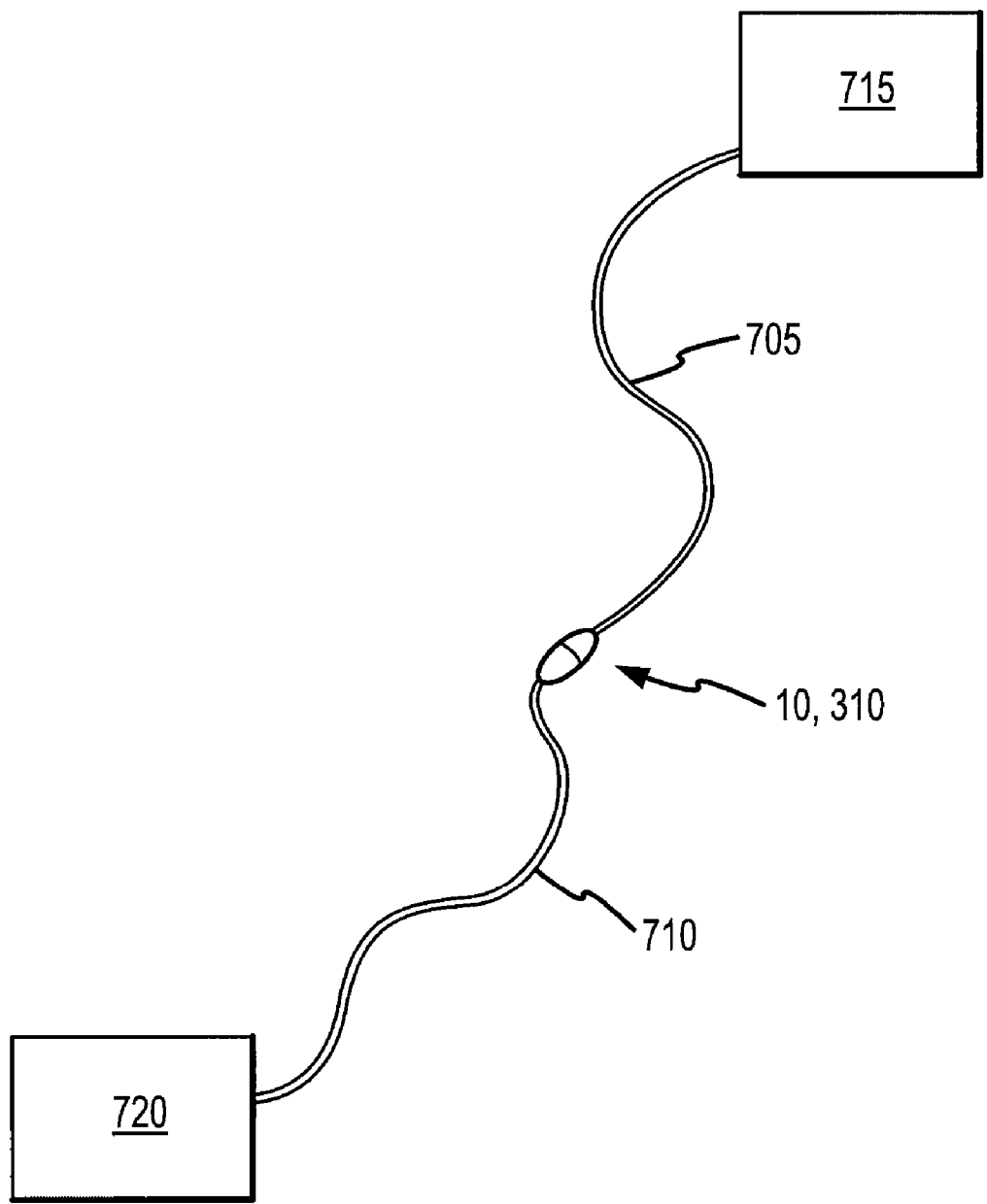
FIG. 51 is a schematic diagram of a fluid conduit coupling assembly of the subject invention being employed as part of a medical system.

As indicated in FIG. 51, in one embodiment the fluid conduit coupling assembly 10, 310 of the subject invention is utilized as part of a medical system 700 comprising the coupling assembly 10, 310, first and second fluid conduits 705, 710, a fluid origination point 715, and a fluid destination point 720. The coupling assembly 10, 310 joins the first fluid conduit 705 to the second fluid conduit 710. The first fluid conduit 705 extends between the coupling assembly 10, 310 and the fluid origination point 715. The second fluid conduit 710 extends between the coupling assembly 10, 310 and the fluid destination location 720. In one embodiment, the first and second fluid conduits 705, 710 are medical grade tubing. In one embodiment, the fluid origination point 715 is a first medical device or a first medical fluid reservoir 715. For example, in one embodiment, the fluid originating point 715 is an I.V. drip bag or other liquid reservoir whether the reservoir employs a rigid or flexible container, a blood pressure device, a medicament supplying device (e.g., insulin pump, etc.), a compressed gas source (e.g., compressed air system, oxygen system, carbon dioxide system, etc.), a medical treatment machine/device (e.g., a dialysis machine, etc.), a patient, or etc. In one embodiment, the fluid destination point 720 is a second medical treatment machine/device, a second medical fluid reservoir, or a patient 720. In one embodiment the fluid destination point 720 is a blood pressure cuff, a bladder or package, a reservoir for recirculation, collection vessels of all types, or etc.

The coupling assembly 10, 310 allows the fluid origination point 715 to be decoupled from the fluid destination point 720 with automatic positive shutoff. The coupling assembly 10, 310 also allows the fluid origination point 715 to be coupled with the fluid destination point 720 while automatically causing the two points 715, 720 to be placed in fluid communication.

Although the present invention has been described with reference to preferred embodiments, persons skilled in the art will recognize that changes may be made in form and detail without departing from the spirit and scope of the invention. The invention is limited only by the scope of the following claims.

What is claimed is:

1. A fluid conduit coupling assembly for coupling a first fluid conduit to a second fluid conduit, the fluid conduit coupling assembly comprising
   a first coupler comprising
      a first housing defining a pair of engagement lips extending from opposite positions on a first mating end;
      a first attachment end for attaching to the first fluid conduit;
      a first barrel at the first mating end forming a portion of a first fluid flow path extending between the first mating end and the first attachment end;
      a first valve in the first fluid flow path; and
   a second coupler comprising
      a second housing defining a ridge on an interior wall of the second housing at a second mating end for mating with the first mating end;
      a second attachment end for attaching to the second fluid conduit;
      a second barrel at the second mating end forming a portion of a second fluid flow path extending between the second mating end and the second attachment end;
      a second valve in the second fluid flow path; and
      a second valve actuation member in contact with the second valve; and
   at least one latch in either the first or second coupler extending from either the first or second mating end adjacent the first or second barrel, respectively;
   wherein either the first or second barrel of the first or second coupler opposing the at least one latch defines a circumferential groove in an outer wall at the first or second mating end, respectively;
   wherein the first and second valve actuation members open the first and second valves, respectively, when the first and second mating ends are mated together such that the first and second fluid flow paths are joined; and
   wherein the pair of engagement lips operably connect with the ridge on the second housing at the second mating end and the at least one latch mates with the groove when the first and second mating ends are mated together.

2. The fluid conduit coupling assembly of claim 1, wherein at least one of the first valve and second valve is pivotal between an open position and a closed position.

3. The fluid conduit coupling assembly of claim 1, wherein the at least one latch further comprises a plurality of latches extending from either the first or second mating end and the plurality of latches is arranged circumferentially around the first or second mating end.

4. A fluid conduit coupling assembly for coupling a first fluid conduit to a second fluid conduit, the fluid conduit coupling assembly comprising
a first coupler including a first mating end, a first attachment end for attaching to the first fluid conduit, a first fluid flow path extending between the first mating end and the first attachment end, a first engagement lip extending from an exterior portion of the first mating end, and a first valve in the first fluid flow path; and
a second coupler including a second mating end for mating with the first mating end, a second attachment end for attaching to the second fluid conduit, a second fluid flow path extending between the second mating end and the second attachment end, a ridge extending from an interior portion of the second mating end configured to receive the first engagement lip thereby securely attaching the first and second couplers when the first and second mating ends are mated together, and a first member adapted to open the first valve when the first and second mating ends are mated together such that the first and second fluid flow paths are joined, and
wherein the first valve includes a lever arm and the first member encounters the lever arm when the first and second mating ends are mated together, thereby causing the valve to pivot to the open position.

5. The fluid conduit coupling assembly of claim 4, wherein the first valve is biased to the closed position.

6. The fluid conduit coupling assembly of claim 5, wherein the first valve is biased via a helical spring.

7. The fluid conduit coupling assembly of claim 4, wherein the first valve is a stopcock, plug valve or ball valve.

8. A fluid conduit coupling assembly for coupling a first fluid conduit to a second fluid conduit, the fluid conduit coupling assembly comprising a first coupler comprising
a first housing defining a first engagement lip and a second engagement lip extending from opposite positions on a first mating end, the first housing including a first release mechanism and a second release mechanism on opposite positions on the first housing, wherein the first engagement lip is operatively connected to the first release mechanism and the second engagement lip is operatively connected to the second release mechanism;
a first attachment end for attaching to the first fluid conduit;
a first barrel at the first mating end forming a first fluid flow path extending between the first mating end and the first attachment end;
a first valve in the first fluid flow path and including a lever arm; and
a first valve actuator coupled to the lever arm of the first valve; and
a second coupler comprising
a second housing defining a ridge on an interior wall of the second housing at a second mating end for mating with the first mating end;
a second attachment end for attaching to the second fluid conduit; and
a second barrel at the second mating end forming a portion of a second fluid flow path extending between the second mating end and the second attachment end;
a second valve in the second fluid flow path; and
a second valve actuator operably coupled to the second valve; and
at least one latch in either the first or second coupler extending from either the first or second mating end adjacent the first or second barrel, respectively;
wherein either the first or second barrel of the first or second coupler opposing the at least one latch defines a circumferential groove in an outer wall at the first or second mating end, respectively;
wherein when the first and second mating ends are mated together such that the first and second fluid flow paths are joined, the first and second engagement lips operably connect with the ridge on the second housing at the second mating end, the at least one latch mates with the circumferential groove, and the first valve actuator abuts against the second valve actuator of the second coupler and is displaced, thereby causing the first valve to open, and
the second valve actuator abuts against the first valve actuator of the first coupler and is displaced, thereby causing the second valve to open.

9. The fluid conduit coupling assembly of claim 8, wherein the first valve is pivotal between an open position and a closed position.

10. The fluid conduit coupling assembly of claim 9, wherein the first valve is a stopcock, plug valve or ball valve.

11. The fluid conduit coupling assembly of claim 8, wherein the first valve actuator telescopically displaces about the first fluid flow path upon abutting against the second valve actuator of the second coupler.

12. A fluid conduit coupling assembly for coupling a first fluid conduit to a second fluid conduit, the fluid conduit coupling assembly comprising
a first coupler for connecting to the first fluid conduit and comprising:
a first housing including a cantilever button;
a tab operably connected to and extending from the cantilever button at a first mating end; and
a first valve, wherein the first valve comprises a first lever arm; and
a second coupler for connecting to the second fluid conduit and comprising:
a second housing including a ridge on an inner wall at a second mating end of the second coupler; and
a second valve, wherein the second valve comprises a second lever arm,
wherein when a force is applied to couple together the couplers, at least a portion of said force is communicated to each lever arm, thereby causing each valve to pivot from a closed position to an open position,
wherein the first coupler further comprises a first structural member, the second coupler further comprises a second structural member, and when the couplers are coupled together, the first structural member extends into the second coupler to contact the second lever arm and the second structural member extends into the first coupler to contact the first lever arm, and
wherein the first coupler and the second coupler are coupled together the tab securely attaches to the ridge and when the cantilever button is depressed, the tab releases from the ridge.

13. A method of coupling a first fluid conduit to a second fluid conduit, the method comprising providing a first coupler connected to the first fluid conduit and a second coupler connected to the second fluid conduit, wherein
the first coupler includes a first housing, a first latch, an engagement tab, and a first valve having a lever arm; and
the second coupler includes a second housing, a second latch, and a second valve having a lever arm;
aligning a mating end of the first coupler with a mating end of the second coupler;
operably connecting the first latch with mating end of the second coupler;
operable connecting the second latch with the mating end of the first coupler;
applying a force to the couplers to cause the mating ends to engage;
engaging the engagement tab with second housing; and
communicating at least a portion of the force to the lever arm of each the first and second valve to cause each the first and second valve to pivot from a closed position to an open position,
wherein when the mating ends engage, a structural member of each coupler enters the other coupler and displaces the lever arm of said other coupler.

14. A coupling assembly for coupling a first fluid conduit to a second fluid conduit, the coupling assembly comprising
a first coupler comprising
a first attachment end configured to attach to the first fluid conduit;
a first housing defining a first engagement lip and a second engagement lip extending from opposite positions on a first mating end, the first housing including a first button operatively connected to the first engagement lip and a second button operatively connected to the second engagement lip;
a first barrel at the first mating end forming a portion of a first fluid flow path extending between the first attachment end and the first mating end, the first barrel defining a first circumferential groove in an outer wall at the first mating end;
a first latch extending from the first mating end adjacent the first barrel;
a second coupler comprising:
a second attachment end configured to attach to the second fluid conduit;
a second housing defining a ridge on an interior wall of the second housing at a second mating end for mating with the first mating end;
a second barrel at the second mating end forming a portion of a second fluid flow path extending between the second mating end and the second attachment end, the second barrel defining a second circumferential groove in an outer wall of the second mating end;
a second latch extending from the second mating end adjacent the second barrel;
wherein when the first coupler and the second coupler are mated together such that the first and second fluid paths are joined, the first latch mates with the second circumferential groove, the second latch mates with the first circumferential groove, and the first and second engagement lips operably connect with the ridge on the second housing at the second mating end.

15. The coupling assembly of claim 14, wherein when the first coupler and second coupler are mated together, depressing the first button detaches the first engagement lip from the ridge on the second housing and depressing the second button detaches the second engagement lip from the ridge on the second housing.

16. The coupling assembly of claim 14, wherein when the first coupler and the second coupler are mated together, the first latch mates to the second circumferential groove and the second latch mates to the first circumferential groove before the first engagement lip and the second engagement lip operably connect with the ridge on the second housing at the second mating end.

17. A coupling assembly for coupling a first fluid conduit to a second fluid conduit, the coupling assembly comprising
a first coupler comprising
a first attachment end configured to attach to the first fluid conduit;
a first mating end, the first mating end including a first fluid flow path extending between the first attachment end and the first mating end; and
a first housing surrounding the first fluid flow path, the first housing including at least one button, wherein the at least one button includes a hook at a first end of the at least one button;
a second coupler comprising
a second attachment end configured to attach to the second fluid conduit;
a second mating end, the second mating end including a second fluid flow path extending between the second attachment end and the second mating end; and
a second housing surrounding the second fluid flow path, the second housing defining a groove configured to receive the hook on the at least one button of the first housing;
wherein when the first coupler and the second coupler are mated together such that the first and second fluid paths are joined, the hook operably connects to the groove.

18. The coupling assembly of claim 17, wherein when the hook is operably connected to the groove, the at least one button is angled away from the first housing.

* * * * *